United States Patent
Kammer et al.

(10) Patent No.: US 9,549,843 B2
(45) Date of Patent: Jan. 24, 2017

(54) PRODUCTION OF WELL-MIXED SURGICAL SLUSH

(71) Applicant: C° Change Surgical LLC, Winston-Salem, NC (US)

(72) Inventors: Patrick Kammer, Greensboro, NC (US); Kevin Joseph Rackers, Summerfield, NC (US); Benjamin A. Perrot, Greensboro, NC (US)

(73) Assignee: C° Change Surgical LLC, Winston-Salem, NC (US)

( * ) Notice: Subject to any disclaimer, the term of this patent is extended or adjusted under 35 U.S.C. 154(b) by 28 days.

(21) Appl. No.: 14/875,589

(22) Filed: Oct. 5, 2015

(65) Prior Publication Data
US 2016/0151200 A1    Jun. 2, 2016

Related U.S. Application Data

(60) Provisional application No. 62/085,590, filed on Nov. 30, 2014.

(51) Int. Cl.
*F25C 1/10* (2006.01)
*A23G 9/00* (2006.01)
(Continued)

(52) U.S. Cl.
CPC ............... *A61F 7/0085* (2013.01); *F25C 1/20* (2013.01); *A61F 7/10* (2013.01); *A61F 2007/0098* (2013.01); *F25C 2301/002* (2013.01)

(58) Field of Classification Search
CPC ..... F25C 1/10; F25C 2500/08; F25C 2700/08; A23G 9/00; A23G 9/04; A23G 9/103; A23G 9/106; A23G 9/18; A23G 9/20; A23G 9/16; A23G 9/163
(Continued)

(56) References Cited

U.S. PATENT DOCUMENTS 71,448 A * 11/1867 Bruckner .................. B01F 9/04
                                                    366/220
714,415 A    11/1902 Trafford
(Continued)

FOREIGN PATENT DOCUMENTS

JP          06123532        5/1994

OTHER PUBLICATIONS

Bae, Geun Tae, Written Opinion of the International Searching Authority for PCT/US2015/062921 (PCT application related to the present application), Mar. 21, 2016, 9 pages, Korean Intellectual Property Office, Daejeon, South Korea.
(Continued)

*Primary Examiner* — Frantz Jules
*Assistant Examiner* — Erik Mendoza-Wilkenfe
(74) *Attorney, Agent, or Firm* — Kevin E Flynn; Flynn IP Law

(57) ABSTRACT

Creation of surgical slush having desirable mechanical properties by chilling a closed slush container with liquid saline and an air gap. The closed slush container having interior surfaces that are smooth and hydrophobic to resist adherence of ice crystals. Moving the closed slush container so the contents move in a complex set of motions rather than constant rotation around a longitudinal centerline of the slush container as the liquid saline is converted into surgical slush with a mixture of liquid saline and ice crystals. Interior surfaces of the closed slush container move into and out of an air gap to help shed any ice crystals forming on the interior surfaces. In some instances, as the orientation of the closed slush container relative to gravity changes over time, different interior surfaces shed the ice crystals. An optional method for delivering surgical slush to the sterile field is included. The full range of the disclosure exceeds the scope of this brief abstract.

32 Claims, 33 Drawing Sheets

(51) Int. Cl.
*A23G 9/04* (2006.01)
*A61F 7/00* (2006.01)
*F25C 1/20* (2006.01)
*A61F 7/10* (2006.01)

(58) Field of Classification Search
USPC .......................................... 366/220, 232, 239
See application file for complete search history.

(56) References Cited

U.S. PATENT DOCUMENTS

| | | | |
|---|---|---|---|
| 2,555,624 A | 6/1951 | Anderson et al. | |
| 2,993,350 A | 7/1961 | Smith et al. | |
| 3,998,070 A | 12/1976 | Mueller | |
| 4,393,659 A | 7/1983 | Keyes et al. | |
| 4,435,082 A | 3/1984 | Bishop | |
| 4,526,012 A | 7/1985 | Chigira | |
| 4,580,405 A | 4/1986 | Cretzmeyer, III | |
| 4,669,274 A | 6/1987 | Huang | |
| 4,722,198 A | 2/1988 | Huang | |
| 4,813,243 A | 3/1989 | Woods et al. | |
| 4,934,152 A | 6/1990 | Templeton | |
| 5,163,299 A | 11/1992 | Faries, Jr. et al. | |
| 5,174,306 A | 12/1992 | Marshall | |
| 5,282,368 A | 2/1994 | Ordoukhanian | |
| 5,331,820 A | 7/1994 | Faries, Jr. et al. | |
| 5,333,326 A | 8/1994 | Faries, Jr. et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,457,962 A | 10/1995 | Faries, Jr. et al. | |
| 5,502,980 A | 4/1996 | Faries, Jr. et al. | |
| 5,522,095 A | 6/1996 | Faries, Jr. et al. | |
| 5,524,643 A | 6/1996 | Faries, Jr. et al. | |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,862,672 A | 1/1999 | Faries, Jr. et al. | |
| 5,879,621 A | 3/1999 | Faries, Jr. et al. | |
| 5,950,438 A | 9/1999 | Faries, Jr. et al. | |
| 6,003,328 A | 12/1999 | Faries, Jr. et al. | |
| 6,035,855 A | 3/2000 | Faries, Jr. et al. | |
| 6,087,636 A | 7/2000 | Faries, Jr. et al. | |
| 6,091,058 A | 7/2000 | Faries, Jr. et al. | |
| 6,148,634 A | 11/2000 | Sherwood | |
| 6,255,627 B1 | 7/2001 | Faries, Jr. et al. | |
| 6,371,121 B1 | 4/2002 | Faries, Jr. et al. | |
| 6,802,802 B2 | 10/2004 | Woog | |
| 6,810,881 B2 | 11/2004 | Faries, Jr. et al. | |
| 6,860,271 B2 | 3/2005 | Faries, Jr. et al. | |
| 6,910,485 B2 | 6/2005 | Faries, Jr. et al. | |
| 6,910,801 B2 | 6/2005 | Sasaki | |
| 6,918,395 B2 | 7/2005 | Faries, Jr. et al. | |
| 7,176,030 B2 | 2/2007 | Faries, Jr. et al. | |
| 7,269,970 B2 | 9/2007 | Robertson | |
| 7,347,210 B2 | 3/2008 | Faries, Jr. et al. | |
| 7,350,373 B1 | 4/2008 | Faries, Jr. et al. | |
| 7,389,653 B2 | 6/2008 | Kasza et al. | |
| 7,418,966 B2 | 9/2008 | Faries, Jr. et al. | |
| 7,419,070 B2 | 9/2008 | Cantwell et al. | |
| 7,874,167 B2 * | 1/2011 | Kammer ............... A61F 7/0085 366/209 |
| 8,057,092 B2 | 11/2011 | Ryan et al. | |
| 8,148,666 B2 | 4/2012 | Faries, Jr. et al. | |
| 8,348,186 B2 | 1/2013 | Seidler et al. | |
| 2003/0161912 A1 * | 8/2003 | Zeng ........................ A23L 2/00 426/87 |
| 2005/0247169 A1 | 11/2005 | Faries, Jr. et al. | |
| 2006/0194324 A1 | 8/2006 | Faries et al. | |
| 2006/0260443 A1 | 11/2006 | Faries et al. | |
| 2008/0017292 A1 | 1/2008 | Gammons et al. | |
| 2010/0293965 A1 * | 11/2010 | Frank ..................... A23G 9/045 62/1 |
| 2014/0226434 A1 | 8/2014 | Gammons | |

OTHER PUBLICATIONS

Surgislush TM, Web Page originally located as www.cchangesurgical.com/surgislush.html but obtained from Archive.Org via https://web.archive.org/web/20130727030003/http://www.cchangesurgical.com/surgislush.html. indicating a capture date of Jul. 27, 2013 but believed to represent material posted in 2012. 2 pages of screen shots. Published originally by C Change Surgical of Winston-Salem, North Carolina.

Recent Press Releases, web page obtained from Archive.Org when selecting the "Recent Press Releases" option on Archive.Org web page located at https://web.archive.org/web/20130727030003/http://www.cchangesurgical.com/surgislush.html, the Archive.Org URL for the press releases located at https://web.archive.org/web/20130907053017/http://cchangesurgical.com/press.html and indicating a collection date of Sep. 7, 2013 from location http://cchangesurgical.com/press.html., 9 Pages. Published originally by C Change Surgical of Winston-Salem, North Carolina.

SurgiSlush TM Set-Up and Start, web page obtained from Archive.Org when selecting Click Here to see a video demonstration of the SurgiSlush TM Surgical Slush Freezer, Archive.Org URL https://web.archive.org/web/20130804175130/http://vimeo.com/42583184 indicating content obtained Aug. 4, 2013 from http://vimeo.com/42583184, but link to video is no longer active. 4 pages, Published originally by C Change Surgical of Winston-Salem, North Carolina.

Screenshots taken of video previously posted at http://vimeo.com/42583184 somtime in 2012, screen shots obtained Apr. 26, 2016 for purposes of this Information Disclosure Statement, 51 screen shots of a 37 second video clip showing a slush making machine that receives a square bottle of sterile saline into a carriage and rotates the carriage and bottle together approximately 90 degrees counter-clockwise before snapping back to the original position and repeating. Video created for C Change Surgical of Winston Salem.

Physical disc of the video posted at http://vimeo.com/42583184 sometime in 2012 and used to create the series of 51 screen shots.

* cited by examiner

300

440

440

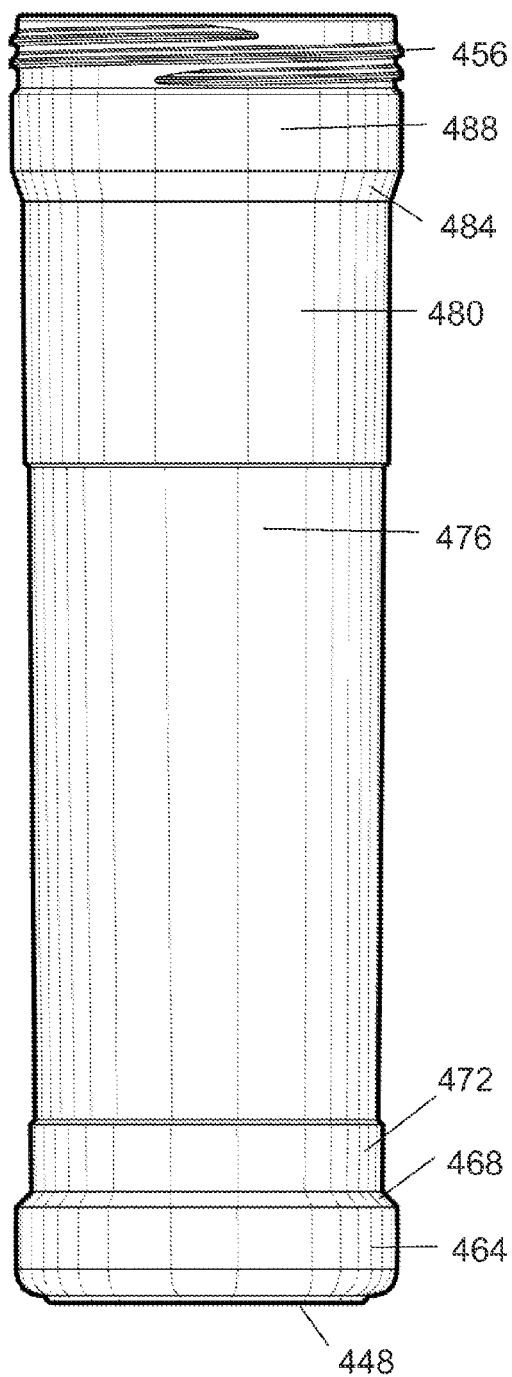
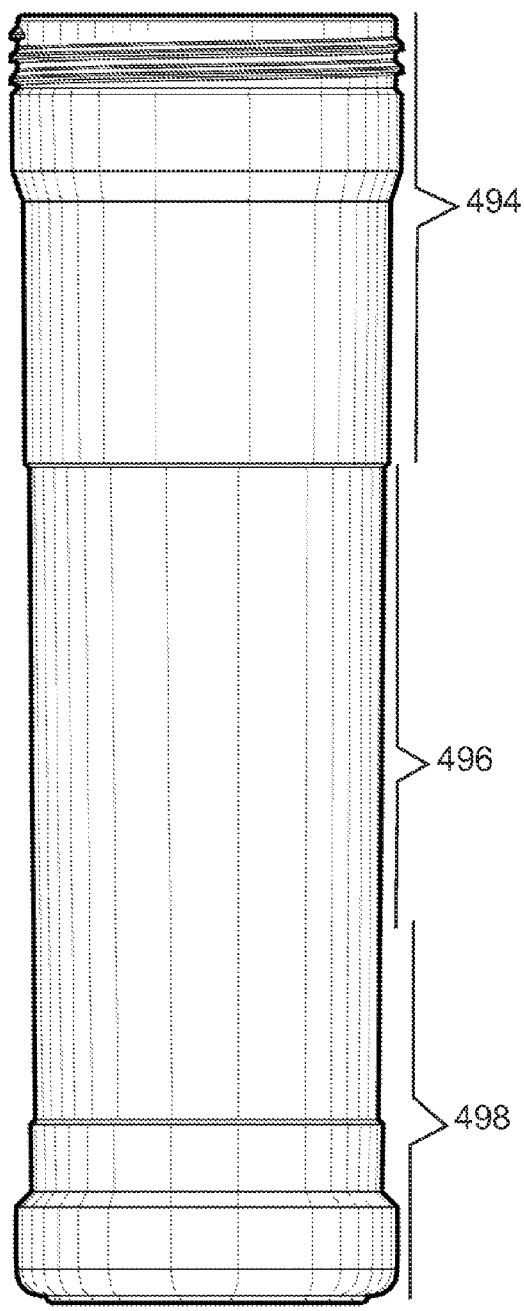

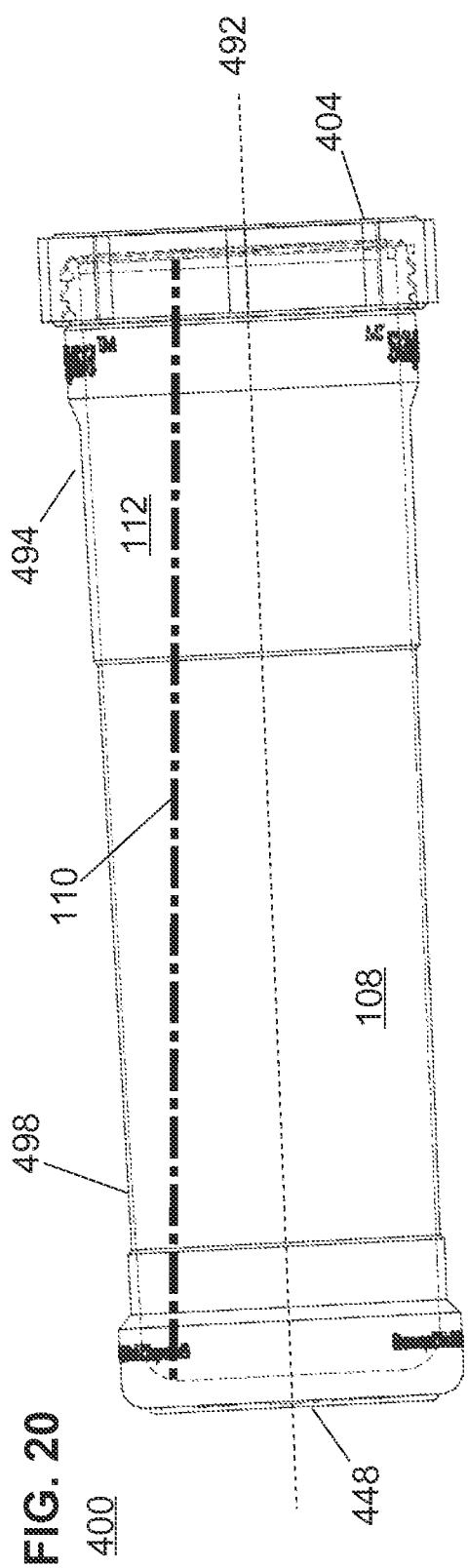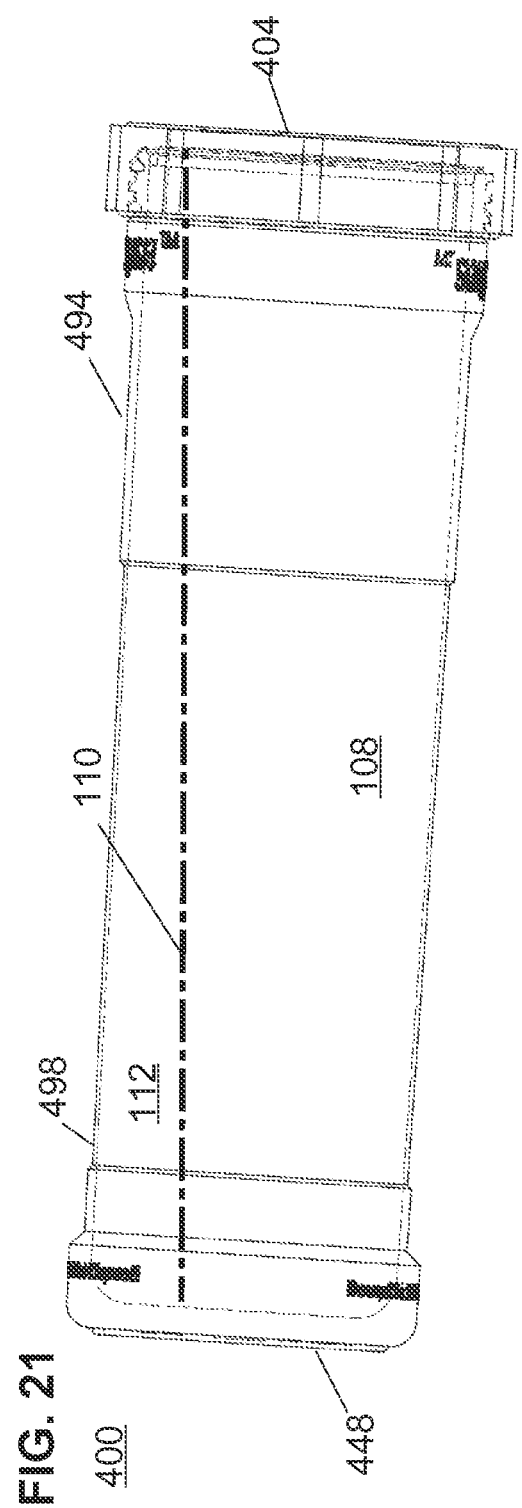

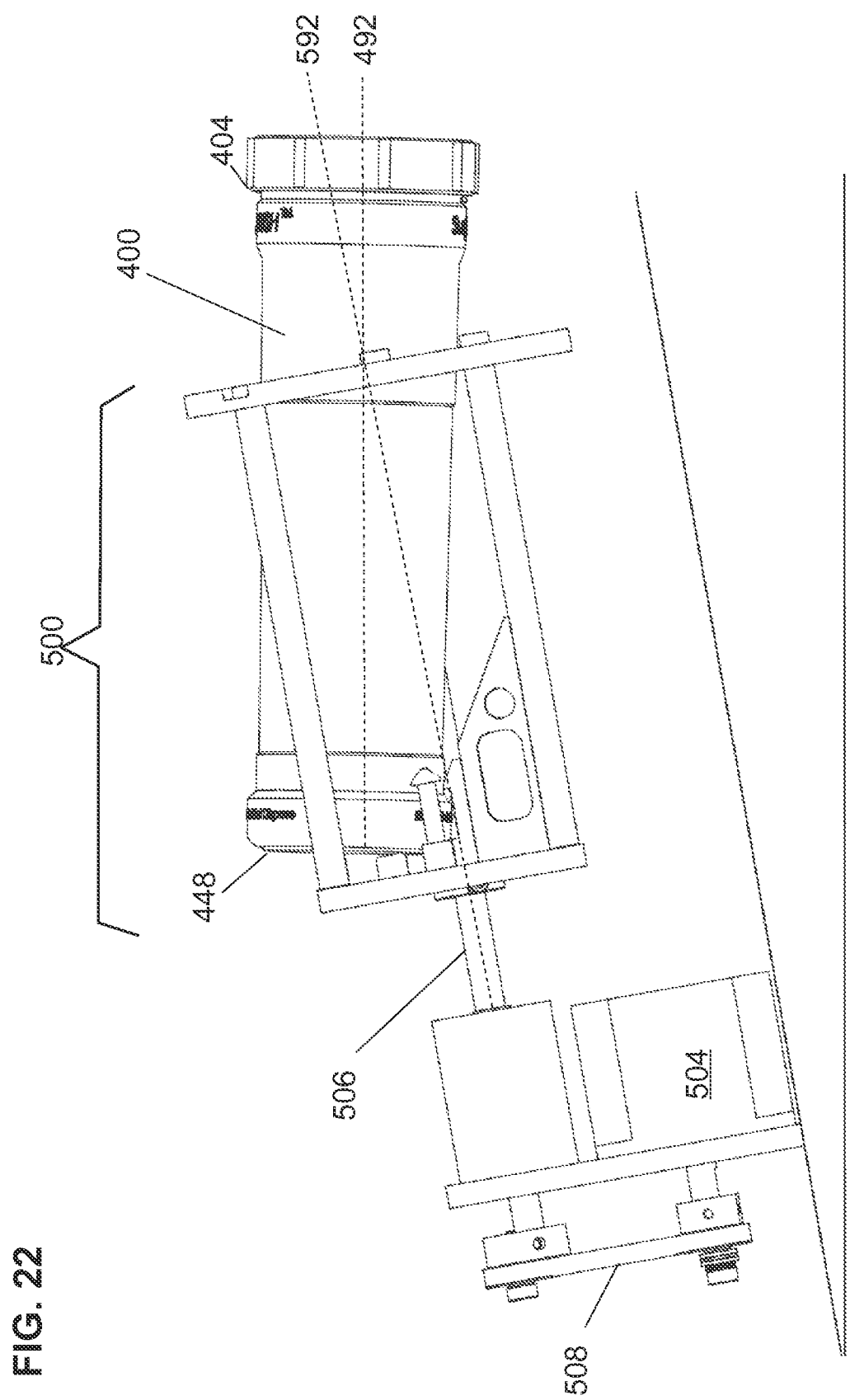

FIG. 55 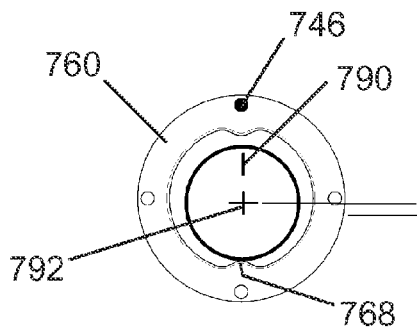 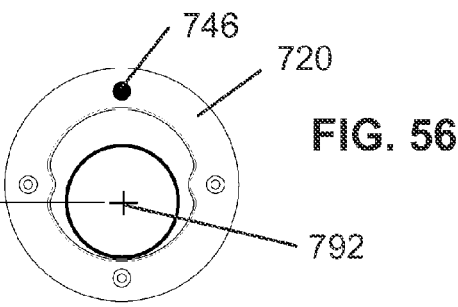 FIG. 56
FIG. 57 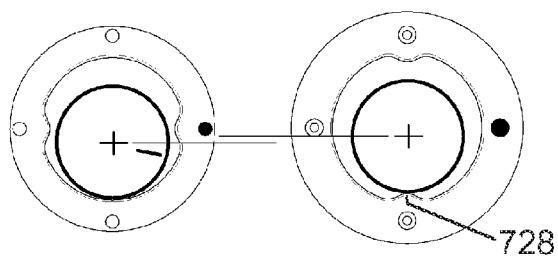 FIG. 58
FIG. 59 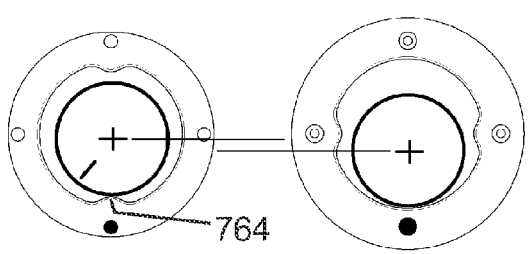 FIG. 60
FIG. 61 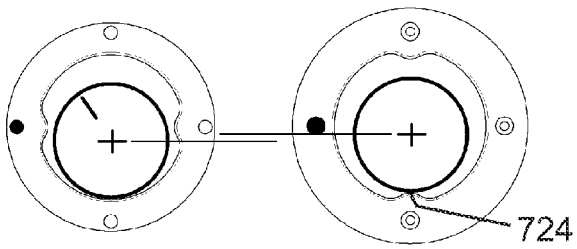 FIG. 62
FIG. 63 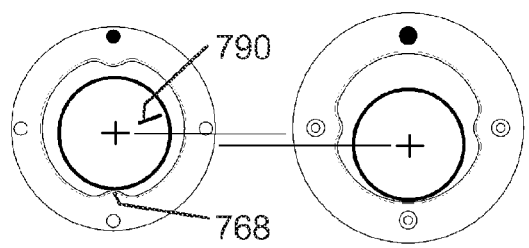 FIG. 64

PRODUCTION OF WELL-MIXED SURGICAL SLUSH

This application incorporates by reference and claims the benefit of U.S. Provisional Application No. 62/085,590 filed Nov. 30, 2014 for Production of Well-Mixed Surgical Slush via Eccentric Oscillation.

BACKGROUND

Field of the Disclosure

This disclosure relates generally to the production of sterile therapeutic medium such as sterile surgical slush for use in surgery. More particularly, this disclosure is related to the mixing of surgical slush while the saline and surgical slush are being chilled to provide a slush slurry with desirable mechanical properties.

Sterile saline slush is used in a variety of surgical applications to slow organ and tissue metabolic rates thereby protecting organs from irreversible tissue damage during cardiac, neurological organ transplant, vascular, urologic and other complex surgeries. It is important that the slush has as smooth and spherical a configuration as possible to ensure atraumatic slush without sharp crystal edges that could puncture or damage tissue. The slush should have a substantially uniform consistency to maintain optimal thermodynamic cooling performance Surgical slush is a mix of ice crystals formed while cooling saline and some amount of liquid saline that remains in liquid form.

Commonly assigned U.S. Pat. No. 7,874,167 for Method and Apparatus for Producing Slush for Surgical Use taught a process for making slush where sterile saline was placed in a sterile interior of a container with a lid that engaged threads on the outer walls of the container. The container was only partially filled with sterile saline so that slush could tumble as described below. The container was placed in a portion of a slush chilling device with the top of the container not over the bottom of the container (horizontal or inclined, but not vertical). As the container was chilled, the container was rotated at a constant speed. Agitation features extending inward from at least the outer walls worked to lift slush out of the slush slurry and then drop the slush to fall down into the slush slurry. This constant mechanical agitation while the slush slurry slowly converted from no ice to predominantly small crystals of sterile surgical slush produced a slush with desirable mechanical properties in that the ice crystals were small rather than large.

Desirable surgical slush has a substantially uniform consistency. Desirable surgical slush will feel soft to the touch without any hard crystalline formations. Thus, the ice crystals created for use in a snow cone would not be acceptable and that sort of consistency is to be avoided through controlling the slush creation process.

It is desirable to avoid introducing blades into the sterile container to mix the slush as the blades introduce additional vectors for the introduction of contamination to the sterile material.

While there are many methods for providing some level of mixing to a liquid to achieve substantial uniformity between a chilled temperature of the outer wall of a container holding the liquid and the liquid contents, achieving a well-mixed slush slurry is substantially more difficult as the semi-solid slush slurry does not behave like a liquid.

Mechanical agitation as the slush is being created allows small crystal formations to be formed at the nucleation sites, but size growth of the crystal formations is inhibited because mechanical agitation prevents larger crystal growth. When these small crystals are suspended in the bulk fluid, they form a slurry or slush. Mechanical agitation also helps keep the bulk fluid temperature more consistent and helps reduced large crystal growth that would otherwise occur at the fluid boundary (such as the fluid/air boundary or at any of the container walls) where heat is typically being transferred out of the fluid.

More Detailed Examination of Slush Formation.

As energy is removed from a liquid, the temperature continues to fall until the temperature reaches point at which crystal formation begins. Crystallization can be broken down into two parts, nucleation and crystal growth. Nucleation occurs when molecules start to arrange into a defined crystal structure. Crystal growth occurs on the nucleus crystal formed during nucleation.

During nucleation, an interface is formed at the boundary between the solid and liquid phases of water. Creation of this boundary is actually an exothermic process which means that heat and pressure are released. In order for a stable nucleus to form, the fluid temperature must be sufficiently below the melting point of the fluid (super cooled) to absorb the energy release during nucleation without causing the temperature to rise above the melting point. The amount of super cooling needed to initiate nucleation depends on whether or not there are nucleators in the fluid.

Nucleators are things like impurities, undissolved solids, and irregularities on the container walls. Without nucleators, the fluid goes through homogeneous nucleation and requires significant super cooling because of the large amount of energy required to form a crystalline surface boundary where no boundary previously existed. When nucleators are present the fluid goes through heterogeneous nucleation and a stable nucleus can be formed at the site of the nucleator with temperatures just slightly below the melting point.

The crystal growth part of freezing is also an exothermic process. As long as the heat produced by crystal growth is removed, the freezing process will continue. If the fluid is sufficiently super cooled before any nucleation occurs, the initial crystal growth can be very fast. For instance, a water bottle that is super cooled to −20 degrees Celsius before nucleation can have about 25% of the fluid turn to ice in about two or three seconds when something happens to initiate freezing. The trigger to initiate freezing may be the addition of an impurity. Another possible trigger to initiate freezing is bumping the bottle on a table such that a pressure wave propagates through the liquid.

Only 25% of the fluid will go through the phase change because the latent heat of freezing is about 80 cal/gm and the specific heat of water is about 1 calorie per degree Celsius per gram. This means the freezing process produces enough heat to raise the temperature of one gram of water by 80 Celsius, but since the water was only 20 degrees Celsius below the melting point the freezing could only occur in 20/80=25% of the fluid. In this example the liquid temperature quickly rises from −20 degrees Celsius to 0 degrees Celsius. After this initial freezing the crystal growth continues more slowly and is limited by how fast heat can be removed from the water.

If pure water is sufficiently mixed during the phase change process, the temperature of the pure water will remain at the melting point. As heat is removed which tends to reduce the temperature below the melting point, energy is available for the crystals to grow, but the crystals can only grow until the heat generated by their growth brings the temperature back up to the melting point. This balancing act between heat removal and crystal growth continues until all the liquid is frozen at which point the temperature of the ice starts to drop. If temperature variations occur within the fluid, then localized areas of freezing can occur that produce hard ice while other parts of the fluid are still completely liquid. This occurs most often at the walls of a container where heat is being removed or at the surface of a body of water like a pond that is exposed to sub-freezing temperatures.

Sterile saline slush may be made from a fluid solution that includes sodium chloride (NaCl) in water which is typically 0.9% sodium chloride by weight. The sodium chloride helps suppress the initial freezing point of the fluid to about −3.3 degrees Celsius. However, since the sodium chloride molecule is not integrated into a water crystalline structure, the concentration of sodium chloride in liquid water goes up as the percentage of water ice goes up. This increasing concentration of sodium chloride that is pushed ahead of the advancing ice causes a further reduction in the freezing point of the remaining fluid. As long as the sodium chloride molecules stay mobile and do not get trapped by a surrounding water crystal structure, the sodium chloride concentration in the remaining liquid can continue to increase and thus decrease the freezing point until about −21.1 degrees Celsius which is the temperature at which salt begins to crystallize out of solution.

Slush is essentially a collection of ice crystals surrounded by liquid. The microscopic structure and size of the ice crystals have a large impact on the macroscopic feel and appearance of the slush. A soft slush is made up of many small crystals while a slush with fewer but larger crystals will appear more granular and would have small shards of ice. Keeping the increasing sodium chloride concentration homogenous throughout the container while controlled crystal growth is occurring tends to promote the formation of many small ice crystals rather than fewer large ice crystals. Keeping the temperature of the solution homogenous is also important. Failure to maintain substantially homogenous temperature distribution leads to localized cool spots which may lead to bridges between clumps of crystals that are not easily broken as the bridges may grow extensively as the localized cool spot allows for relatively rapid freezing.

One of the most difficult areas to prevent large crystalline formation is at the container wall. Heat transfer occurs at the surface so any ice crystal that contacts the wall immediately has access to the cooling needed for rapid growth because the wall temperature will be well below the freezing point. If however, the contact between the ice crystal and wall is brief, the quickly grown extension to the crystalline lattice is weak and can be broken when brought back into the warmer bulk fluid. The problem with rapid crystal formation at the wall is compounded as a crystal requires less energy to form a new surface between the liquid and solid phase if the crystal forms on an already existing surface.

This heterogeneous nucleation at the wall can also be accelerated if there are pits or cracks in the surface of the wall. Ice crystals form faster if the contact angle between the wall and a fluid droplet is decreased in that there is more contact with the chilled wall.

Appropriate choices for container geometry and complex mixing motion promote proper slush formation that reduces crystal contact time with the container wall and maintains a homogeneous sodium chloride concentration and temperature throughout the container. Establishing the desired mixing while the saline is still a liquid is relatively easy as the mobility of the fluid allows for easy transfer throughout a container. However, once a portion of the saline turns to slush, proper mixing becomes progressively more difficult because the slush viscosity is constantly changing as the crystal concentration increases.

SUMMARY OF THE DISCLOSURE

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

One summary of some of the teachings in the present disclosure is as follows. A method of making sterile slush that starts with partially filling a sterile slush container with sterile liquid to be made into surgical slush. Placing a sterile removable lid on the slush container so that the closed slush container has the sterile liquid and a substantial amount of air so the closed slush container has a substantial air gap. The ratio of liquid to air may be in the nominal range of four to one.

The slush container has smooth interior walls that are hydrophobic. While the slush container does not have to be cylindrical, the slush container needs to be free of sharp corners or other locations where slush may adhere. Placing the slush container in a carriage within a cooled chamber.

Moving the carriage to impart a sequence of accelerations to the contents of the slush container to cause the contents to move relative to the walls and lid of the container. This complex movement (something other than staying still or pure uniform rotation about the longitudinal centerline of the container) helps keep slush well mixed within the closed slush container. The slush container may be oriented with the longitudinal centerline close to horizontal so that movements of the top of the container relative to the bottom of the container promote movement of the air gap in the container from the one end of the container to the other end of the container to help keep slush from adhering to the interior walls of the container. Applying a cycle of agitation that rotates the slush container so that the start position of the container from one cycle of agitation to the next cycle of agitation exposes different portions of the slush container interior to the air gap as movement into and out of the air gap helps remove ice crystals from the interior walls.

Keeping the contents of the slush container agitated and mixed so that the slush is distributed substantially evenly throughout the slush container avoids creation of large slush ice structures. Atraumatic slush that is desirable for use in surgical procedures may be produced with this process.

The complex motion of the slush saline mixture at the air gap may be produced by a range of different types of stimulus. Examples provided within this disclosure include asymmetric rotation reversals where rotation of around a longitudinal axis if rotation proceeds for less than one full rotation before a reversal for less than one full rotation. Another type of stimulus provides for rotation around a longitudinal axis of the slush container for many revolutions without changing direction. Stimulus includes periodically dropping one or both ends of the slush container and lifting the slush container. The lifting and dropping may be implemented with humps or troughs on a rotating carriage that contains the slush container. Other forms of stimulus to lift and drop one or both ends of the slush container are disclosed.

Another way to look at the teachings of the present disclosure is to focus on the method for removing ice from a set of interior walls within an interior of a closed slush container while chilling contents of the closed slush container to make surgical slush. This method includes partially filling a slush container with liquid saline and closing the slush container by putting a removable lid on a top end of the slush container to form the closed slush container with contents of liquid saline and a substantial air gap. The closed slush container having the set of interior walls including a bottom end of the closed slush container and a bottom end of the removable lid that are smooth and hydrophobic to resist adherence of ice crystals to the set of interior walls as cooling is applied to an exterior of the closed slush container.

One method includes moving the closed slush container in a sequence of repeated cycles of complex movements. Each cycle of complex movements including rotating the closed slushed container in a first rotational direction around an axis of rotation of the closed slush container and in a second rotational direction, opposite to the first rotational direction so that asymmetric rotation reversals cause the contents of the closed slush container to move from a first starting point before one cycle of complex movements to a second starting point, different from the first starting point, before a start of a second cycle of complex movements. Those of skill in the art will appreciate that the axis of rotation for rotation in the first rotational direction may be different from the axis of rotation for rotation in the second rotational direction if the position of the closed slush container changes between the first set of rotations and the second set of rotations. Those of skill in the art will appreciate that there may be additional movements of the closed slush container in addition to the sequence of repeated cycles of complex movements, for example some initial movements of the closed slush container at the start of the cooling process or at the end of the cooling process.

The method may include varying a slope of a longitudinal centerline of the closed slush container to cause movement of an air bubble within the closed slush container so that at least a portion of the bottom end of the closed slush container enters and leaves the air gap and at least a portion of the bottom end of the removable lid enters and leaves the air gap to help remove ice crystals from the interior walls of the closed slush container. The method may be adapted for use with legacy equipment to promote movement of the air gap towards the bottom end surface of the slush container and towards the top end surface of the slush container but not necessarily reaching the bottom end surface and the top end surface.

Yet another way to look at some of the teachings of the present disclosure is to focus on a method of making surgical slush within a closed slush container as an exterior of the closed slush container is cooled to convert liquid saline to surgical slush comprising a mixture of ice crystals and liquid saline. This method includes partially filling a slush container so that the slush container is not full of saline liquid so that the slush container is filled by a combination of air and non-air contents. The non-air contents are initially all liquid saline but over time become a mix of liquid saline and ice crystals. Placing a removable lid on the slush container to form the closed slush container having a set of interior surfaces that are smooth and hydrophobic to resist adherence of ice crystals.

Causing air within the closed slush container to move within the closed slush container to change what portion of a bottom interior of the closed slush container is exposed to the air gap, to change what portion of a bottom of the removable lid is exposed to the air gap; and to change what portion of the closed slush container between the bottom interior and the bottom of the removable lid is exposed to the air gap.

The movement of air within the closed slush container is accompanied by a sequence of accelerations of non-air contents of the closed slush container so that the closed slush container moves over time so that different portions of the set of interior surfaces enter and leave the air gap to help keep ice crystals from adhering to the set of interior surfaces.

Optionally, slush may be delivered from a slush container to a target container (such as a basin) within a sterile field with several deliveries of portions of the contents of the slush container by squeezing the walls of the open slush container to preclude all of the slush from moving at once through the wide, open mouth of the slush container.

Yet another way to look at some of the teachings of the present disclosure is to focus on a slush container for use in making surgical slush. The slush container having a bottom, a tapered cylindrical sidewall, and a top end with an opening that may be sealed with a removable lid. The combination of the bottom, the tapered cylindrical sidewall, the top end, and a bottom side of the removable lid forming a closed interior having surfaces that are smooth and hydrophobic to resist adherence of ice crystals to the closed interior of the closed slush container. The bottle adapted to allow an observer to look through at least a portion of the tapered sidewall to view the location of a clump of surgical slush and to allow a user to use one gloved hand to squeeze the tapered sidewall to hold at least a portion of the surgical slush to prevent the held portion from leaving through an open top end. The hydrophobic interior of the slush container may be a coating or may be the material used to make the slush container. The slush container may have thicker walls at some sections than other sections to improve the ability of the slush container to withstand the wear from movements within the carriage while allowing thin wall sections not subject to wear to be more conducive to heat transfer to promote chilling of the contents of the slush container.

Aspects of the disclosure address the use of a high volume slush freezer that has a single motor drive more than one carriage, each carriage containing at least one slush container.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

Note—as the process described in this application changes sterile saline 108 to a slurry of slush mixed with a small amount of liquid saline 108, the element number 108 is used for the saline without any slush,
the final slush slurry with small amounts of saline; and
the intermediate states with some slush but not yet the final slush slurry.

Figure 1:
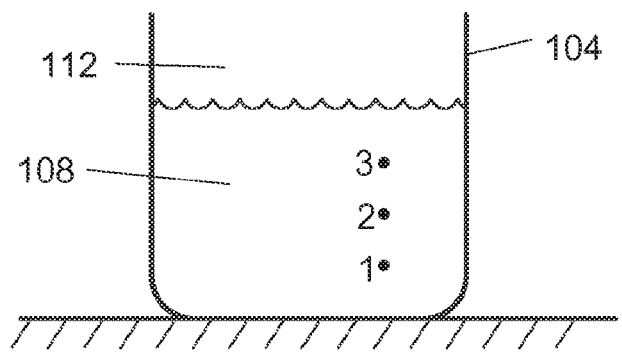

The difference between saline without any slush and the final slush slurry is a function of time rather than location as the saline will remain in the interior of the container until used. Thus, it would be impractical to have different element numbers for liquid saline and slush. Frequently, from the discussion of the drawing, the state of the saline or slush is made explicit.

FIG. 1 shows a lower portion of a cross section of a container 104 with a substantially rectangular cross section.

Figure 2:
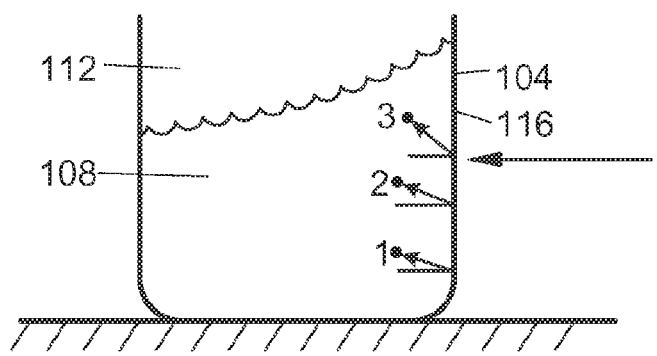

FIG. 2 shows the container 104 from FIG. 1 immediately after the container 104 quickly moved to the left.

Figure 3:
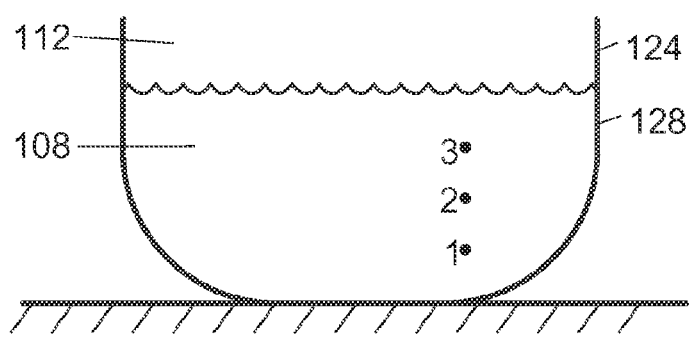

FIG. 3 shows a second container 124 and fluid interaction but with a container wall that is substantially curved.

Figure 4:
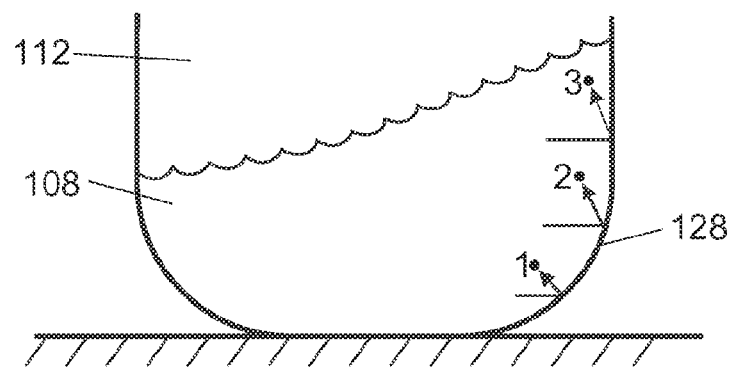

FIG. 4 shows a second container 124 from FIG. 3 immediately after the container is quickly moved to the left.

Figure 5:
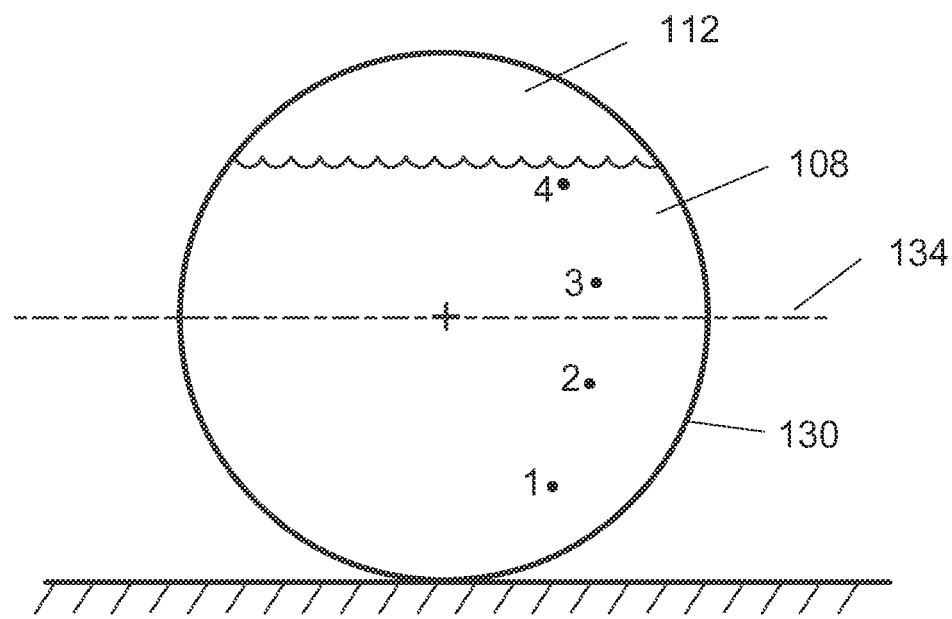

FIG. 5 shows a container 130 with a circular profile that is partially filled with a sterile saline 108 and thus has an air gap 112 above the sterile saline 108.

Figure 6:
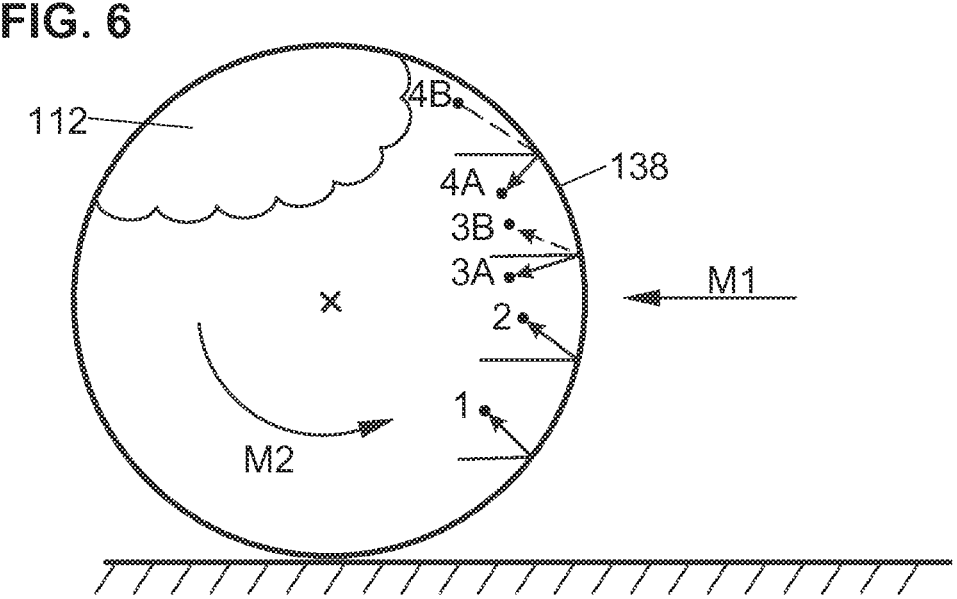

FIG. 6 shows the container 130 from FIG. 5 after the container 130 is rapidly moved to the left.

Figure 7:
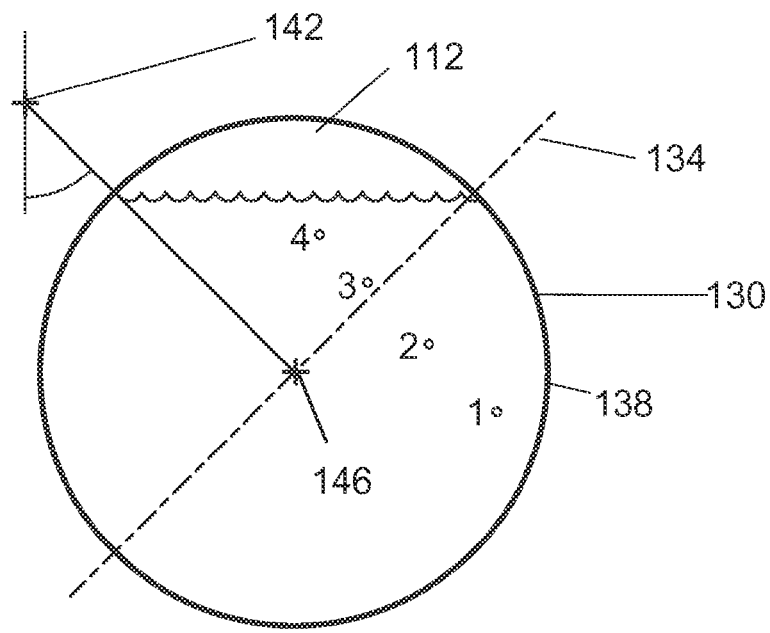

FIG. 7 shows the container 130 previously shown in FIG. 5 and FIG. 6 but instead of the container 130 being displaced in the horizontal plane, the container 130 is forced to follow an arc pattern about a center of rotation 142.

Figure 8:
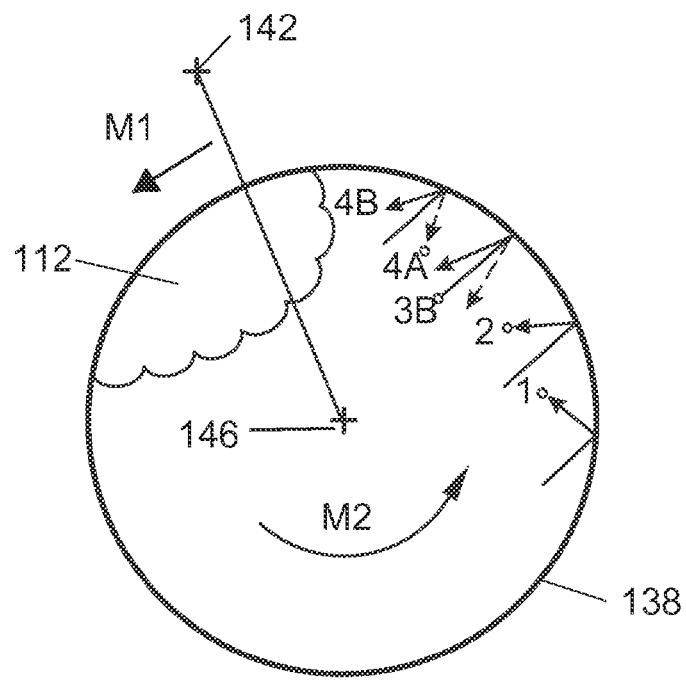

FIG. 8 shows the container 130 from FIG. 7 after the container is rapidly moved to the left.

Figure 9:
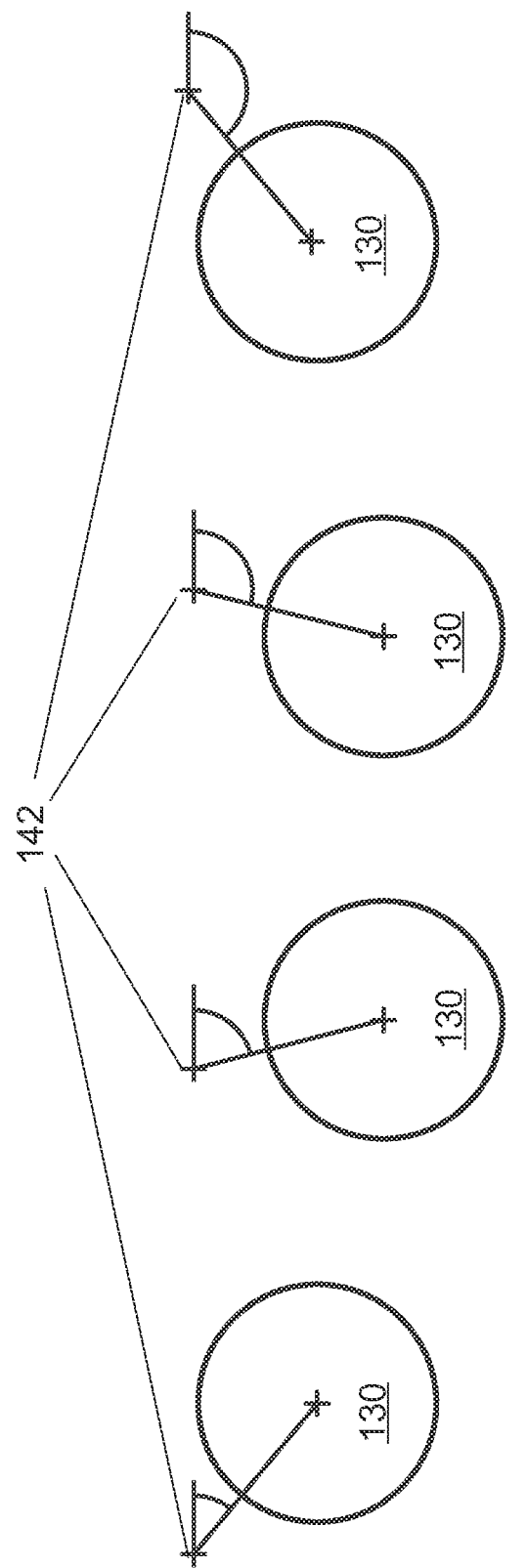

FIG. 9 shows a container 130 swinging about a center of rotation 142 in a sequence of drawings FIG. 9A, FIG. 9B, FIG. 9C, and FIG. 9D.

Figure 10:
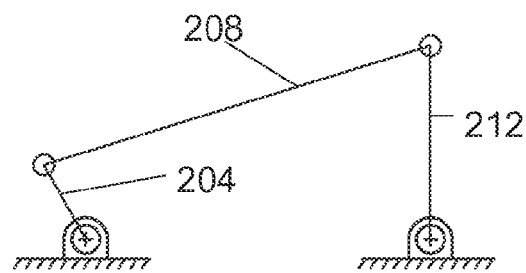

FIG. 10 shows a standard four bar mechanism.

Figure 11:
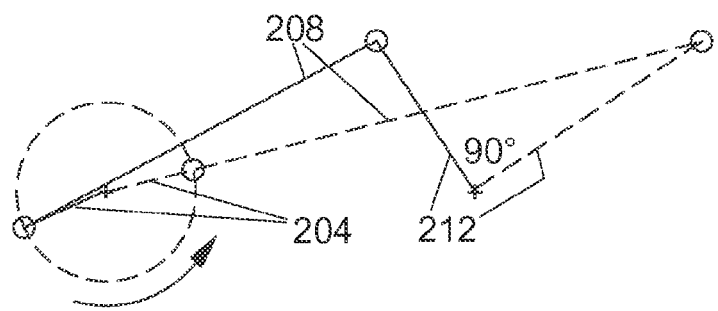

FIG. 11 shows a four bar mechanism with symmetric clockwise and counterclockwise motion.

Figure 12:
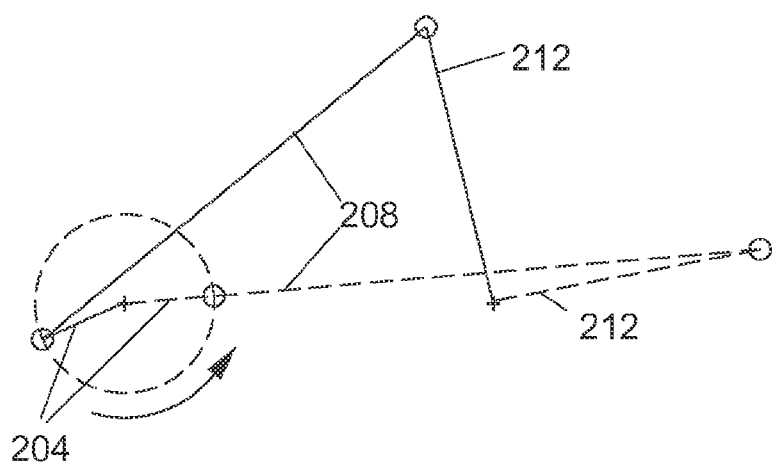

FIG. 12 shows a modified linkage that again produces a 90 degree motion of the rocker arm.

Figure 13:
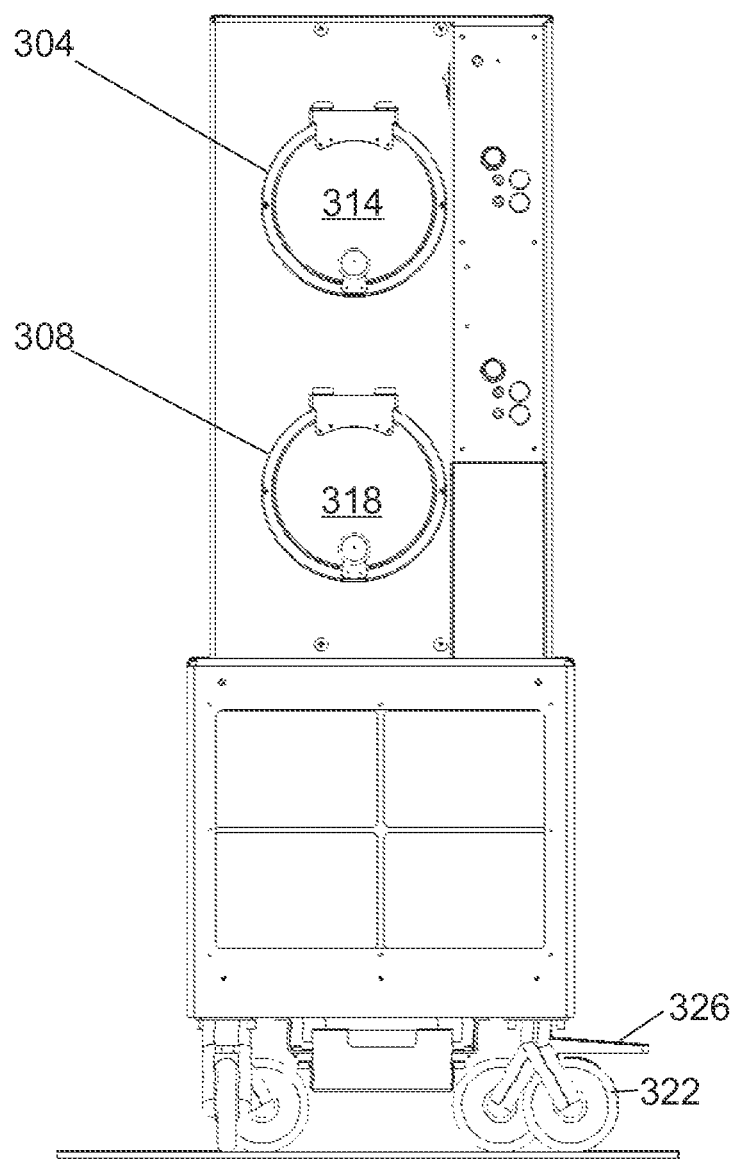

FIG. 13 is a front plan view of a slush freezer 300.

Figure 14:
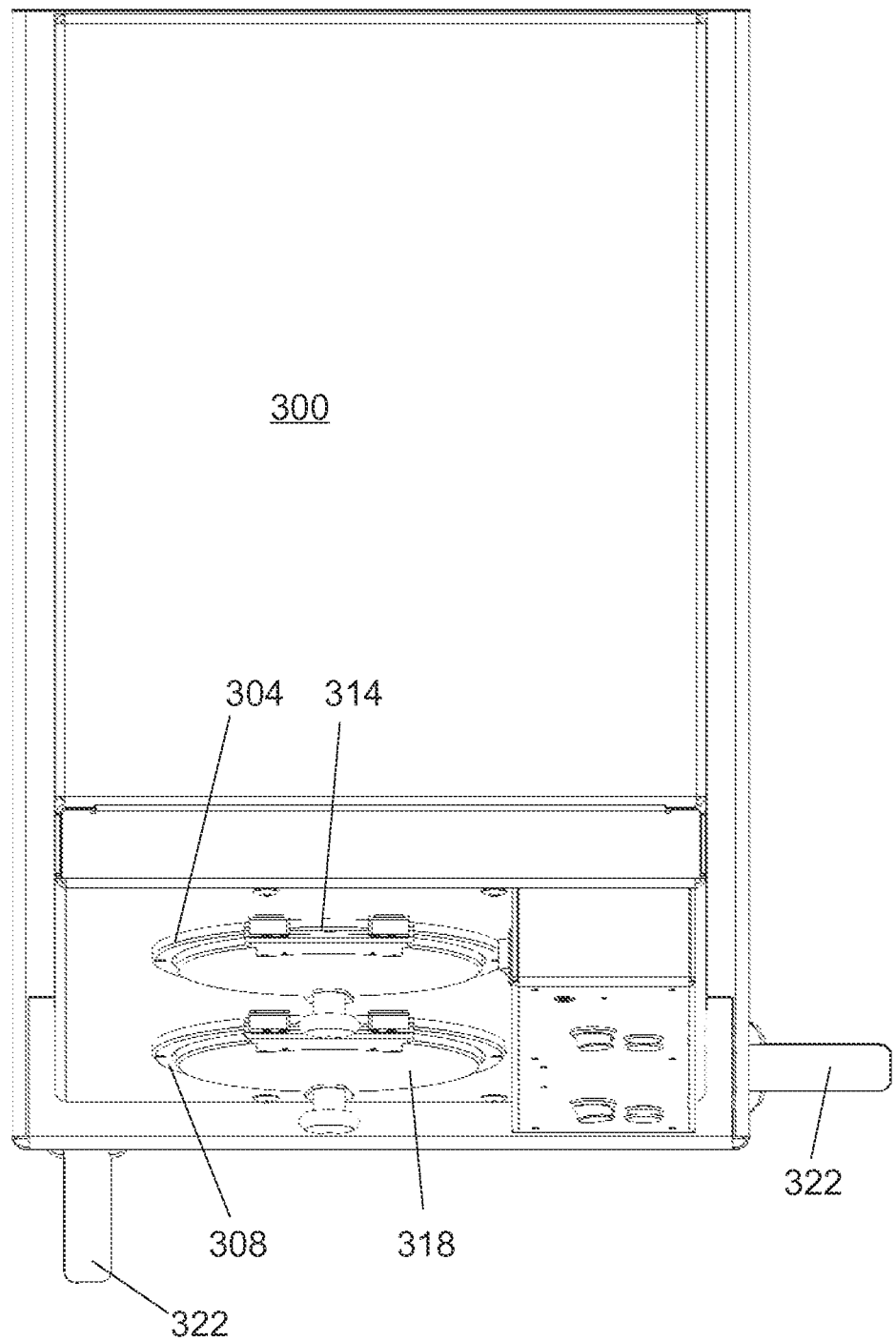

FIG. 14 is a top view of slush freezer 300.

Figure 15:
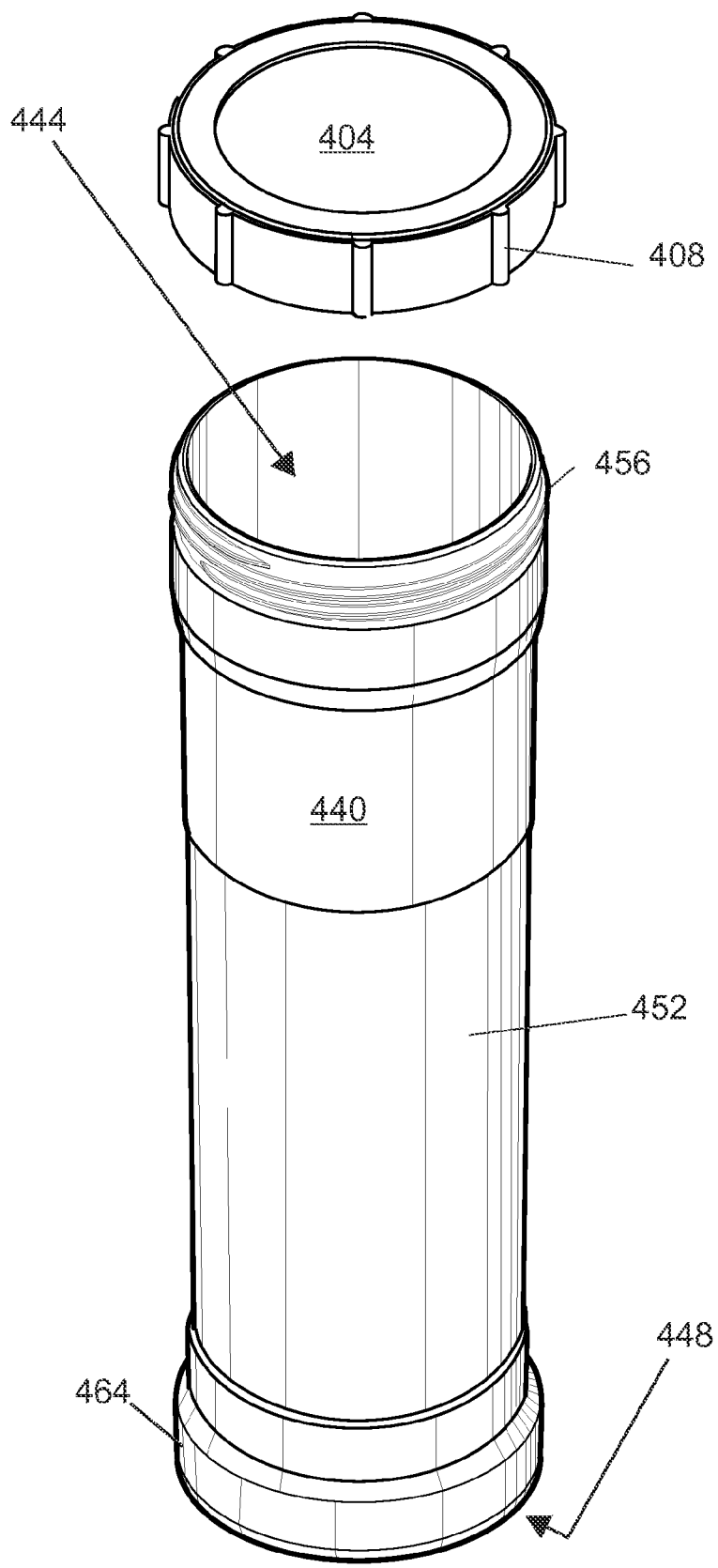

FIG. 15 shows a top perspective view of slush container 400 including lid 404 and slush bottle 440.

Figure 16:
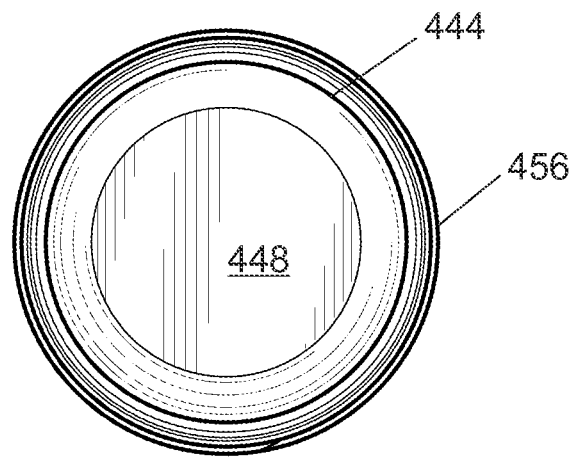

FIG. 16 is a top view of slush bottle 440.

Figure 17:
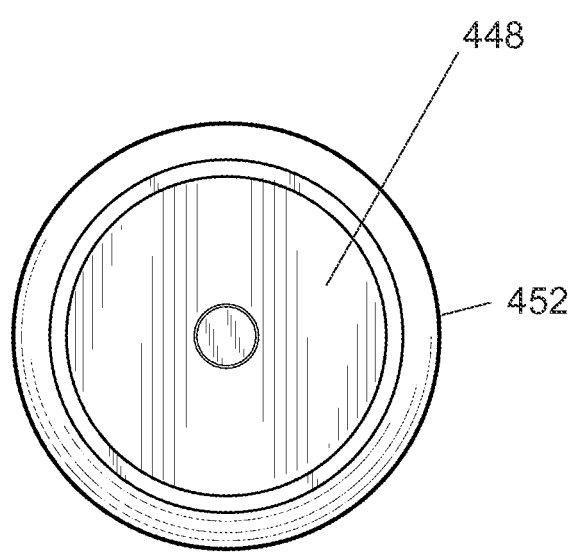

FIG. 17 is a bottom view of slush bottle 440.

FIG. 18 shows a first side view of slush bottle 440.

FIG. 19 shows a second side view of slush bottle 440.

FIG. 20 shows a view of slush container 400 with the saline slush 108 and air gap 112 visible.

FIG. 21 shows another view of slush container 400 with the saline slush 108 and air gap 112 visible.

FIG. 22 shows a side view of a motor 504 and a carriage assembly 500 for receiving a slush container 400.

Figure 23:
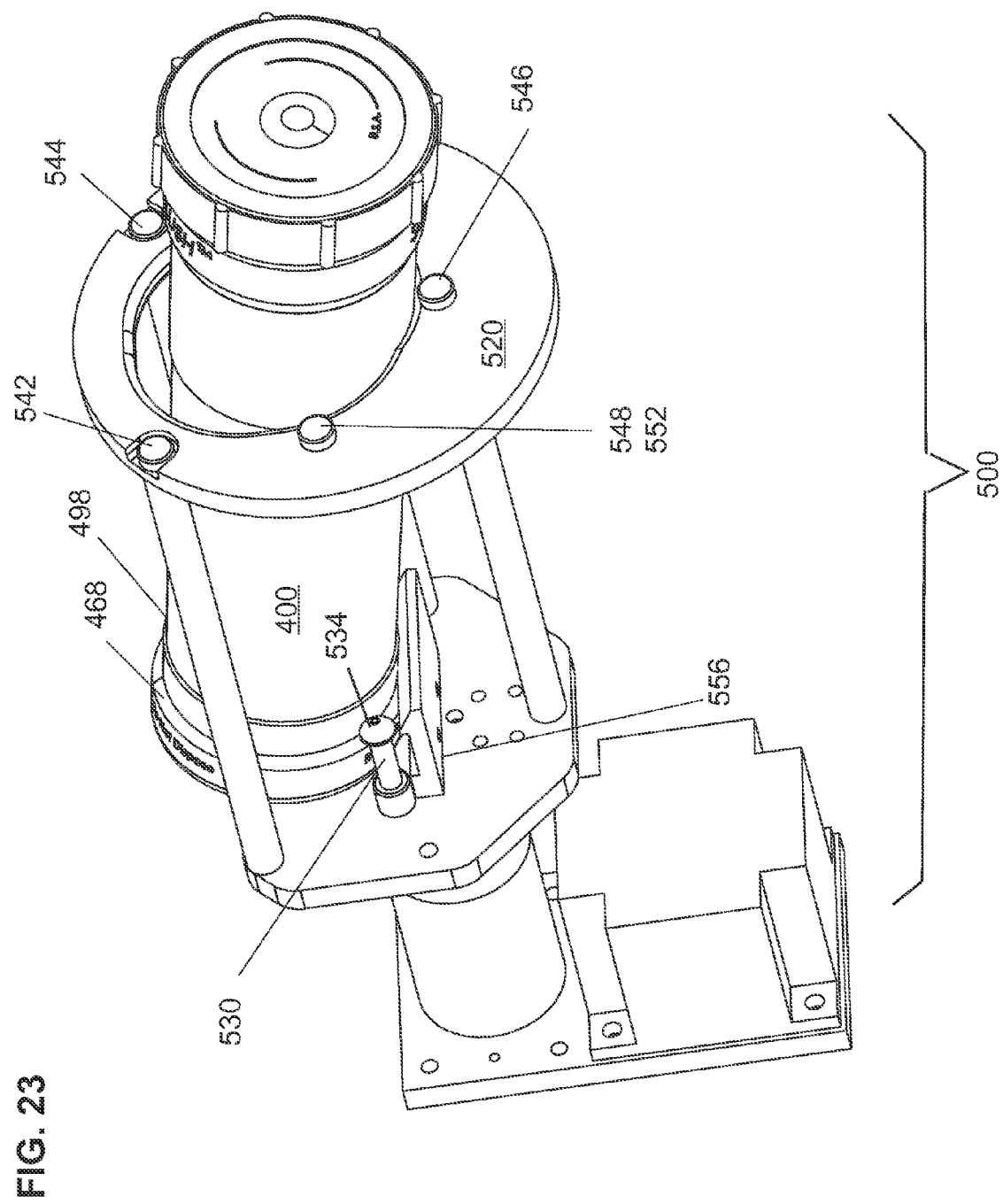

FIG. 23 shows the slush container 400 resting on the support plate 556 in the back and the front plate 520 in the front.

FIG. 24, FIG. 25, FIG. 26, and FIG. 27 show a sequence of movement of the carriage assembly 500 and slush container 400.

Figure 28:
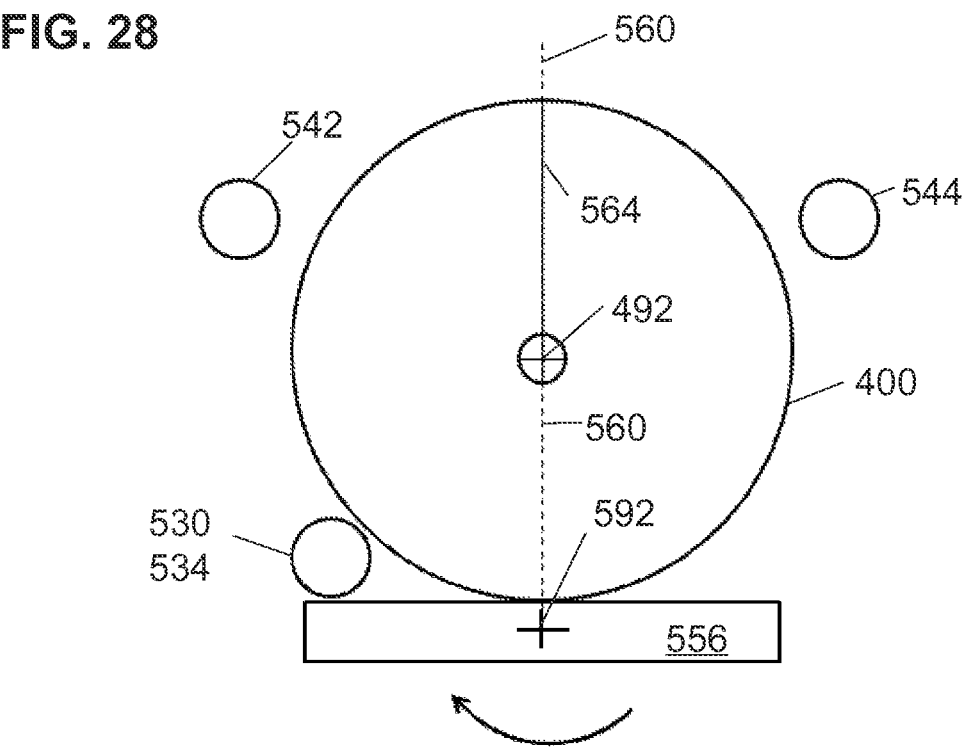

FIG. 28 is a schematic representation of a few select components looking at a cross section of a slush container 400 and carriage assembly 500 taken approximately midway along the slush container 400 and looking towards the back plate 516.

Figure 29:
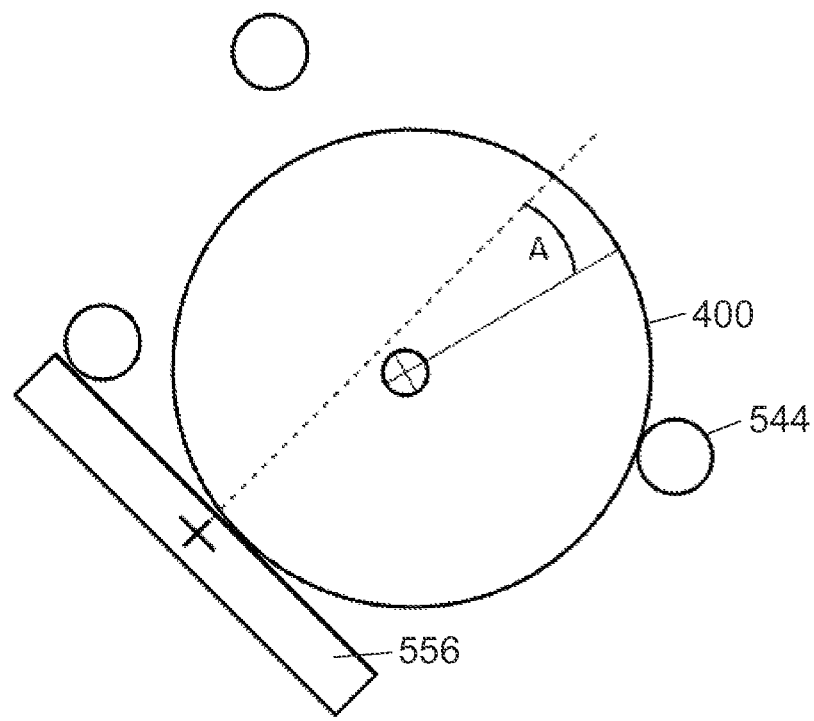

FIG. 29 shows the view from FIG. 28 with the carriage assembly 500 rotated clockwise 45 degrees.

Figure 30:
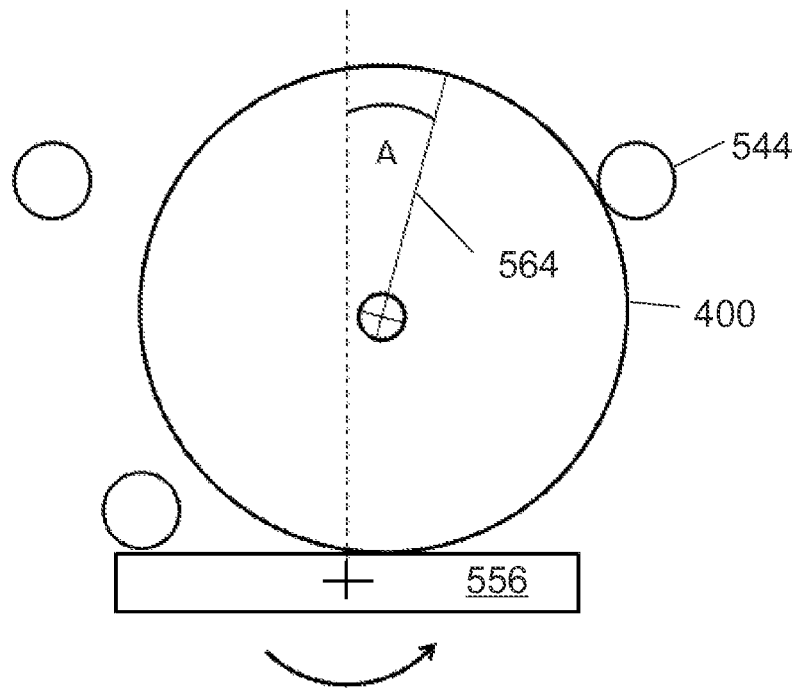

FIG. 30 shows the view from FIG. 28 of the carriage assembly 500 as the carriage assembly 500 rotates counter-clockwise and passes through the position where the support plate 556 is again horizontal.

Figure 31:
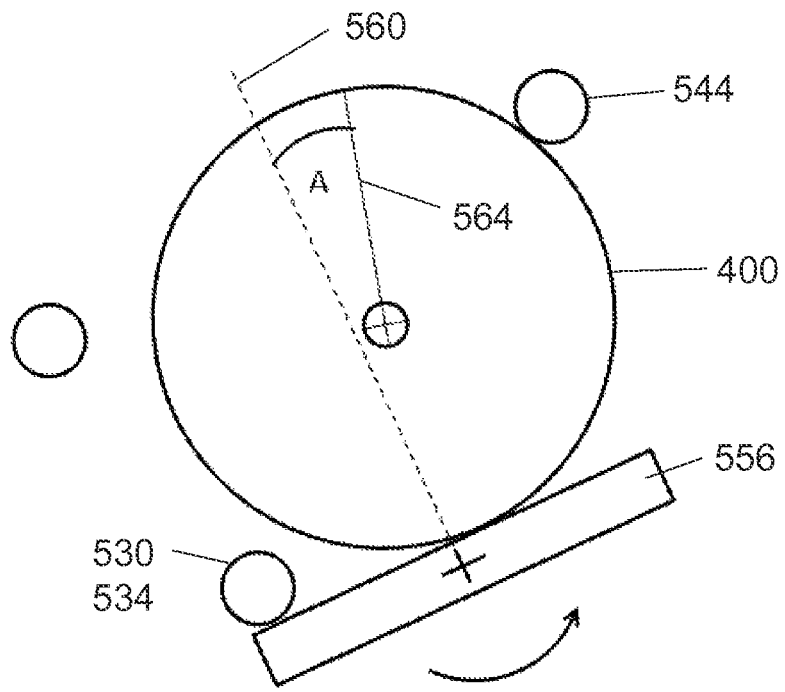

FIG. 31 shows the view from FIG. 28 and shows the continued counterclockwise rotation of the carriage assembly 500.

Figure 32:
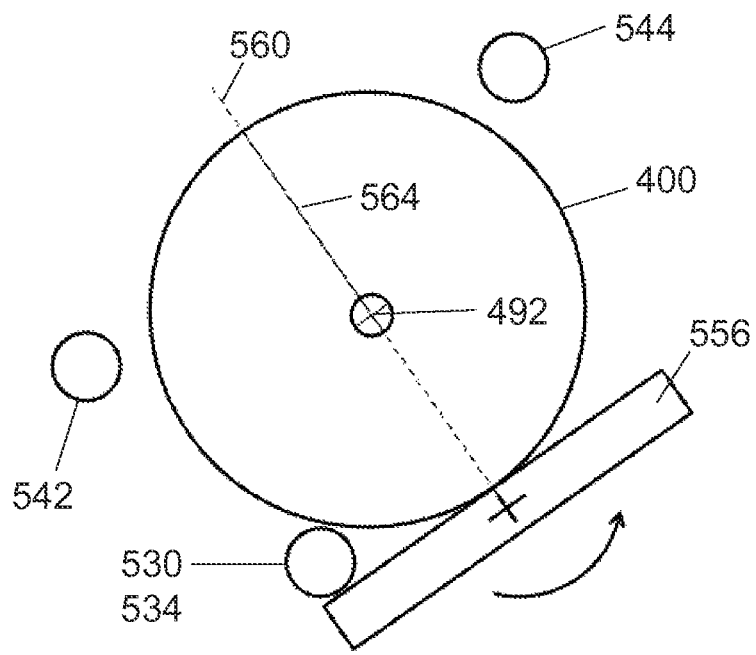

FIG. 32 shows the view from FIG. 28 with slightly more counterclockwise rotation than FIG. 31.

Figure 33:
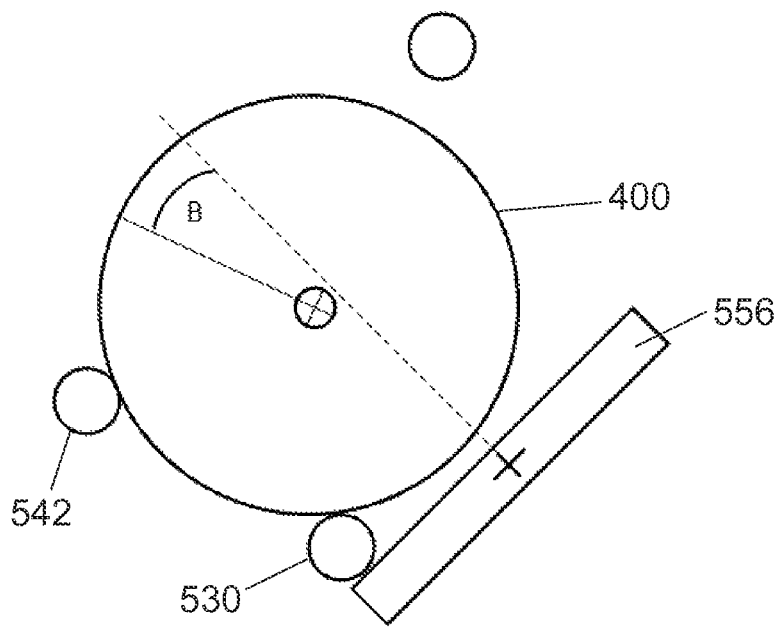

FIG. 33 shows the view from FIG. 28 while the slush container 400 is rotating about short pin 530.

Figure 34:
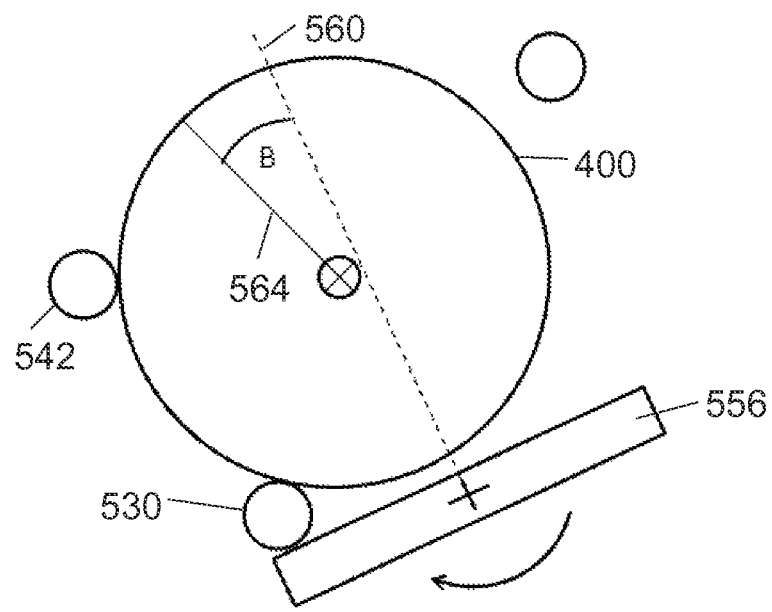

FIG. 34 shows the view from FIG. 28 shows the continued clockwise rotation of the carriage assembly 500 from the view of FIG. 33.

Figure 35:
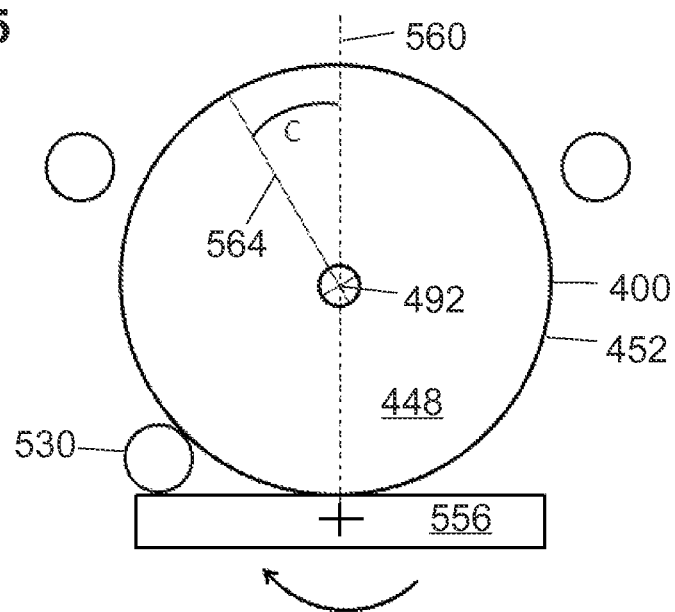

FIG. 35 shows the support plate 556 and thus the carriage assembly 500 at the same location as FIG. 28 but after a cycle of rotation of the carriage assembly 500.

Figure 36:
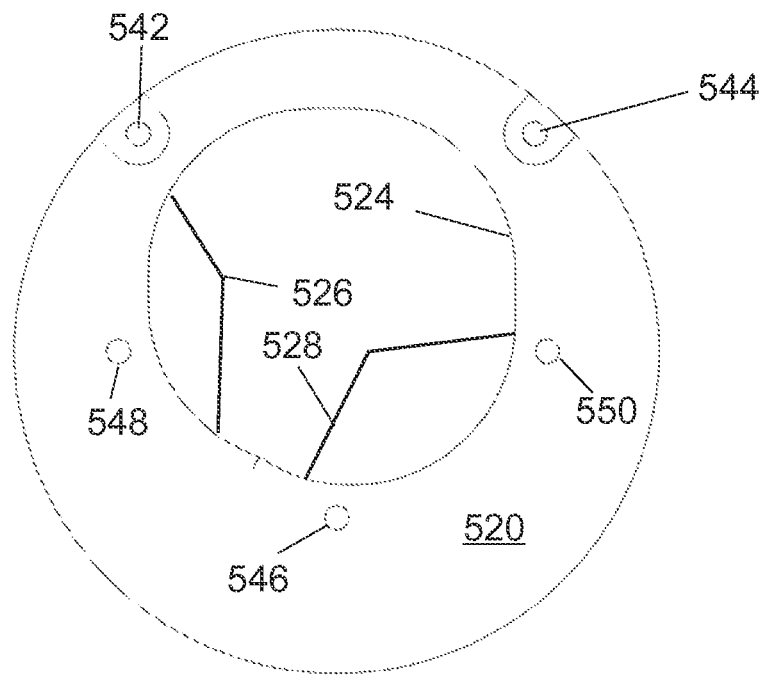

FIG. 36 shows the front plate 520 of the carriage assembly 500.

Figure 37:
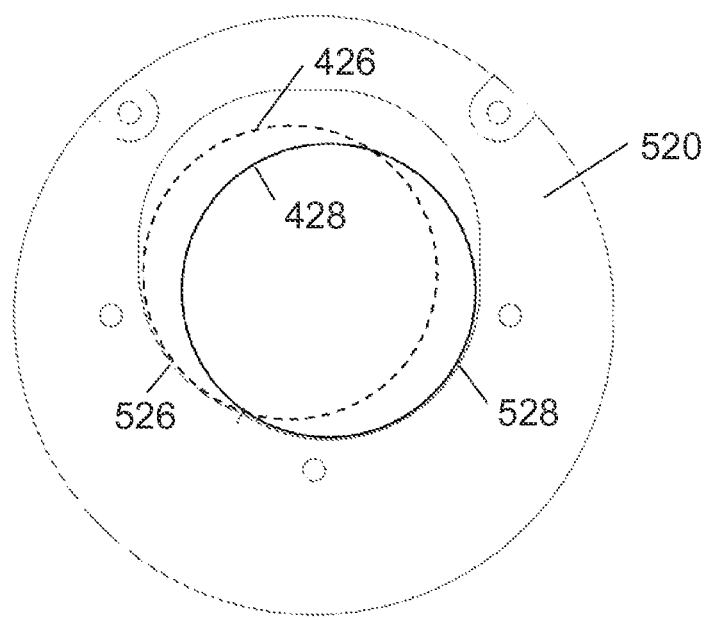

FIG. 37 shows two circles (426 and 428) that match up with the two separate portions (526 and 528) of the opening 524.

Figure 38:
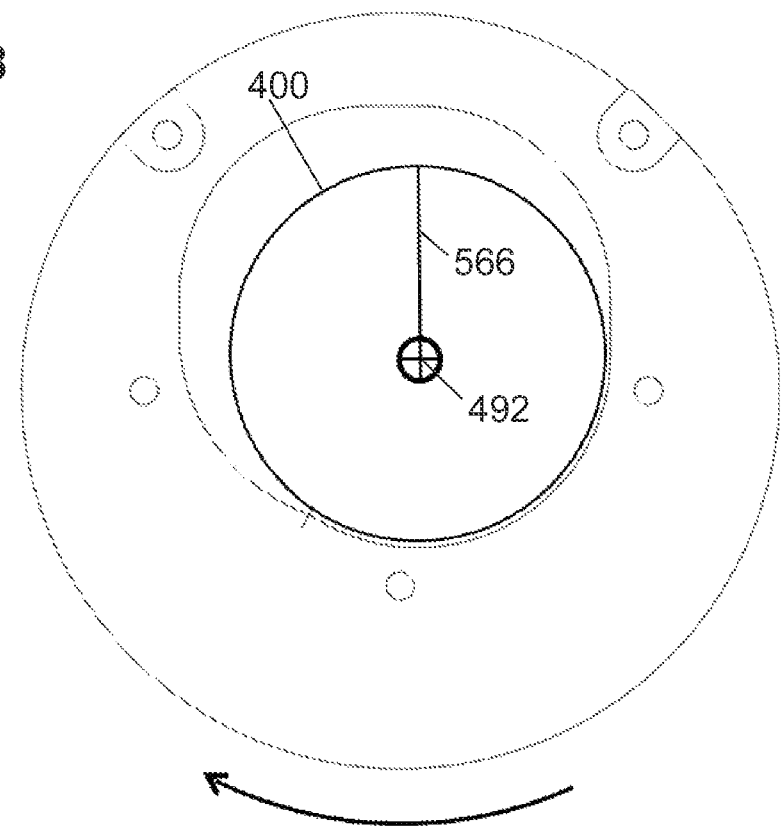

FIG. 38 shows the front plate 520 with the carriage assembly 500 in the same starting position as FIG. 28.

Figure 39:
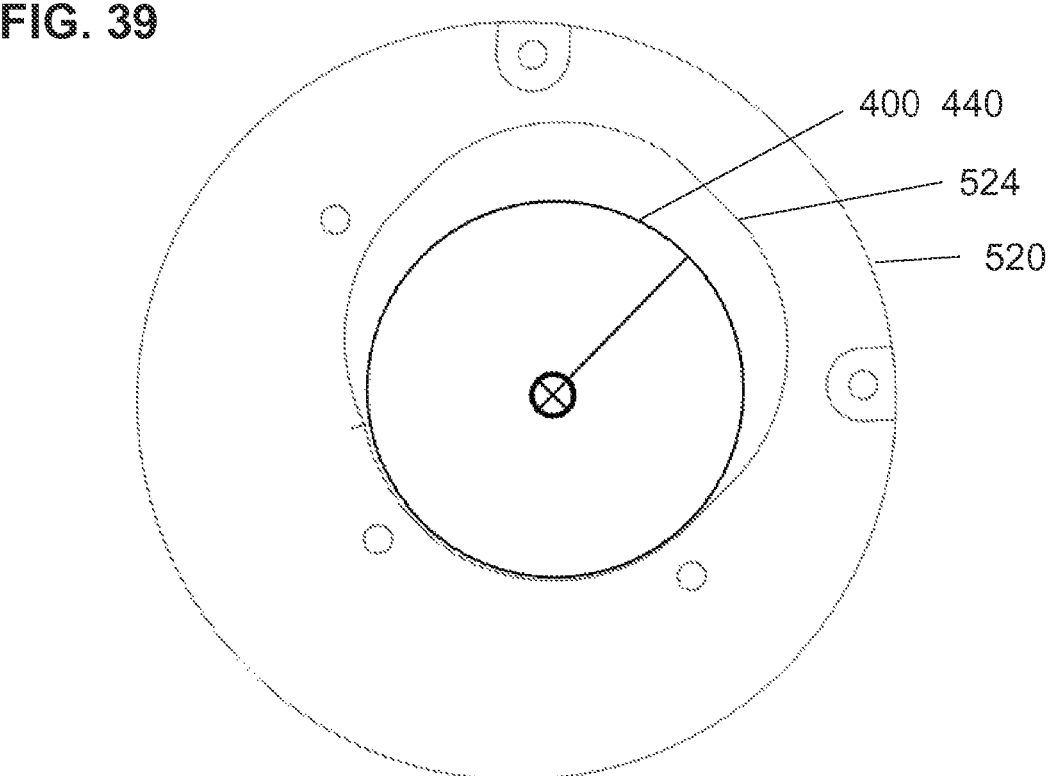

FIG. 39 shows the front plate 520 with the carriage assembly 500 in the same carriage assembly position as FIG. 29.

Figure 40:
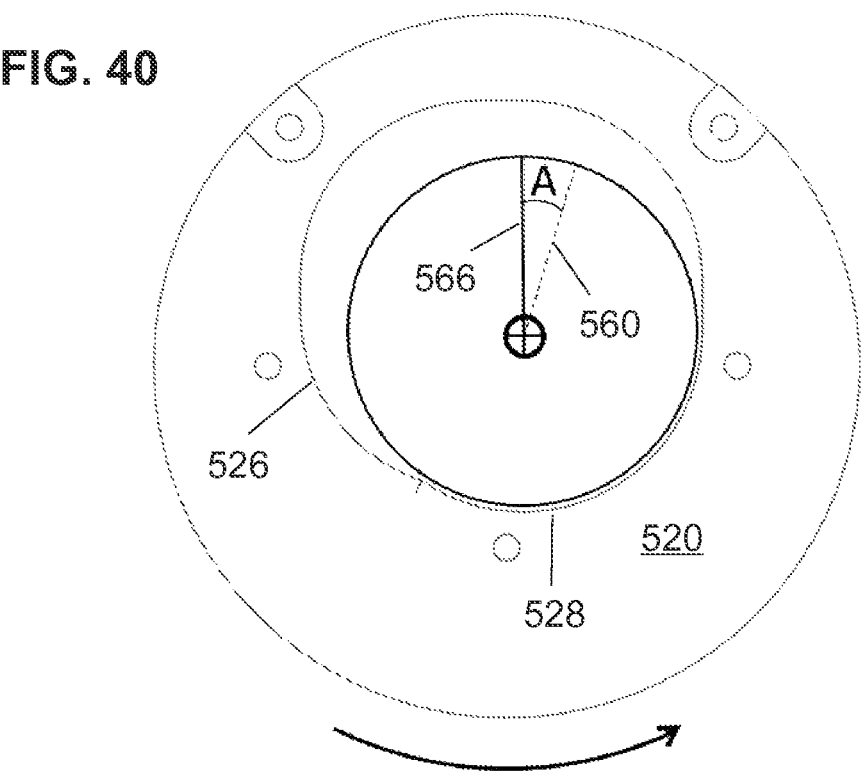

FIG. 40 shows the front plate 520 with the carriage assembly 500 in the same carriage assembly position as FIG. 30.

Figure 41:
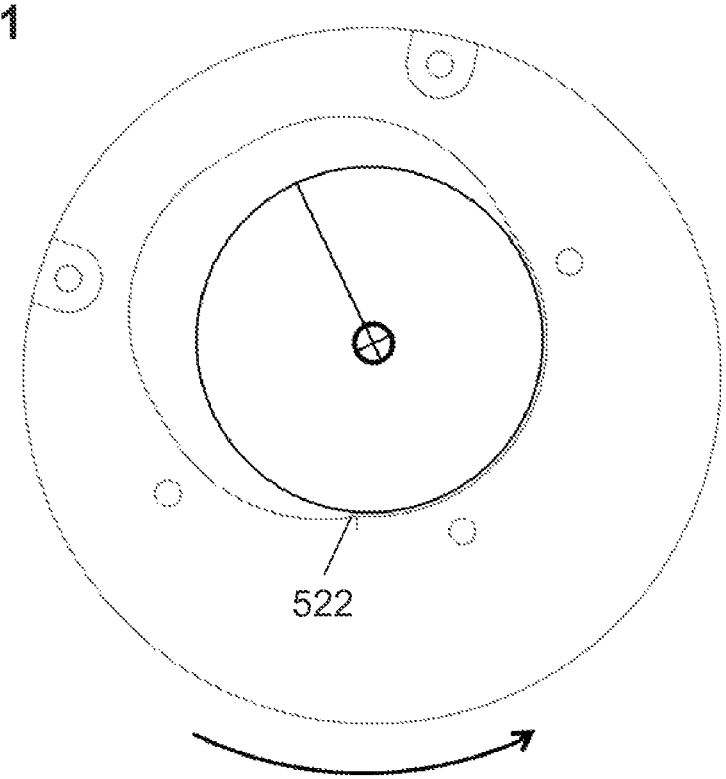

FIG. 41 shows the front plate 520 with the carriage assembly 500 rotated further in the counterclockwise direction from the position of FIG. 40.

Figure 42:
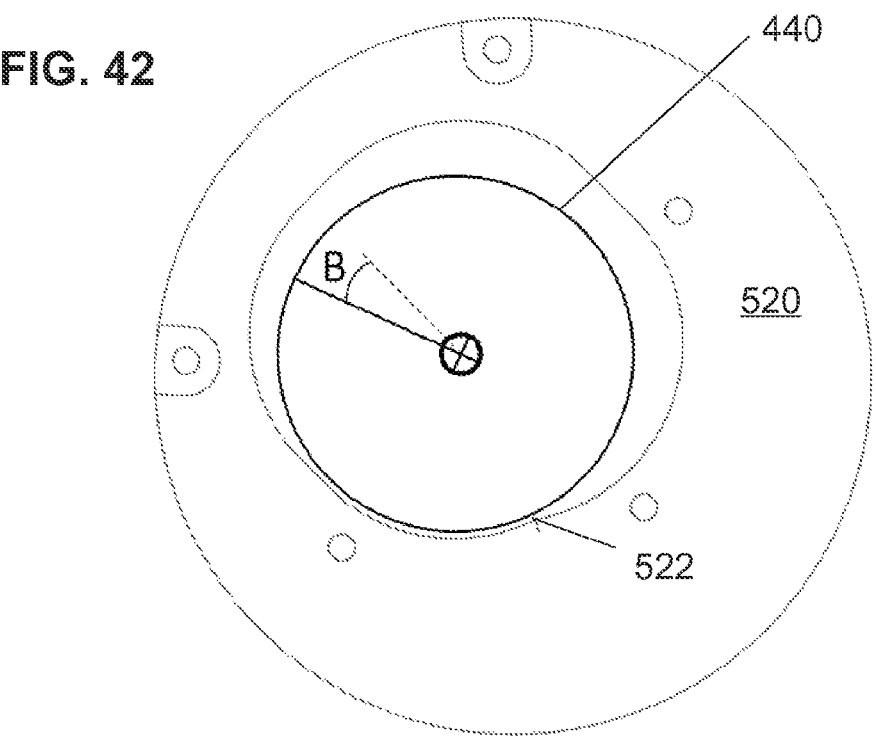

FIG. 42 shows the front plate 520 as the slush bottle 440 rolls over the transition point 522.

Figure 43:
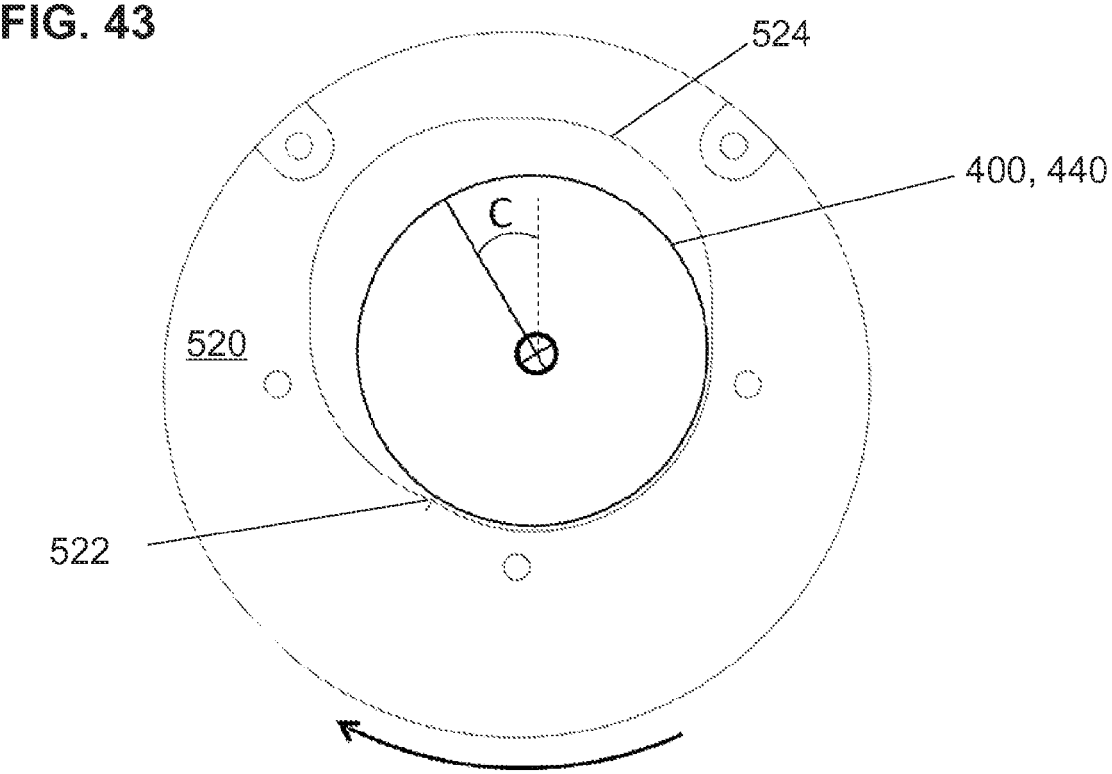

FIG. 43 shows the front plate 520 with the carriage assembly 500 in the same carriage assembly position as FIG. 38 after a carriage assembly motion cycle.

Figure 44:
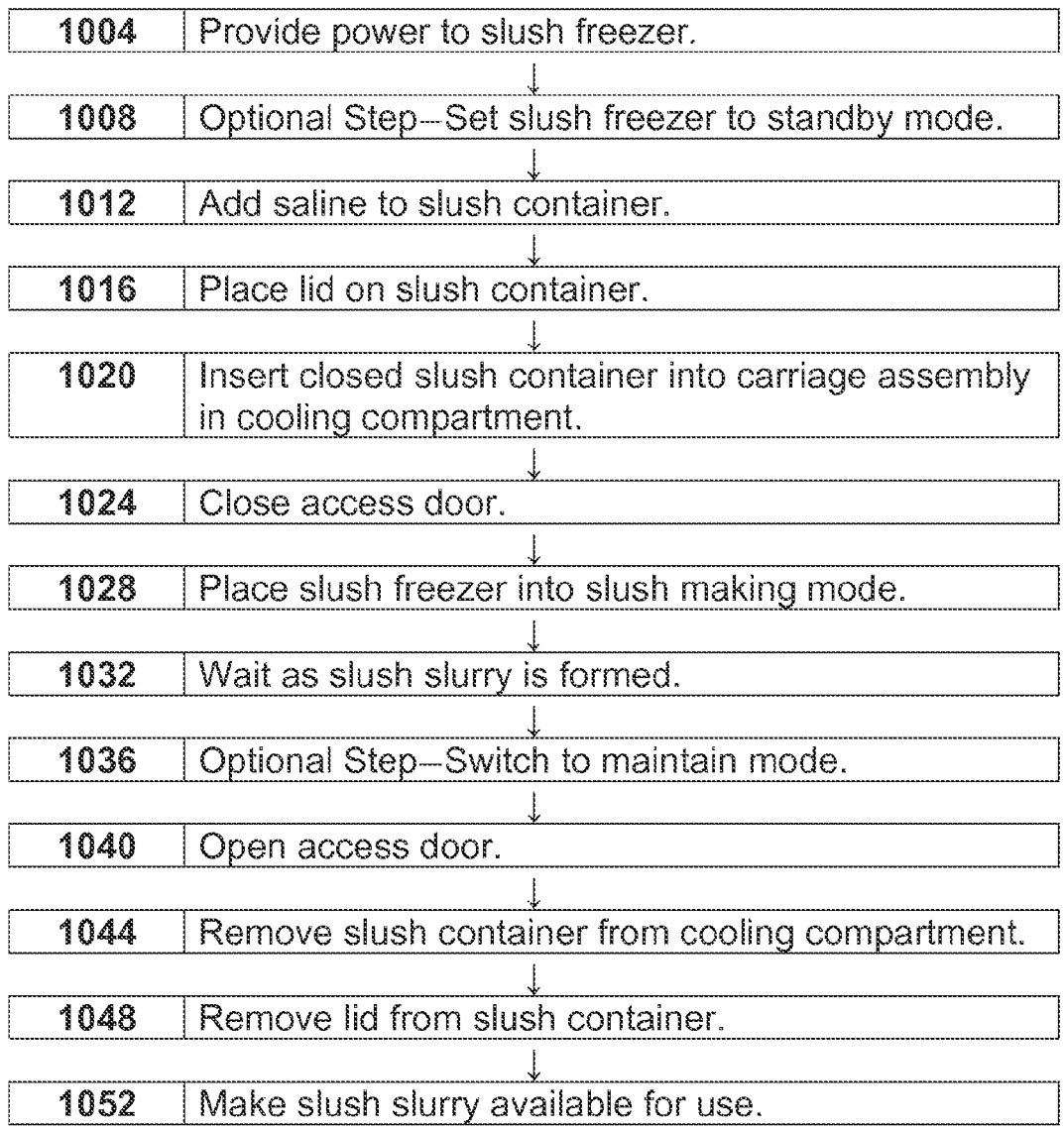

FIG. 44 provides a high-level overview of a process 1000 to make surgical slush.

Figure 45:

FIG. 45 provides a high-level overview of a process 2000 to deliver surgical slush into a sterile field.

Figure 46:
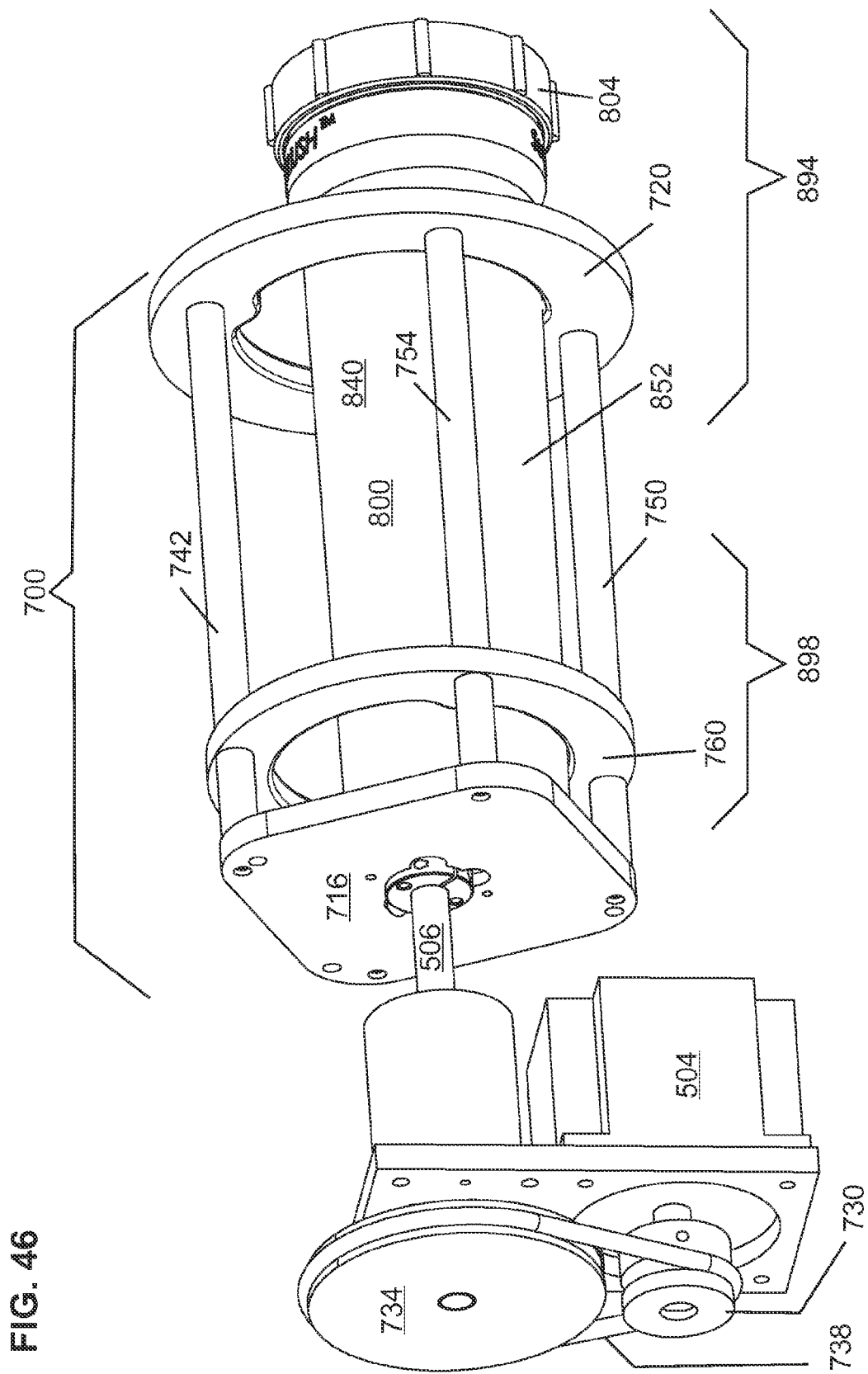

FIG. 46 perspective view of motor and carriage assembly 700 with slush container 800.

Figure 47:
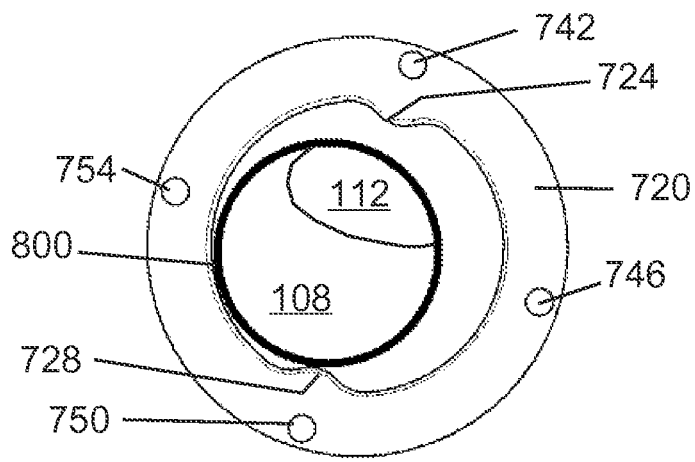
Figure 48:
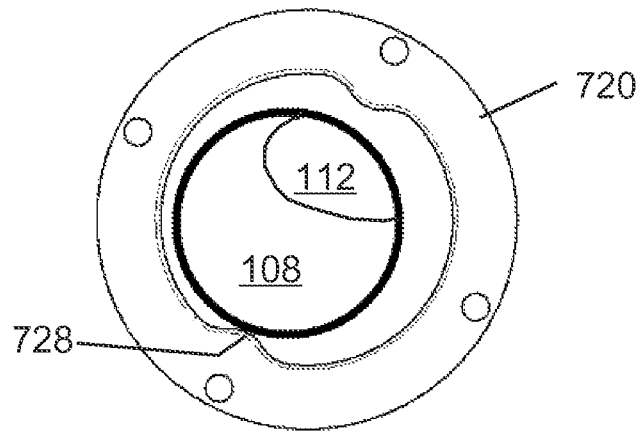
Figure 49:
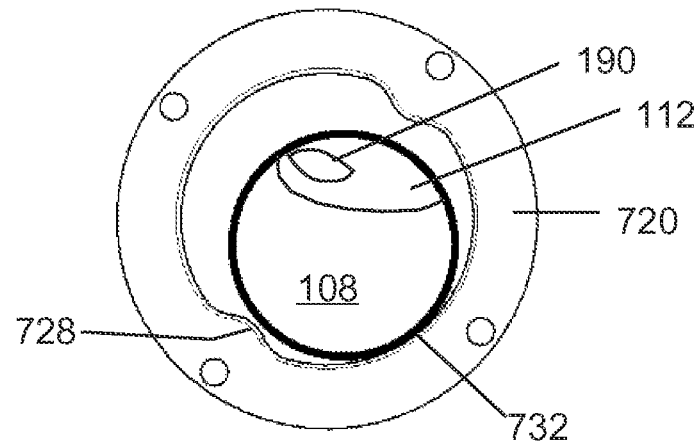

FIG. 47, FIG. 48 and FIG. 49 show a sequence of clockwise movements of front plate 720.

Figure 50:
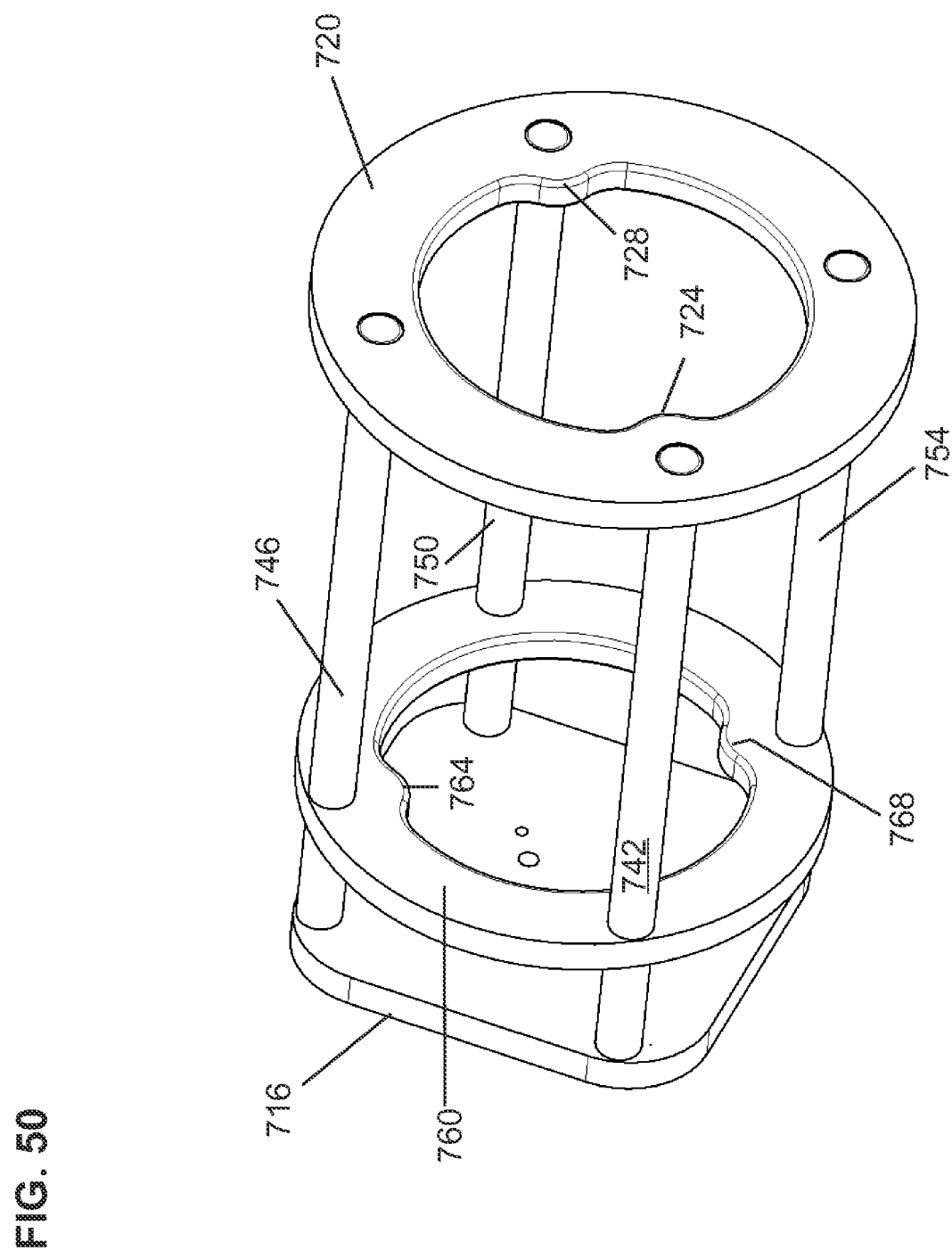

FIG. 50 is a perspective view of the carriage assembly 700 without a slush container 800.

Figure 51:
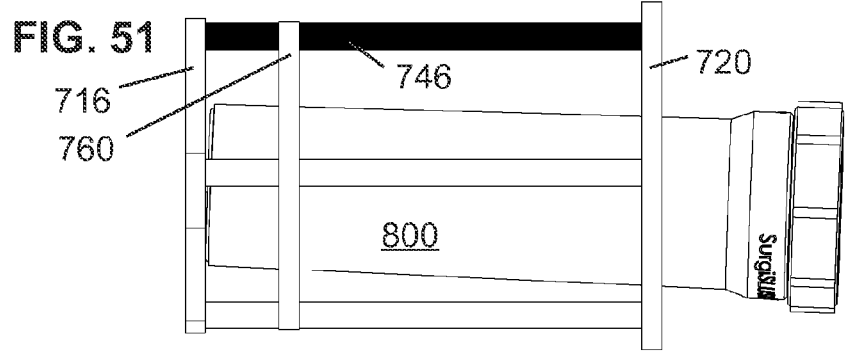

FIG. 51 shows a side view of a slush container in a carriage assembly 700 with spacer tube 746 at the 12 o'clock position.

Figure 52:
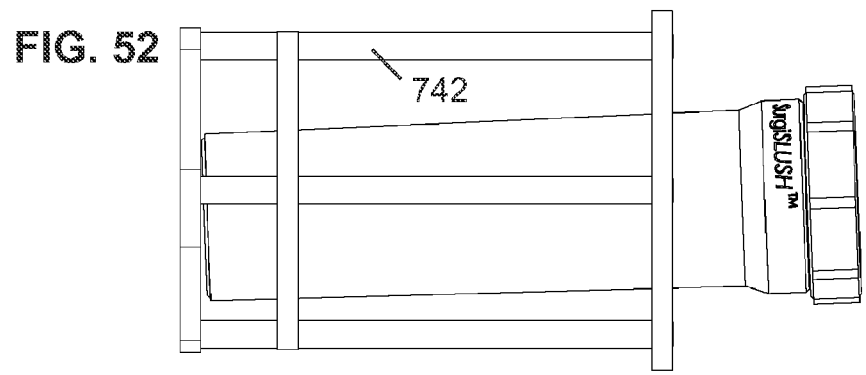

FIG. 52 shows a side view of a slush container in a carriage assembly 700 with spacer tube 746 hidden at the 3 o'clock position.

Figure 53:
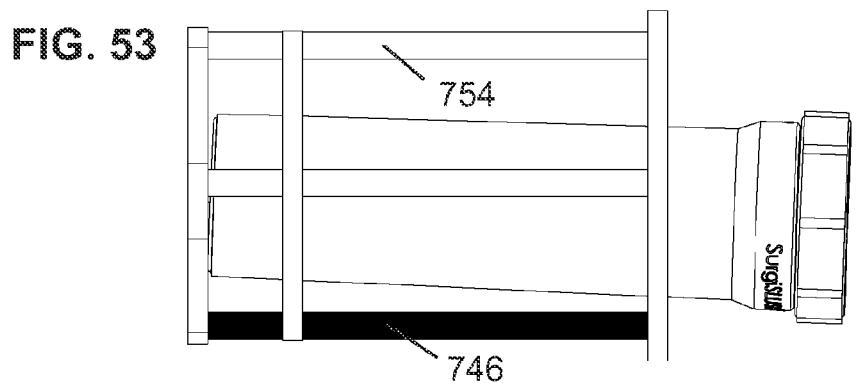

FIG. 53 shows a side view of a slush container in a carriage assembly 700 with spacer tube 746 at the 6 o'clock position.

Figure 54:
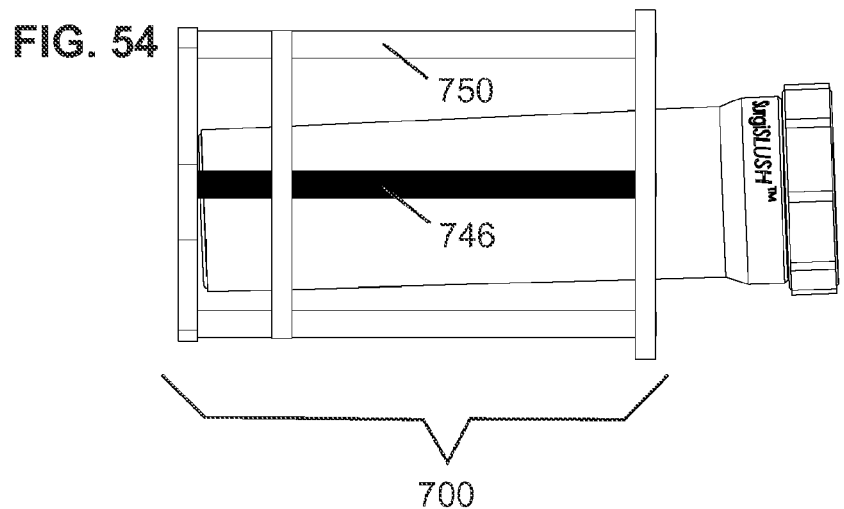

FIG. 54 shows a side view of a slush container in a carriage assembly 700 with spacer tube 746 at the 9 o'clock position.

FIG. 55 shows a cross section of a slush container within the distal plate 760 with spacer tube 746 at the 12 o'clock position.

FIG. 56 shows a cross section of a slush container within the front plate 720 with spacer tube 746 at the 12 o'clock position.

FIG. 57 shows a cross section of a slush container within the distal plate 760 with spacer tube 746 at the 3 o'clock position.

FIG. 58 shows a cross section of a slush container within the front plate 720 with spacer tube 746 at the 3 o'clock position.

FIG. 59 shows a cross section of a slush container within the distal plate 760 with spacer tube 746 at the 6 o'clock position.

FIG. 60 shows a cross section of a slush container within the front plate 720 with spacer tube 746 at the 6 o'clock position.

FIG. 61 shows a cross section of a slush container within the distal plate 760 with spacer tube 746 at the 9 o'clock position.

FIG. 62 shows a cross section of a slush container within the front plate 720 with spacer tube 746 at the 9 o'clock position.

FIG. 63 shows a cross section of a slush container within the distal plate 760 with spacer tube 746 back at the 12 o'clock position but with the index mark 790 rotated more than one rotation.

FIG. 64 shows a cross section of a slush container within the front plate 720 with spacer tube 746 back at the 12 o'clock position.

Figure 65:
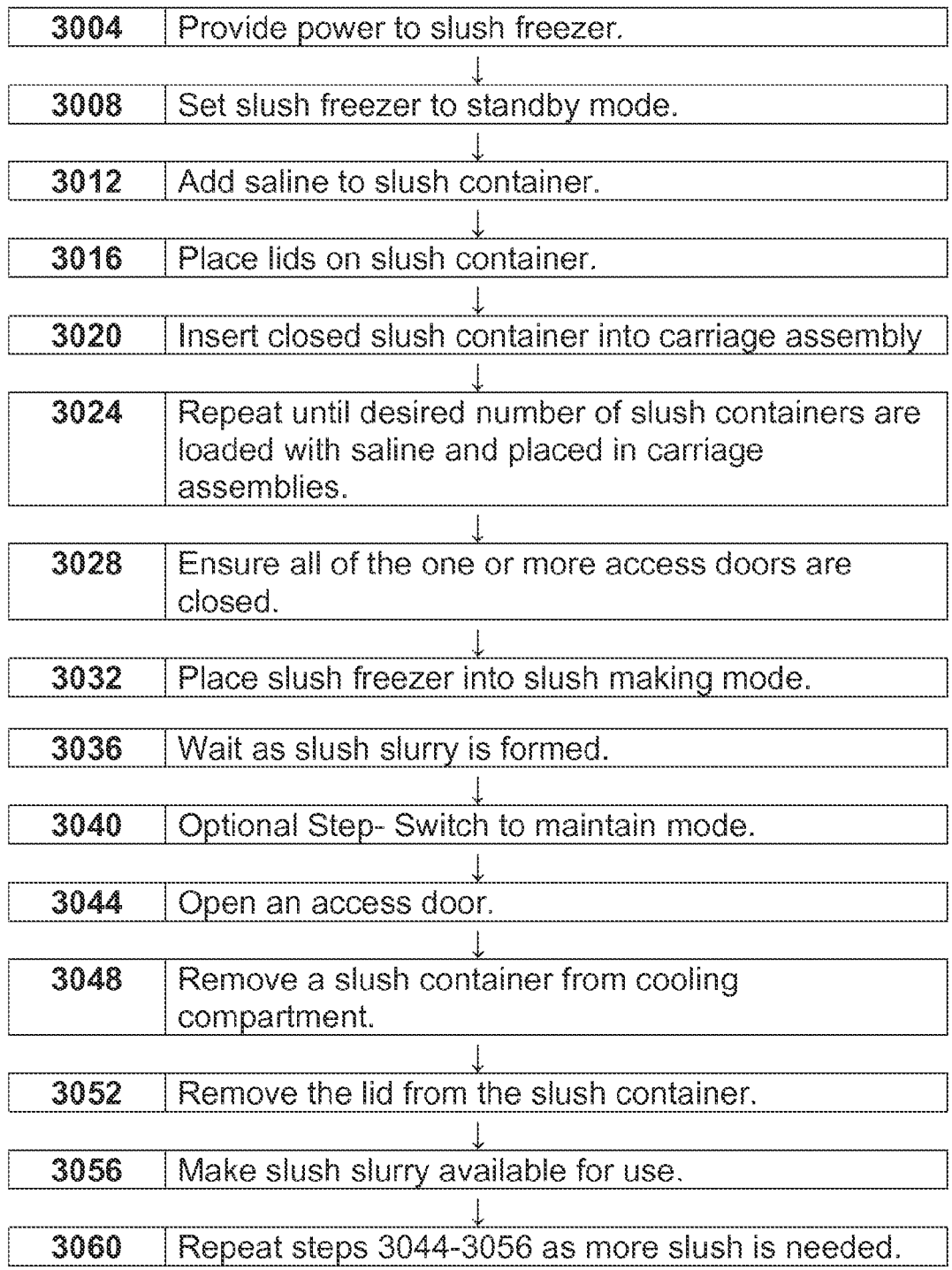

FIG. 65 provides a high-level overview of a process 3000 to make surgical slush when two or more carriage assemblies are driven by one motor.

DETAILED DESCRIPTION

A slush slurry is created when a slush container containing sterile saline and some air is placed in a slush making machine where the slush container is exposed to ambient air that has been chilled sufficiently to freeze some of the liquid in the sterile saline to form a mixture of ice and liquid saline.

FIG. 1 and FIG. 2 introduce concepts useful for understanding the first disclosed method of agitating a slush slurry. FIG. 1 shows a lower portion of a cross section of a container 104 with a substantially rectangular cross section. The container 104 is partially filled with sterile saline 108 and has an air gap 112 above the sterile saline 108. The air gap 112 serves an important function as the presence of the air gap 112 above the sterile saline 108 allows the sterile saline 108 to move differently than if a closed container was totally filled with saline. The upper part of the container 104 may have a bottle neck or some other shape.

To help illustrate the relevant concepts, three particles of water are identified, particle 1, particle 2, and particle 3. FIG. 2 shows the container 104 from FIG. 1 immediately after the container 104 was quickly moved to the left. As the right side wall 116 moves quickly to the left, the right side wall 116 collides with the previously stationary particles (1, 2, and 3). Since there are other particles in the fluid beyond merely particles 1, 2, and 3, the angle that the particle bounces off the wall is not 90 degrees (like a tennis ball hit by a tennis racquet). The actual path of the particles will be more complex as the paths will be influenced by the interactions with other particles. Particles near the bottom, like particle 1, will see some resistance to bouncing straight back due to other particles approaching the wall and their paths will be diverted either up or down. The bottom of the container will make particles in this region have a slight upward motion tendency.

Particle 2 will also be impacted by other particle approaching the wall, but it will also see an upward rush of particles from below and will have more of an upward reflected path than particle 1. The same holds true for particle 3 which will be further directed upward. The result will be an upward swell of fluid along the wall that eventually turns into a wave once the right side wall 116 stops moving.

FIG. 3 and FIG. 4 show a second container 124 and fluid interaction but with a container wall that is substantially curved. When the container 124 is moved rapidly to the left (in the same way as done with respect to FIG. 2), the particles will bounce off the right side wall 128, but the angle of incidence and reflection will be different than illustrated in FIG. 2.

Particle 1 in FIG. 4 will bounce off the right side wall 128 with a greater vertical motion component than illustrated for particle 1 in FIG. 2. Likewise, particles 2 and 3 in FIG. 4 will bounce off the right side wall 128 with vectors having greater vertical motion components and will also experience a larger uprush of particles below than shown in the FIG. 2 example. The result will be a larger upward fluid swell due to the curved shape of container 124.

FIG. 5 and FIG. 6 show a container 130 with a circular profile that is partially filled with a sterile saline 108 and thus has an air gap 112 above the sterile saline 108. The cross section can be a cross section of a cylindrical container laid horizontally. Four particles are shown with particles 1 and 2 below the marked diameter 134 and particles 3 and 4 above the marked diameter 134.

FIG. 6 shows the container 130 after being rapidly moved to the left in the same manner as containers 104 and 124 were moved. Particle 1 hits the right side wall 138 and bounces in the upward direction due to the angle incidence with the wall. Particle 2 also has an upward rebound off the right side wall 138 due to the angle of incidence and the upward rush of fluid from particles below it. Since particle 3 is above the marked diameter 134, absent interaction with surrounding fluids, particle 3 would bounce in the downward direction due to the angle of incidence. (Shown with the vector 3A in FIG. 6.) However, if there is sufficient uprush of particles from collisions that occurred below the container marked diameter 134, the particle 3 would follow a path indicated by vector 3B.

Particle 4 would also bounce down in direction of vector 4A if there were no other particles, but could be diverted upward in direction of vector 4B if forced by particles from below. The result of motion indicated by vector M1 is to produce a general rotation of fluid indicated by vector M2.

FIG. 7 and FIG. 8 show the container 130 previously shown in FIG. 5 and FIG. 6 but instead of the container 130 being displaced in the horizontal plane, the container 130 is forced to follow an arc pattern about a center of rotation 142. Note, in practice, the actual center of rotation 142 may be much closer to the longitudinal centerline 146 of the container 130. In practice, center of rotation 142 may be within the radius of the container 130, but the center of rotation 142 has been moved further out to make the drawing less cluttered.

Four particles are shown, with particle 1 and particle 2 below a marked diameter 134. Marked diameter 134 is merely a reference line included in various drawings to facilitate illustration of particle movement. Particle 3 and particle 4 are above the marked diameter 134. If the container 130 starts from a stationary position of 45 degrees offset from vertically below center of rotation 142 as shown in FIG. 7 and the container 130 is quickly displaced in a clockwise direction about the center of rotation 142 as shown in FIG. 8, the particles will collide with the container wall 138 as shown. We will assume that the velocity profile of the container 130 is greater than the speed at which the particles would free fall due to gravity. The particle motion will be the same as described for FIG. 6 except the incidence angles will be slightly different because the motion is circular instead of linear. For larger radius of motion and for particles very close to the wall the behavior of particles in FIG. 8 will much like that shown in FIG. 6. The result of motion indicated by M1 is to produce a general rotation of fluid indicated by M2.

The circular path of each particle will be defined by the radial distance between the particle and the center of rotation 142. Each particle will be experiencing the effects of gravity and centripetal acceleration based on the constraining force of the container wall 138. If we compare the centripetal acceleration of particle 1 to particle 4 we can see that particle 1 has a larger radius from the center of rotation 142 which will result in a larger centripetal acceleration and a corresponding larger centripetal force needed to keep the particle following the circular path. Assuming particle 1 and particle 4 have the same mass, the momentum of particle 1 is also larger due to the larger velocity vector associated with the larger radius. As a result of these particle dynamics, the particle 1 collision with the container wall 138 will be at a greater speed and will result in a larger exchange of momentum than the particle 4 collision with container wall 138. The particles below the marked diameter 134 will have a greater influence on flow after the collision than particles above the marked diameter 134 which further increases the tendency of counterclockwise flow shown by vector M2.

Importance of the Air Gap.

The circular containers 130 shown in FIG. 5 through FIG. 8 are depicted as only being partially filled with sterile saline 108, thus leaving room for an air gap 112. If the air gap 112 was eliminated and the containers 130 were totally filled, the linear displacement shown in FIG. 6 would result in a different fluid flow pattern than described above. The linear displacement would cause particle 3 and particle 4 to bounce downward toward the marked diameter 134 of the container 130 with about the same force as particles 1 and 2 bounce upward. The result would be colliding flows at the centerline that would not produce a defined counterclockwise flow as indicated by M2 in FIG. 6.

However, the dynamics described above for the circular motion depicted in FIG. 7 and FIG. 8 will still result in a general counterclockwise motion even if the container was totally filled with liquid. This motion relative to a center of rotation 142 is beneficial as it will work to generate the desired motion (M2) independent of whether the container is fully or partially filled. Thus, the effect of the air gap 112 augments the motion induced from rotation around a center of rotation 142.

Sharp Reversals of Rotation.

A motion that swings the container 130 counterclockwise about center of rotation 142 from an angular position of less than 45 degrees, then quickly reverse the direction of rotation to clockwise at 45 degrees causes an increase in the magnitude of the particle to wall interaction. One skilled in the art and familiar with Newton's $1^{st}$ Law of Motion can see this will result in a larger general rotation of fluid in the direction shown by M2 in FIG. 8.

Note, while a rotation of 45 degrees in both directions works well, the rotation in one direction could be less than a rotation in the other direction. Likewise, the sum of the two rotations does not need to be 90 degrees but could be a number either more than or less than 90 degrees.

FIG. 9A through FIG. 9D shows a container 130 swinging about a center of rotation 142. The container 130 is shown in four different positions: Position A shown in FIG. 9A; Position B shown in FIG. 9B; Position C shown in FIG. 9C; and Position D shown in FIG. 9D.

Assume the container is oscillating back and forth through the positions A-B-C-D-C-B-A-B and so on. If the change in direction from position C to position D and back to position C occurs with the same velocities and accelerations as the change from position B to position A and back to position B again, then the sterile saline 108 fluid will first experience a driving force to cause a counterclockwise rotation followed by an equal and opposite force to cause a clockwise rotation. This produces a very good mixing regime when the solution is 100% liquid. However, after part of the solution has turned to slush, the flow dynamics set up by this mixing is not very effective at keeping a homogeneous sodium chloride concentration and temperature distribution.

Asymmetric Rotation Reversals.

The change in rotational direction of container 130 around a center of rotation 142 at position A results in a counterclockwise rotation of the slush while the change in direction at position D results in a clockwise rotation. If the changes in direction have the same rates of change, then the effects tend to offset one another. However, if the change in direction at position A occurs with higher velocities and accelerations than at position D, the magnitude of counterclockwise rotation will be greater than magnitude of clockwise rotation. The result after a series of continuous oscillations is a general trend toward counterclockwise rotation. This rolling of slush inside the container 130 keeps the slush constantly moving relative to the container walls 138 and reduces the individual crystal contact time with the container wall 138. The rolling dynamics is effective regardless of the concentration of slush in the container 130.

An effective way to generate oscillatory motion is to use a standard four-bar mechanism as shown in FIG. 10. One skilled in the art would be able to size a crank arm 204, rocker arm 212, and linkage 208 that allows a motor driven crank arm 204 to rotate 360 degrees while the rocker arm 212 oscillates back and forth. The FIG. 11 example shows the rocker arm 212 rotating back and forth by 90 degrees as the crank arm 204 rotates 360 degrees. The position of components using solid lines shows the rocker arm 212 at the furthest counterclockwise location of the rocker arm 212 while position of components using dashed lines is at the furthest clockwise position of rocker arm 212. If the crank arm 204 is driven by a constant speed motor, the mechanism in FIG. 11 will produce a rocker motion that is close to symmetric in that it will take about the same time for the rocker to move from the extreme counterclockwise position to the extreme clockwise position as it take for the rocker arm 212 to move from the extreme clockwise position to the extreme counterclockwise position. This rough equality in times can be seen by observing that the solid and dashed line positions of the crank arm 204 are close to 180 degrees apart. Thus, with a constant speed motor, the time for the both the clockwise movement and the counterclockwise movement is approximately half of a rotation cycle of the motor.

Crank Rocker Linkage for Asymmetric Movement.

FIG. 12 shows a modified linkage that again produces a 90 degree motion of the rocker arm. However, the linkage lengths are design to establish a non-symmetric motion. With a constant speed crank motion, it will take less time for the crank arm 204 to rotate from solid position to the dashed position than to go from the dashed position to the solid position. As with FIG. 11, the solid line shows the position of the crank arm 204 for the most extreme counterclockwise rotation of rocker arm 212. The dashed lines show the component positions for the most extreme clockwise rotation of rocker arm 212. As the time for the crank arm 204 to rotate from the solid position to the dashed position is less than the time needed for the rotation from the dashed position to the solid position, the motion of the rocker arm 212 from the solid position to the dashed position will be faster than the motion from the dashed position to the solid position.

Using a four bar mechanism similar to the one show in FIG. 12 to drive a container through a swinging motion as shown in FIG. 9 will produce a slush mixing action that causes the slush to roll relative to the container walls 138. This slush mixing action keeps the sodium chloride concentration and temperature distribution sufficiently consistent to produce fine slush formation. A range of oscillation speeds may be used. The choice of oscillation speed used will be a function of the overall design including the intensity of the speed changes and the temperature of the ambient air used to cool the saline solution.

One of skill in the art will appreciate that the asymmetric rotational movement could be implemented to bias the motion to create more counterclockwise movement than clockwise movement of the slush slurry or could bias the motion to create more clockwise movement than counterclockwise movement. Either would be suitable for mixing the slush slurry. Motion viewed from one end of a cylinder as counterclockwise relative to a centerline would simultaneously be viewed from the other end of the cylinder as clockwise rotation.

Likewise, one of skill in the art will recognize that while FIG. 7, FIG. 8, and FIG. 9 show a container swing with the center of rotation above the container, one could obtain similar motion of particles when using a container placed above the center of rotation for the oscillations.

A Mechanism to Produce Complex Movement.

While those of skill in the art will be able to take the teaching of the present disclosure and create a wide range of mechanisms to cause the saline/slush/air contents of a slush container to be sufficiently agitated to prevent slush buildup on the smooth hydrophobic interior surfaces of the slush containers so that a well-mixed slush slurry is maintained, a specific example is provided in keeping with the requirement for enablement.

A slush freezer 300 with two cooling compartments 304 and 308 is shown in front plan view in FIG. 13. This slush freezer 300 has at least one refrigeration unit (not shown here) to cool ambient air circulated around the interiors of the cooling compartments 304 and 308. The ambient air in the first cooling compartment 304 may be isolated from the ambient air in the second cooling compartment 308 so that one cooling chamber may be operated at a different temperature from the other cooling chamber. For example, one cooling chamber may be actively cooled for the production of slush while the other cooling chamber is either not in use or is being used to maintain slush that has been created but has not been removed for use. While slush freezer 300 is shown with two cooling compartments 304 and 308, a slush freezer may have a single cooling compartment or more than two cooling compartments.

Each cooling compartment 304, 308 may have an access door 314 or 318. The access door 314 or 318 may be transparent to allow viewing of the activities within the cooling compartment 304 or 308 without opening the access door 314 or 318. The access doors 314 or 318 may be connected to the control system so that movement of the carriage within a cooling compartment may stop when the access door 314 or 318 for a cooling compartment 304 or 308 is opened. This feature is to avoid injury to users from contact with moving components. The control system may include a control which allows the carriage assembly to be stopped and prevented from movement by the user.

The slush freezer 300 may be equipped with a set of caster wheels 322. Some or all of the caster wheels 322 may be equipped with a lock mechanism 326.

FIG. 14 provides a top view of slush freezer 300. Cooling compartment 304 and cooling compartment 308 with access doors 314 and 318 are visible on a slanted portion of front side of the slush freezer 300.

Those of skill in the art may implement the control systems and user interfaces in a variety of ways while using the teachings of the present disclosure with respect to the creation of surgical slush so the details of the user interface need not be described in detail here.

FIG. 15 through FIG. 19 show several views of a slush container 400 suitable for use with the present disclosure. While slush container 400 is suitable for use, other slush containers may be used with any appropriate modifications of the slush carriage, cooling pattern, and related details.

FIG. 15 shows a top perspective view of slush container 400 including lid 404 and slush bottle 440.

Lid 404 may have a set of internal threads to reversibly engage threads 456 on the slush bottle 440 near the bottle opening 444. Optional gripping ribs 408 are shown on lid 404. The gripping ribs or other textured surface may make it easier to open a slush container 400 with frost upon the exterior. Likewise, gripping ribs or some other textured surface may be added to the slush bottle 440. For example, grooves (not shown) may be cut into the lower expanded region 464.

When the lid 404 is secured to the slush bottle 440, the slush container 400 forms a closed volume, defined by bottle bottom 448, bottle wall 452, and the lid 404.

The slush container 400 may have an internal volume of 1.3 liters and be intended for use with one liter of sterile surgical saline. Bottle opening 444 of slush container 400 has a wide mouth without obstructions, unlike a bottle neck. Optionally, the bottle wall 452 may taper outward so that the bottle opening 444 is slightly larger than a cross section of the slush bottle 440 taken near the bottle bottom 448. In order to facilitate release from the container mold, it is useful to have a slight taper, perhaps 0.5 to 1 degree to make the inside diameter of the slush bottle 440 grow in the direction from bottle bottom 448 to the bottle opening 444. This taper is also helpful in the release of slush from the slush bottle 440.

The slush container 400 is preferably transparent or at least substantially translucent so that the degree of conversion from liquid saline to slush slurry may be observed without opening the slush container 400.

FIG. 16 is a top view of slush bottle 440. Visible in FIG. 16 are: bottle opening 444, the bottle bottom 448 that faces the interior of the slush bottle 440. Also visible in FIG. 16 are threads 456.

FIG. 17 is a bottom view of slush bottle 440. The bottle bottom 448 and the bottle wall 452 are visible.

FIG. 18 shows a first side view of slush bottle 440. FIG. 19 shows the opposite side view of slush bottle 440. As discussed in more detail below, the slush bottle 440 is preferably flexible enough to allow a user to easily squeeze the midpoint of the slush bottle 440 to preclude the entire payload of surgical slush from coming out as the bottle opening 444 of the slush bottle 440 is pointed towards a target container (such as a basin) within the sterile field.

The slush bottle 440 may have thicker walls at points of contact with the carriage as the slush bottle 440 moves relative to the carriage in the cooling compartment (304 or 308) and the life of the reusable slush container 400 may be extended by reinforcement at potential wear points of the slush bottle 440. Single use slush containers 400 would not need to be thickened at wear points.

The view shown in FIG. 18 of slush bottle 440 includes: threads 456, upper expanded region 488, top taper 484, top thickened region 480, thin middle region 476, lower thickened region 472, lower taper 468, lower expanded region 464, and bottle bottom 448.

The view shown in FIG. 19 breaks the slush bottle 440 into three sections. The sections are: lid end 494, middle 496, and bottom end 498. These regions are identified to assist with the disclosure and do not represent precise components found on the slush bottle 440.

As shown in FIG. 18, the slush bottle 440 may have a lip near the bottom end 498 of the slush bottle 440 to allow components within the slush freezer to engage the lip to limit undesired movement of the slush container 400 within the slush container carriage during oscillation of the carriage. In this case, the lip is lower taper 468 and lower expanded region 464.

Bubble Oscillation.

FIG. 20 and FIG. 21 show two views of slush container 400 with the saline slush 108 and air gap 112 visible. The edge between saline slush 108 and air gap 112 is labeled as interface 110. As the slush container 400 is undergoing agitation, the surface of the interface 110 is constantly changing so it is shown as a dash dot line rather than a solid line. One way to agitate any frozen layer of sterile saline 108 that might attempt to form on the inner surface of the slush container 400 is to only partially fill the slush container 400 and then rock the slush container 400 so that the air gap 112 moves from one end of the slush container 400 to another end.

As described in detail below, if the cycle of stimulation provided to the slush container 400 includes a mix of rolling and sliding movement of the slush container 400 relative to the carriage assembly 500, then the slush container 400 can be rotated around a longitudinal centerline 492 and relative to the contact points with the carriage assembly 500 so that the portion of the interior surfaces (452, 448, and 404) of the slush container 400 exposed to the moving bubble of the air gap 112 changes over a number of cycles of stimulus. Rapid changes to the slope of the closed slush container 400 cause movement of the air gap 112 and movement of the non-air contents of the closed slush container 400 so that at least a portion of the bottle bottom 448 of the closed slush container 400 and at least a portion of the interior side of removable lid 404 enter and leave the air gap to help shed ice crystals from those surfaces.

The complex movement causes any ice crystals which form on the interior surfaces of the closed slush container 400 to be eventually moved into the air gap 112. Once the thin layer of ice crystals is lifted out of the saline and slush, the thin layer of ice crystals would lack the support of adjacent saline or slush. Gravity will help remove the thin layer of ice crystals from the smooth and hydrophobic walls as the ice crystals will have difficulty adhering to the walls. When the complex movement accelerates the portion of the walls in the air gap 112 back into the saline slush mixture 108, the impact of the leading edges of the layer of ice crystals on the non-air contents will tend to scrub any remaining layer of ice crystals off walls.

Rotation of the closed slush container 400 relative to the longitudinal centerline 492 alters the portions of the interior walls of the closed slush container 400 being lifted into the air gap 112 and thus vary the locations being scrubbed from cycle to cycle to help keep ice from forming on the interior surfaces of the closed slush container 400.

Thus, it is desirable to have an elongated slush container 400 with the longitudinal centerline 492 positioned close to horizontal so that small movements of the lid end 494 of the slush container 400 relative to the bottom end 498 of the slush container 400 can vary which end of the slush container 400 is the elevated end of the slush container 400. FIG. 20 has the lid end 494 elevated relative to the bottom end 498 of the slush container 400 and thus has a larger air gap 112 at the lid end 494. Conversely, FIG. 21 has the bottom end 498 elevated relative to the lid end 494 of the slush container 400 thus has a larger air gap 112 at the bottom end 498.

One of skill in the art will recognize that the process could proceed with the air gap 112 moving so far towards one end that the other end temporarily has no air gap. This extreme movement may be achieved by a rapid acceleration of the closed slush container 400 or by a dramatic change in slope of the longitudinal centerline of the closed slush container 400. One of skill in the art will recognize that if there is a sufficiently large air gap from the ratio of liquid saline to air in the closed container, that it may not be necessary to alter the slope of the longitudinal centerline as ample portions of both ends will be in the air gap 112. Thus, the movement of the air gap 112 relative to the interior walls of a close slush container could be achieved solely by rotation of the closed slush container 400 Note that the cross section of the substantially cylindrical slush container 400 as one moves away from the longitudinal centerline 492 grows smaller and thus the ratio of air gap 112 to saline slush 108 is actually smaller than suggested by FIG. 20 and FIG. 21.

The ratio of liquid to air may be in the nominal range of four to one. Being in the nominal range of four to one indicates that the range is closer to four to one than three to one and closer to four to one than five to one. However, the ratio may be significantly different from four to one. Ratios of liquid to air ranging from one to one to nine to one may be used with appropriate modifications to ensure adequate scrubbing of all interior surfaces by the movement of the slush container contents. Having a sizeable air gap 112 in the closed slush container 400 helps with keeping the walls free of ice crystals but too much air reduces the payload of surgical slush for a given slush container 400 and interferes with heat transfer as air does not conduct heat as well as liquid saline or surgical slush.

Complex Carriage Movement to Agitate Slush within Slush Container.

A carriage assembly 500 for receiving a slush container 400 is shown in FIG. 22. A motor 504 and linkage 508 are used to drive the carriage assembly 500 as described in more detail below. In this drawing and in the drawings that follow, elements present within the slush freezer 300 which are not central to the discussion about agitating the saline slush 108 within the slush container 400 are rendered invisible to allow focus on relevant components. Note that the axis of rotation 592 for the carriage assembly 500 is not the same as the longitudinal centerline 492 of the slush container 400.

This particular carriage assembly 500 is mounted within the slush freezer 300 at an approximately 10 degree angle in order to use legacy equipment. A motor 504 and carriage assembly 500 mounted horizontally would use adjustments to the carriage assembly 500 in order to provide an agitation sequence that moves the lid end 494 and the bottom end 498 of the slush container 400 to alternate being the highest part of the slush container 400 during the oscillation cycle. Such adjustments are within the skill set of those of skill in the art and need not be described here.

FIG. 23 shows the slush container 400 resting on the support plate 556 in the back and the front plate 520 in the front. The support plate 556 and the head 534 of the short pin 530 act to engage the lower taper 468 of the slush container 400 within the bottom end 498 of the slush container 400 to prevent the slush container 400 from moving towards the access door 314 (not shown here). A set of spacer tubes: 542, 544, 546, 548, and 550 (see FIG. 24) maintain the relative position of the front plate 520 to the back plate 516. All but the head 552 of spacer tube 548 has been made invisible to allow a better view of short pin 530 and support plate 556. Those of skill in the art could use a solid pin that fits into the front plate 520 or a spacer tube with a separate threaded rod that fits through the plates. The teachings of the present application do not require exactly five spacer tubes 542, 544, 546, 548, and 550 (See FIG. 24). One could easily imagine three, four, six, or seven spacer tubes.

As described in more detail below, it is the interaction of the slush container 400 with the carriage assembly 500 rotated by shaft 506 (See FIG. 24) that provides the agitation to the slush container 400 used to promote mixing of the saline slush 108 and inhibition of ice crystal accumulation on the interior surfaces (452, 448, and 404) of the slush container 400.

The following three sets of figures show the slush container 400 as the carriage assembly 500 is rotated through a sequence of positions. In order to convey the details with precision, the stimulus provided by the rear of the carriage assembly 500 to the bottom end 498 of the slush container 400 will be discussed separately from the stimulus provided to the lid end 494 of the slush container 400 by the carriage assembly 500. The relationships between the side views, back focus views, and front focused views are summarized in the following table.

Figure 24:
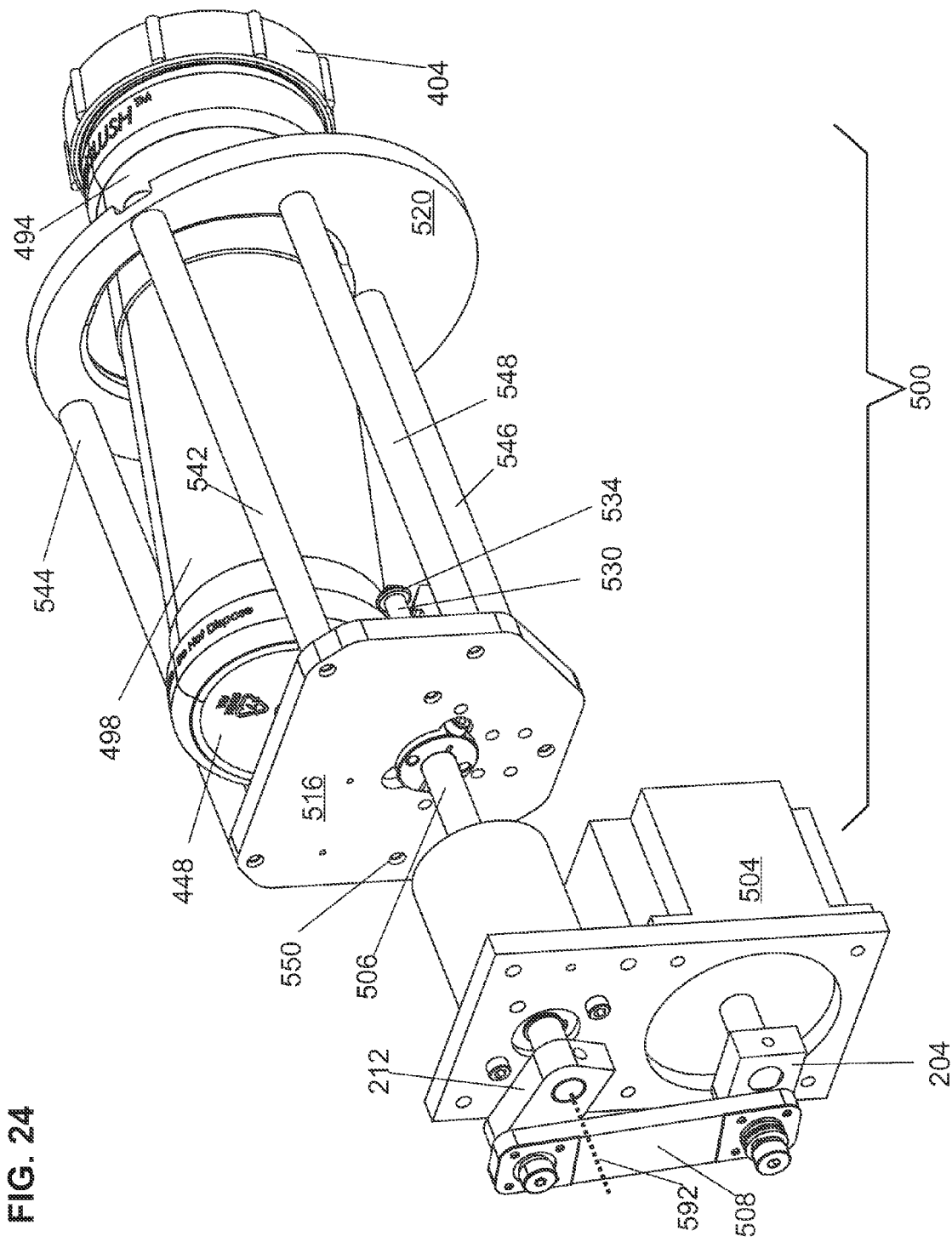
Figure 25:
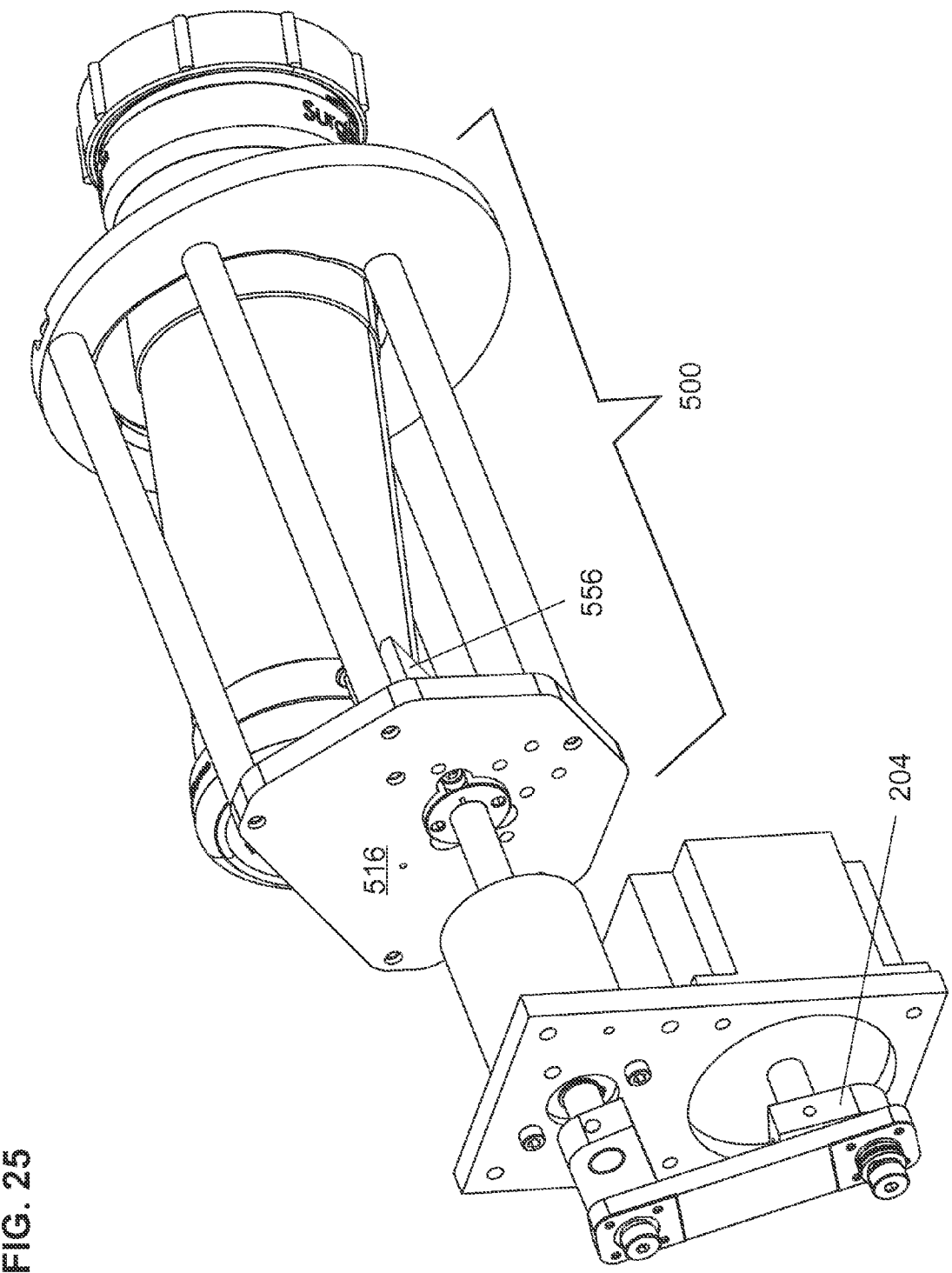
Figure 26:
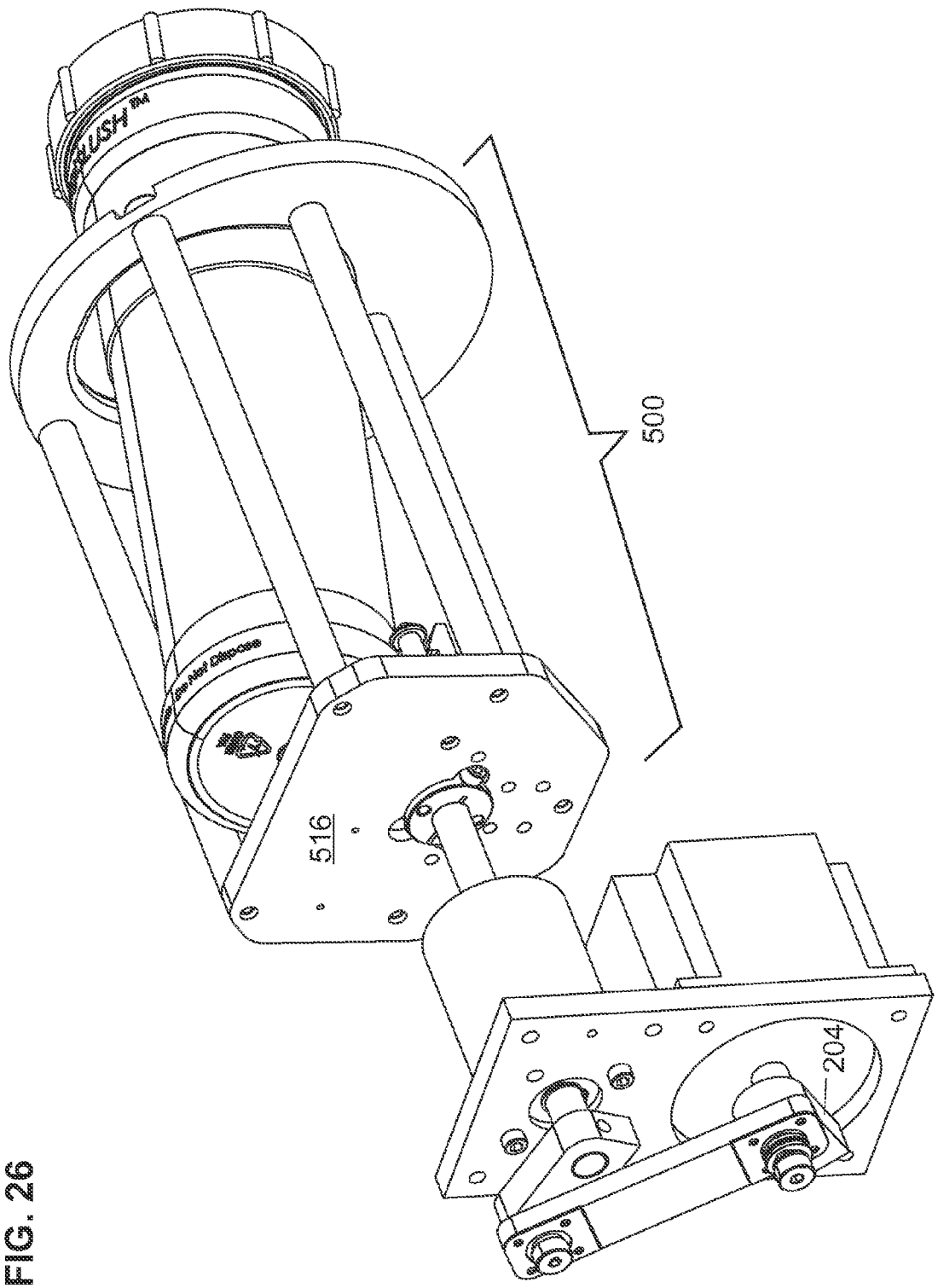
Figure 27:
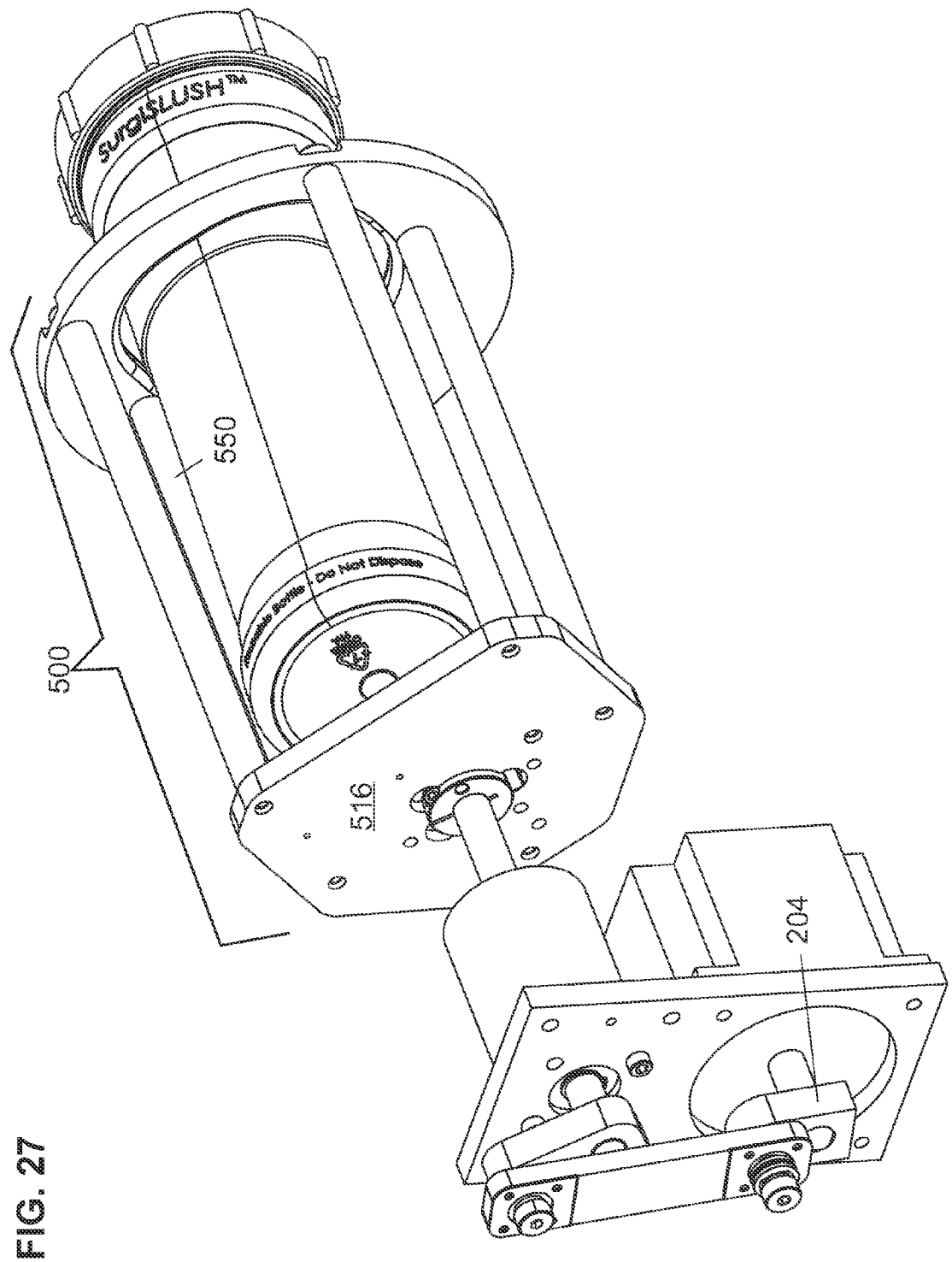

| Side View | Focus on Bottom End | Focus on Front Plate |
|---|---|---|
| FIG. 24 | FIG. 28 | FIG. 38 |
| FIG. 25 | FIG. 29 | FIG. 39 |
| FIG. 26 | FIG. 30 | FIG. 40 |
| FIG. 27 | FIG. 33 | FIG. 42 |

FIG. 24, FIG. 25, FIG. 26, and FIG. 27 show a sequence of movement of the carriage assembly 500 and slush container 400. The view is a rear and side perspective view created by rendering other components in the slush freezer 300 invisible. Labelled in FIG. 24 are previously discussed components: motor 504, linkage 508, center of rotation 592 running through shaft 506. Also visible are: short pin 530 with head 534, back plate 516, and front plate 520, separated by a set of five spacer tubes: 542, 544, 546, 548 and 550. Spacer tube 550 is hidden by slush container 400 except for the tip visible in the back plate 516. Slush container 400 has the bottle bottom 448 and the bottom end 498 toward the back plate 516 and the lid end 494 crossing an opening in the front plate 520 so that the lid 404 is beyond the front plate 520. Crank arm 204 and rocker arm 212 are visible from this view. Crank arm 204 is just past 9 o'clock (maybe 8:45) and is rotating counterclockwise. As discussed above, one of skill in the art can choose the combination of crank arm 204, linkage 508, and rocker arm 212 to impart asymmetric accelerations on the carriage assembly 500 and any slush container 400 present so that the accelerations experienced in the clockwise direction are not the same as experienced in the counterclockwise direction.

In FIG. 25, the carriage assembly 500 is rotated to an extreme position as indicated by the back plate 516 and the visible portion of the support plate 556. As viewed from the motor end, this is the maximum counterclockwise rotation of the carriage assembly 500. The crank arm 204 has moved from 8:45 to 5:30.

In FIG. 26, the carriage assembly 500 is rotated back to the position shown in FIG. 24 but the crank arm 204 is now at 1:45. Thus the movement from FIG. 24 to FIG. 26 was from 8:45 to 1:45. Conversely, the movement from FIG. 26 through the extreme position FIG. 27 (discussed below) and back to FIG. 24 happens from 1:45 to 8:45. Movement to and from the extreme position in FIG. 25 occurs in $7/12$ths of a revolution of the motor versus $5/12$ths of a revolution of the motor to move to and from extreme the position in FIG. 27. As discussed above this asymmetry helps create a circulation of the slush mixture relative to the slush container 400.

FIG. 27 shows the extreme position that is the opposite of FIG. 25. As viewed from the motor end, this is the maximum clockwise rotation of the carriage assembly 500. The crank arm 204 has moved from 1:45 in FIG. 26 to 11:15 in FIG. 27.

With this general understanding of how the slush container 400 is positioned and moved by the carriage assembly 500, attention can be turned to the specific stimulus provided to the slush container 400 by the carriage assembly 500 during oscillating rotation of the carriage assembly 500.

Focus on Slush Container Bottom within the Carriage.

FIG. 28 is a schematic representation of a few select components looking at a cross section of a slush container 400 and carriage assembly 500 taken approximately midway along the slush container 400 and looking towards the back plate 516 (not shown here). Spacer tubes 542 and 544 run between the back plate 516 and the front plate 520 (not shown here). Spacer tubes 546, 548, and 550 also run between the back plate 516 and the front plate 520 but are located below support plate 556 so are not shown in this sequence of drawings. Short pin 530 with head 534 extend from the back plate 516 to engage lower taper 468 (not shown here) in the bottom end 498 (not shown here) of the slush container 400. The center of rotation 592 of the carriage assembly 500 is aligned with the center of the shaft 506 (not shown here). This center of rotation 592 is shown on the support plate 556. Notice that center of rotation 592 for the carriage assembly 500 is not aligned with the longitudinal centerline 492 of slush container 400.

For illustration purposes, a dashed perpendicular line 560 is shown that originates at the center of rotation 592 for the carriage assembly 500 and extends perpendicular to the surface of the support plate 556. In FIG. 28 through FIG. 35 this dashed perpendicular line 560 is always shown perpendicular to the support plate 556. Additionally, a circle with a cross mark is shown along the longitudinal centerline 492 of the slush container 400 and a reference line 564 is shown extending from this longitudinal centerline 492 to the perimeter of the slush container 400. In FIG. 28 reference line 564 is aligned with dashed perpendicular line 560.

In FIG. 28 through FIG. 35, reference line 564 is shown to provide an indicator of the rotation of the slush container 400. While reference line 564 is not part of the slush container 400, the reference line 564 equates to what one would see after drawing a reference line on the slush container 400 and aligning the reference line 564 before starting a sequence of stimulus.

The carriage assembly 500 may be configured to rotate a total of 45 degrees clockwise to 45 degrees counterclockwise from the position shown in FIG. 28.

FIG. 29 shows the carriage assembly 500 rotated clockwise 45 degrees. This is maximum clockwise rotation and the point that the carriage rotation changes from clockwise to counterclockwise rotation. The movement from FIG. 28 to FIG. 29, the slush container 400 rolls to the right until the slush container 400 contacts the spacer tube 544. The angle produced by the rolling action relative to the support plate 556 is shown as angle A.

FIG. 30 shows the carriage assembly 500 as the carriage assembly 500 rotates counterclockwise and passes through the position where the support plate 556 is again horizontal. Because of the inertia of the loaded slush container 400 relative to the counterclockwise motion of the carriage assembly 500, the slush container 400 stays resting against spacer tube 544. The angle of rotation of the slush container 400 relative to the carriage assembly 500 remains virtually unchanged as shown by angle A in FIG. 30.

FIG. 31 shows the continued counterclockwise rotation of the carriage assembly 500. In FIG. 31, the inertia is still sufficient to keep the loaded slush container 400 up against spacer tube 544.

With slightly more counterclockwise rotation as shown in FIG. 32, the slush container 400 will eventually start to roll to the left along the support plate 556. With sufficient rolling, the slush container 400 eventually has a 0 degree angle relative to the support plate 556.

At some point in the rolling motion of the slush container 400 to the left along the back plate 516, the slush container 400 contacts short pin 530. This contact with short pin 530 occurs after the slush container 400 has started a rolling motion and has some angular momentum in the counterclockwise direction. The contact with short pin 530 also occurs below the longitudinal centerline 492 of the slush container 400 and produces a force on the slush container 400 that results in a counterclockwise moment on the slush container 400.

The combination of the angular momentum and the moment on the slush container 400 causes the slush container 400 to slip and rotate relative to short pin 530. Low friction between the slush container 400 and short pin 530 facilitates this slipping.

Turning to FIG. 33, while the slush container 400 is rotating about short pin 530, the slush container 400 lifts off of the support plate 556 and contacts spacer tube 542. The angle of the slush container 400 relative to the support plate 556 is shown as angle B. The angle of rotation shown as angle B can vary depending on the speed of rotation of the carriage assembly 500, the friction between the slush container 400 and short pin 530, the location of spacer tube 542, and contents of the slush container 400 (which changes during slush production as saline is converted to slush as described elsewhere in this background information). For typical conditions angle B may be approximately 20 degrees.

FIG. 33 also shows the location at which the carriage assembly 500 changes from counterclockwise to clockwise rotation.

FIG. 34 shows the continued clockwise rotation of the carriage assembly 500. The motion of the carriage assembly 500 and the inertia of the loaded slush container 400 cause the slush container 400 to be cradled between short pin 530 and spacer tube 542. The gap between reference line 564 and dashed perpendicular line 560 stays at an angle B relative to the carriage while in contact with short pin 530 and spacer tube 542. Note that the slush container 400 is lifted up and is not currently supported by support plate 556.

At some point during the rotation of the carriage assembly 500, the slush container 400 will slip relative to short pin 530 and contact the support plate 556 again as shown in FIG. 35. Note that the center of gravity of the slush container 400 is relatively far to the right of the contact between short pin 530 and the slush container 400 so the tendency to rotate about short pin 530 is reduced. Testing has shown that this slipping (instead of rotation about short pin 530) is more pronounced with lower friction between the slush container 400 and short pin 530. Short pin 530 may be a stainless steel pin turned by a lathe although other materials may be used. For typical conditions, the additional rotation of the slush container 400 relative to the carriage assembly 500 is roughly 10 degrees.

FIG. 35 shows the support plate 556 and thus the carriage assembly 500 at the same location as FIG. 28. However, due to the slush container dynamics described in FIG. 28 through FIG. 35, the slush container 400 has been rotated counterclockwise by about 30 degrees as indicated by the gap between reference line 564 and perpendicular line 560 (angle C). At the start of the sequence at FIG. 28, perpendicular line 560 and reference line 564 overlapped.

Repeating the cycle of carriage movement results in the slush container 400 making a full rotation about the longitudinal centerline 492 of the slush container 400 within the carriage assembly 500 after roughly 12 cycles of the carriage movement described in the FIG. 28 to FIG. 35 sequence. Thus, the stimulus provided to the inner surfaces of the slush container 400 (interior of bottle wall 452, interior side of bottle bottom 448, and interior side of lid 404 (not shown here)) varies over time as different portions of the interior surfaces are subject to the sloshing of the slush/saline/air mixture from the different agitation stimuli described in FIG. 28 through FIG. 35 depending on the current angular rotation of the slush container 400 relative to the longitudinal centerline 492.

Note, while it is advantageous for the slush container 400 to start each agitation cycle at a different starting angle than the previous cycle, it is not critical that the offset from cycle to cycle is 30 degrees or any particular fraction of 360 degrees. Likewise, it is not necessary for the amount of rotation cycle to cycle to remain constant throughout the slush making process as the reaction of the slush container 400 with little or no frozen slush may be different to the reaction of the slush container 400 once most of the saline has been converted to slush.

Focus on the Top End of the Slush Container.

Turning to FIG. 36, in addition to the stimulus provided to the bottom end 498 of the slush container 400 by the interaction with the carriage assembly 500 as discussed above, there is stimulus provided to the lid end 494 of the slush container 400 through the use of the front plate 520. As previously described, front plate 520 is connected to back plate 516 by a set of five spacer tubes 542, 544, 546, 548, and 550. The front plate 520 rotates with the carriage assembly 500 around the center of rotation 592 which runs through shaft 506 discussed above.

FIG. 36 shows the front plate 520 of the carriage assembly 500. The front plate 520 may be made of polycarbonate or other suitable material. Having a transparent or near-transparent material facilitates viewing the slush in a substantially transparent slush container 400 but is not strictly required. It is desirable for the opening 524 in the front plate 520 to have smooth surfaces that will not grab or unduly wear the slush container 400.

The bottom end 498 (FIG. 19) of the slush bottle 440 is inserted through opening 524 in front plate 520 to rest the bottom end 498 on the support plate 556 discussed above. A portion of lid end 494 of the slush bottle 440 rests on the perimeter of the opening 524 of the front plate 520. The opening 524 is not a simple circle but is designed to have two separate portions (526 and 528) that substantially match the diameter of the slush container 400 for the portion of the slush bottle 440 that rests in the front plate 520. See top thickened region 480 in FIG. 18. As mentioned above, the portion of the slush bottle 440 that will be contacting the front plate 520 may be thicker than the portion of the slush bottle 440 between the front plate 520 and the head 534 of the short pin 530. Compare thin middle region 476 in FIG. 18 to the nearby top thickened region 480 and the lower thickened region 472. As the interior of the slush bottle 440 is substantially uniform in diameter with a slight taper from bottle bottom 448 towards the lid end 494, any increases in thickness come from expanding the wall thickness of the slush bottle 440.

The wall thickness in middle region may be in the range of 0.04 inches and possibly thinner if the slush bottle 440 is sufficiently rigid with such a thin wall. In contrast, the wall thickness may be double 0.04 inches at places that would experience wear during repeated uses such as top thickened region 480 and lower thickened region 472. About twice as thick provides a nice balance between providing greater durability while still allowing heat transfer even through the thicker walls. The upper expanded region 488 and lower expanded region 464 are thicker still at approximately 0.2 inches thick. These thicker areas facilitate the having a rigid threaded region for receiving the threaded lid 404 and for engagement with the carriage assembly 500. One of skill in the art will recognize that the slush bottle 440 may be created in a mold process that needs a minimum wall thickness in excess of 0.08 inches and then processed by lathe or other process to thin the walls down to 0.08 or 0.04 or some other required thickness.

FIG. 37 shows two circles (426 and 428) that match up with the two separate portions (526 and 528) of the opening 524. The solid line circle 428 is shown concentric with a portion 528 of the opening 524 that is slightly to the right and lower than the portion 526 that is concentric with the dashed line circle 426.

FIG. 38 shows the carriage assembly 500 in the same starting position as FIG. 28. A slush container 400 with a longitudinal centerline 492 of slush container 400 and reference line 566 similar to the reference line 564 shown in FIG. 28 are shown. The difference between reference line 566 and reference line 564 is that reference line 564 is on the bottle bottom 448 of the slush bottle 440 and the reference line 566 is a construction line and applies to a portion of the slush bottle 440 close to the open top of the slush bottle (open until covered with lid 404 not shown here).

The carriage assembly 500 first rotates clockwise to the position shown in FIG. 39 that corresponds to the same carriage position as FIG. 29. Since the slush container 400 is cradled in the opening 524 of the front plate 520, the lid end 494 of the slush bottle 440 tends to stay in the cradled position and rotate with the front plate 520 such that there is not relative motion between the slush bottle 440 and the carriage assembly 500. However, note that FIG. 29 shows that the bottom end 498 of the slush bottle 440 tends to roll because of contact with the support plate 556. The result is that the magnitude of the Angle A shown in FIG. 29 is reduced from what it would have otherwise been if not for tendency of the lid end 494 of the slush bottle 440 to stay fixed relative to the front plate 520. By resisting clockwise rotation, the front plate 520 effectively adds to the net counterclockwise movement of the slush container 400 from a rotation cycle of the carriage assembly 500.

FIG. 40 shows the front plate 520 rotated counterclockwise relative to the starting position, but with a rotation directly opposite to that shown in FIG. 38. This corresponds to the FIG. 30 position. FIG. 40 also shows a dashed perpendicular line 560 and Angle A that matches the Angle A in FIG. 30. However, the reference line 566 on the slush bottle 440 is shown to be at the original starting position. This is done to illustrate that the way the slush bottle 440 is cradled by the front plate 520 makes the lid end 494 of the slush bottle 440 tend to have no relative motion relative to the front plate 520 even though the bottom end 498 of the slush bottle 440 tends to have had a rotation displacement of Angle A at this point in the rotation. The actual angle A will be somewhere between the reference line 566 and the dashed perpendicular line 560 and will depend on the dynamic of the fluid or slush inside the slush container 400 and the fiction between the slush container 400 and the contact points of the carriage assembly 500.

FIG. 41 shows the carriage assembly 500 rotated further in the counterclockwise direction. FIG. 41 corresponds to a rotation position somewhere between FIG. 31 and FIG. 32. In FIG. 41, the center of the slush container 400 is just to the right of the transition point 522 between the two portions 526 and 528 in the front plate 520.

As the carriage assembly 500 continues to rotate counterclockwise toward the position shown in FIG. 42, the slush bottle 440 rolls over the transition point 522. This occurs at roughly the same time that the bottom end 498 of the slush bottle 440 rolling to the left and contacting short pin 530 as shown in FIG. 32. The result is that the rotational momentum of the loaded slush container 400 and the combined dynamics of the slush container 400 contacting short pin 340 and crossing the transition point 522 in the front plate 520 causes a relative spinning of the slush container 400 in the counterclockwise direction relative to the front plate 520. The movement of the lid end 494 of the slush bottle 440 over the transition point 522 of the front plate 520 serves to raise the lid end 494 of the slush bottle 440 relative to the bottom end 498 of the slush bottle 440 to move the air gap 112 along the uppermost portions of the of the slush container 400 towards the lid end 494.

FIG. 43 shows the carriage assembly 500 rotated clockwise back to the starting position that corresponds with FIG. 38. The slush bottle 440 slides over the transition point 522 in the opening 524 of the front plate 520 as the carriage assembly 500 rotates from the position shown in FIG. 42 to FIG. 43. The lid end 494 of the slush bottle 440 tends to slide more than roll due to similar dynamics as described above for the bottom end 498 of the slush bottle 440.

At the end of one cycle of the movements of the carriage assembly 500, the slush container 400 has rotated relative to the carriage assembly 500 by about 30 degrees as shown in FIG. 43.

Repeating the process will cause the slush container 400 to rotate approximately one revolution per twelve cycles of movement of the carriage assembly 500. As noted above, the rotation of the slush container 400 will cause different portions of the substantially cylindrical inner wall of the slush bottle 440 to receive different types of stimulus in the twelve different cycles of movement of the carriage assembly 500.

The movement of the lid end 494 of the slush bottle 440 relative to the bottom end 498 of the slush bottle 440 provides agitation of the two ends of the slush container 400. Thus the interior of the slush bottle 440 at the bottle bottom 448 and the interior of the lid 404 of the slush container 400 will have different portions exposed to the air bubble sloshing as the slush container 400 rotates during the twelve carriage cycles.

Impacts to the Slush Container.

In addition to the reversals of rotational direction, the bottom end 498 of the slush bottle 440 makes impact at different times during the cycle with short pin 530, spacer tube 542, and spacer tube 544. Slush bottle 440 is lifted off of support plate 556 and then impacts support plate 556 as well.

The lid end 494 of the slush bottle 440 rolls over the transition point 522 twice during the carriage cycle to provide additional agitation as the slush container 400 is lifted and dropped.

Slush Freezer Operation.

The slush freezer 300 may have more than one carriage assembly 500 for receipt of a slush container 400 for cooling and slush formation. Each carriage assembly 500 may be moved independently to provide oscillation to the cooling slush/saline mixture. Isolation walls may be used to allow the ambient air around one carriage assembly 500 to be held at a different temperature from the ambient air surrounding a different carriage assembly 500. The slush freezer 300 may be set up to operate in three distinct modes.

Standby Mode.

During standby mode, the cooling compartment, including the components and the ambient air are cooled to a low temperature in preparation for producing slush. This allows the operation during slush making mode to work to chill the liquid to form slush without having to simultaneously cool the cooling compartment. The slush freezer 300 may have sufficient cooling capacity to chill all slush making compartments to the optimal temperature within about twelve to fifteen minutes of operation in standby mode. The standby mode may have a target temperature of the cooling compartment of −20 degrees C. The carriage assembly 500 does not need to move during standby mode and internal lights do not need to be on.

Slush Making Mode.

During slush making mode, the carriage assembly 500 oscillates to oscillate slush within the slush container 400 as discussed above. A light may be turned on to allow operators to see the formation of slush through the walls of the slush container 400 and the clear access door 314 to the cooling compartment 304. The controls of the slush freezer 300 may operate to keep the temperature of the cooling compartment in the range of −27 degrees Celsius to −23 degrees Celsius. The term range as used in this application includes the concept of a fixed set point. Thus one control system may implement a sawtooth thermal treatment to keep the operation within a range of −27 degrees Celsius to −23 degrees Celsius while another control system attempts to maintain the temperature at −25 degrees Celsius. In the latter case, the range would be the single number −25 degrees Celsius.

The use of refrigerated saline at approximately 3 degrees Celsius rather than room temperature sterile saline allows the slush making process to take less time as the sterile saline is close to a temperature where freezing will occur. Likewise, the use of the slush freezer 300 to make slush without an adequate cooling of the cooling compartment 304 during standby mode make cause the slush making process to take additional time. Use of a liquid with more additives than traditional surgical saline may cause the slush making process to take additional time. A user may simply initiate a second slush making cycle to get extended time if needed for complete slush production. Alternatively, if the standard process is to use room temperature saline or liquids with more additives, the timer for the slush making cycle may be adjusted accordingly.

Those of skill in the art will recognize that an impingement plate or other mechanism to divert cool air to strike the outside walls of the slush container 400 may be useful in promoting cooling of the slush.

Maintain Mode.

During the maintain mode, the system temperature within cooling compartment 304 is regulated to help maintain the quality of slush for an extended period of time. The temperature within the cooling compartment 304 may be cycled to maintain high quality slush. For example, the temperature may be cooled down to −6° degrees Celsius when the temperature reached −2 degrees Celsius. As the liquid that remains after the production of surgical slush has a high concentration of salt, temperatures slightly below 0° degrees Celsius do not freeze the remaining liquid.

The carriage assembly 500 may be oscillated for a short period every few minutes to help keep the slush stirred. As the process using a known quantity of saline of a known salinity pre-chilled to a specific temperature, within a known container, in a chamber reliably chilled to a specific temperature during standby mode is going to reliably produce the desired quantity of saline slush in a known time period, the slush freezer unit may be programmed to automatically switch to maintain mode after that period. A control switch may be provided to allow a manual move to maintain mode, such as might be useful if a partial load of saline was chilled to make slush.

Alternatively, the maintain mode may continue the oscillations unabated but merely change the target temperature range. Having the oscillations run only periodically during the maintain mode reduces the production of noise and thus may be desirable.

Operation Sequence.

FIG. 44 provides a high-level overview of a process 1000 to make surgical slush.

Step 1004—Provide power to slush freezer 300.

Step 1008—Set the slush freezer 300 in Standby Mode to cool the cooling compartment 304 to receive the slush container 400 with pre-chilled saline.

Step 1012—Place a prescribed volume of chilled surgical saline into an open slush bottle 440. To promote mixing of the slush container contents, the volume of saline placed into the slush bottle 440 will not fill the slush bottle 440. Thus, one liter of chilled surgical saline may be placed in an open surgical slush bottle 440 having an interior volume of 1.3 liters. This will leave the slush bottle 440 with air above the volume of surgical saline as having a quantity of air in the oscillating container helps with the mixing process.

Step 1016—Put lid 404 on slush bottle 440 to form a sealed slush container 400. The slush bottle 440, lid 404 and the bottle of sterile saline start out in the sterile field and all parts are sterile. Once the sterile slush bottle 440 is partially filled and the lid 404 is placed on the slush bottle 440, the sterile slush container 400 is passed out of the sterile field. Now the outside of the slush container 400 is no longer considered sterile and the cooling compartment 304 of the slush freezer 300 is not sterile. However, the interior of the slush container 400 and the saline/slush within remains sterile.

Step 1020—Insert the slush container 400 with sterile saline into carriage assembly 500 in the chilled cooling compartment 304 and close the access door 314. The slush container 400 is inserted with the lid 404 closest to the access door 314 and the bottle bottom 448 of the slush bottle 440 placed distal to the access door 314.

Step 1024—Close access door 314.

Step 1028—Place the slush freezer 300 in slush making mode.

As the saline is chilled to form slush, the slush container 400 is oscillated so that slush that forms on any interior surface of the slush container 400 is agitated by the movement of the saline/slush/air contents of the slush container 400 and the slush is removed from the interior surface of the slush container 400. Having a smooth, hydrophobic material to form the inside wall of the slush container 400 combined with a lack of sharp corners in the inner surface of the slush container 400 helps keep the slush from staying for an extended period on a portion of the inner surface of the slush container 400. In this instance, smooth is lacking in scratches or imperfections, including imperfections from the manufacturing process. Imperfections such as stretch marks from the molding process which are too small to see without assistance could provide a place for ice crystals to cling to the walls and be more difficult to dislodge. Having eccentric oscillations or other complex movements rather than constant rotation around the longitudinal centerline 492 of the slush container 400 promotes mixing and avoids development of a frozen central core.

Step 1032—Wait as the closed slush container 400 is oscillated while a slush slurry is formed within the closed slush container 400.

Step 1036—Optional Step—Switch to Maintain Mode. After a specific time period, the slush freezer 300 may automatically switch this cooling compartment 304 to maintain mode. Alternatively, the change to maintain mode may be done manually. During the maintain mode, the system temperature within cooling compartment 304 is regulated to help maintain the quality of slush for an extended period of time. One of skill in the art will recognize the advantages of a maintain mode but will recognize that a slush freezer may be created without a maintain mode if the operators remove the slush container from the slush freezer after an appropriate time in slush making mode. The operators may also manually adjust the temperature settings for the slush freezer to maintain the slush till needed.

Step 1040—Opening the access door 314 for the cooling compartment 304 containing the slush container 400 stops the oscillation of the slush container 400 even if the maintain mode is undergoing one of the periodic oscillation periods.

Step 1044—Remove the slush container 400 from the cooling compartment 304 and remove the lid 404 to the slush container 400.

Step 1048—Remove lid from the slush container.

Step 1052—Make slush slurry available for use. The contents of the slush container are sterile and may be passed to a basin or other container in the sterile field using standard hospital procedures.

As the cooling compartment 304 is an appropriate temperature for use in chilling a new batch of saline, a new sterile slush container 400 loaded with pre-chilled saline may be placed in the cooling compartment and immediately placed into slush making mode to create another quantity of surgical slush.

Alternative Process to Pass Surgical Slush to the Sterile Field.

FIG. 45 provides a high-level overview of a process 2000 to deliver surgical slush into a sterile field. Passing surgical slush into a basin in the sterile field may be a challenging task. Unlike pouring a fluid which can be moderated by the tilt angle of the open container, pouring the semi-solid slush slurry out of an open mouth container can be a binary event where nothing comes out until the entirety of a clump of slush slurry comes out. The release of a large mass of slush can cause splashing or spillage of sterile materials from the target basin in the sterile field. Such splashing or waste is undesired.

Step 2004—Remove the lid from the closed slush container after removal of the slush container from the cooling compartment of the slush freezer. Keep the slush container substantially upright so that slush material does not leave the open end of the slush bottle after the lid is removed from the slush container.

Step 2008—Squeezing the middle 496 of the open slush bottle 440. Squeezing the middle 496 of the open slush bottle 440 allows a user to reduce the cross sectional area of the open slush container to prevent a rapid slide of all contents out the open mouth of the slush bottle 440.

Step 2012—Tilt the open slush bottle 440 to direct the open end of the slush bottle towards the target.

Step 2016—Allow some slush located between the squeezed middle and the open top to leave the slush bottle 440. As the open end of the slush bottle 440 is lowered to release slush, some slush will break away from the mass of slush as the mass of slush from the squeeze point to the bottle bottom 448 of the slush bottle 440 is retained by the reduction in inner cross section of the middle 496 of the slush bottle 440 from the squeeze.

Further tilting of the open end of the slush bottle 440 downward may cause additional slush to release from the retained mass. Having a slush bottle 440 that is sufficiently translucent to allow the clump of surgical slush to be seen through the slush bottle 440 walls is helpful with this process. One of skill in the art will recognize that transparent would fall within sufficiently translucent for this purpose. One of skill in the art will recognize that portions of the slush bottle 440 may be substantially opaque as long as there are sufficient portions of the slush bottle that are substantially translucent to allow for identification of the position of the clump of surgical slush.

Step 2020—Optional step—Increase squeeze on the slush bottle 440 to cause some slush to break off and leave the slush container.

Step 2024—Place open slush bottle close to horizontal.

Step 2028—Allow retained slush to move towards open end of slush bottle. Slowly reducing the amount of squeeze while the open end of the slush bottle 440 is only slightly below horizontal will allow the mass of slush to move slowly towards the open end of the slush bottle 440.

Step 2032—Squeeze to retain a fraction of the slush still in the open slush bottle. Increasing the amount of squeeze will now retain a fraction of the slush mass as the distal end of the slush mass has moved from the bottle bottom 448 of the slush bottle 440 but is still precluded from leaving the open slush bottle 440.

Step 2036—Tilt open end of slush bottle 440 towards target basin.

Step 2040—Allow slush between squeezed portion and open end to break off and leave the mass of slush retained by the squeeze.

Step 2044—Optional step—Increase squeeze on the slush bottle to cause some slush to break off and leave the slush container and enter the target basin while some slush is retained between the squeeze and the bottle bottom 448 of the slush bottle 440.

Step 2048—Slowly removing the squeeze will allow the slush bottle 440 to return to the original shape and release the remaining slush.

Those of skill in the art will recognize that the teachings with respect to the delivery of slush to the sterile field may be modified by adding steps which initially provide a squeeze towards the lid end of the middle 496 for an initial delivery of slush followed by one or more subsequent deliveries from setting the slush bottle in a substantially vertical orientation, releasing the squeeze and then imposing a squeeze closer to the bottle bottom 448 of the slush bottle 440 before tiling the slush bottle 440 to deliver more slush.

Material Choices.

Slush containers 400 made of highly hydrophobic materials with smooth surface finishes work well for the teachings of the present disclosure. Thus, material choices made with or coated with Teflon® material work well in the context of this disclosure. Coatings will work well but may not be ideal choices for slush containers that are intended to go through multiple sterilization and use cycles as any scratches or removal of coating may cause slush to adhere to the underlying material. Thus, slush containers made of a hydrophobic material are preferred over slush containers with coated interiors.

The term Teflon materials is actually an imprecise statement. E.I. DuPont De Nemours and Company Corporation ("DuPont") owns a series of registered trademarks for various uses of material containing polymers of fluorinated hydrocarbons. There are actually several different materials that fall within this category of materials covered by the Teflon mark. The materials that fall within the category of materials covered by the Teflon mark may also be provided by other sources of goods. Thus, a focus on the chemical names, rather than the trademarked product names is appropriate. Those of skill in the art will appreciate that the production of medical components often uses a medical grade supply that is created under more stringent process controls and has less impurities. Medical grade resin may be used here to make the containers.

Polytetrafluoroethylene (PTFE) is the most commonly provided material under the Teflon trademark and is often mistakenly associated by the public as synonymous with Teflon® material. Other materials sold under the Teflon name are a class of perfluoroethers. Prominent in the perfluoroether materials is perfluoroalkoxy alkanes (PFA). http://www.guarniflon.com/index.php/en/materials/pfa.html. There are other materials in this group that have different ratios of PTFE and methylvinylether (MVE). One such material is known as MFA. http://www.guarniflon.com/index.php/en/materials/mfa.html.

PFA like PTFE is known for resistance to chemicals (chemically inert), hydrophobic, and having extremely low coefficients of friction. One way that PFA is superior to PTFE is that PFA polymer may be melt processed which is useful when seeking to create slush containers by injection molding. Another drawback of PTFE is that it is less dimensionally stable that PFA. Dimensional stability rather than a tendency to creep is useful when a slush container is being used through multiple sterilization cycles so that a slush container lid continues to fit all the different slush containers that just underwent sterilization.

Another material in the Teflon family that may be injection molded is FEP (Fluorinated ethylene propylene) which is a copolymer of hexafluoropropylene and tetrafluoroethylene. FEP differs from the PTFE (polytetrafluoroethylene) resins in that it is melt-processable using conventional injection molding and screw extrusion techniques (see http://en.wikipedia.org/wiki/Florinated_ethylene_propylene).
This material has been tested and found to be viable for use in slush containers used in accordance with the teachings of this disclosure. PFA is preferred over FEP as PFA is harder and more dimensionally stable than FEP.

While PFA and FEP are preferred materials, acceptable results may be obtained with PET (sometimes called PETE) or with the related material PETG (PETG (Polyethylene Terephthalate Glycol-Modified). The differences between PET and PETG are summarized at http://www.plasticingenuity.com/packaging/differences-between-petg-and-apet/.

As such containers made with PFA, FEP, or other suitable materials are hydrophobic and have extremely low surface friction, ice crystals tend not to form or stick to the walls of the slush container. The coefficient of friction (both static and dynamic) for various products know as Teflon including PTFE, FEP, and FPA are extremely low relative to other solid materials. The use of containers made from materials that tend not to have ice crystals adhere to the walls of the slush container promotes mixing when used in connection with an oscillating agitation.

Having a situation where ice does not form on the container wall, and mixing keeps ice from building up close to the wall more than near the longitudinal centerline of the container allows use of a slush making machine with ambient air that is chilled well below the freezing temperature range for the saline. Reducing the ambient air temperature increases the rate of cooling of the container contents which is desirable when done without the adverse consequences of creating unacceptable ice deposits on or near the walls of the slush container 400.

The material choice for the container may allow sterilization of the container per standard hospital protocols. Those of skill in the art recognize that there are a number of different protocols and some may be contraindicated for certain materials. Examples of common sterilization protocols include using EtO (ethylene oxide), autoclave, and low temperature plasma. Other methods are known to those of skill in the art.

Non-Oscillating Embodiment.

FIG. 46 is perspective view of a carriage assembly 700 with slush container 800. Slush container 800 has many attributes of slush container 400 including having a slush bottle 840 with a wide open mouth and a lid 804 that engages threads at a lid end 894 of the slush bottle 800. The bottle wall 852 of slush bottle 800 lacks many of the outer diameter and wall thickness changes found in slush container 400. (Compare FIG. 18) Thus, the inner wall and outer wall of the slush bottle 840 is relatively straight except for a small taper that increases from the bottom end 898 to the lid end 894.

The carriage assembly 700 is driven by a motor 504. The motor rotates a shaft 506 based upon a ratio of motor pulley 730 to shaft pulley 734. A drive belt 738 may be used to transfer rotational motion from the motor pulley 730 to the shaft pulley 734. The drive belt may be a round belt which would slip should someone grab the rotating carriage assembly 700.

The carriage assembly 700 has a back plate 716, a distal plate 760 and a front plate 720. The front plate 720 and distal plate 760 have openings to allow a bottle bottom (not shown here) of slush container 800 to be inserted through the carriage assembly 700 to rest on or near the back plate 716. The spacing of the distal plate 760 and front plate 720 relative to the back plate 716 is maintained by a set of spacer tubes. In this view, spacer tubes 742, 750, and 754 are visible and spacer tube 748 is behind the slush container 800. The number of spacer tubes could be more or less than four.

The stimulus provided to the sterile saline 108 and air gap 112 within slush container 800 includes:
- rotation of the slush container 800 along the longitudinal centerline;
- movement of the air gap 112 from the bottom end 898 to the lid end 894; and
- thumps to the bottle wall 852 imparted by the movement of the slush container 800 within the carriage assembly 700.

FIG. 47, FIG. 48, and FIG. 49 show clockwise rotation of the front plate 720 is indicated by spacer tubes 742, 746, 750, and 754. A cross section of slush container 800 shows sterile saline 108 (which over time includes a growing percentage of surgical slush) and air gap 112. Note that the clockwise rotation of carriage assembly 700 will impart a clockwise rotation upon slush container 800. As the outer diameter of the slush container 800 is less than the inner diameters of the front plate 720 and the distal plate 760, the speed of rotation of the slush container 800 will be greater than the speed of rotation of the carriage assembly 700.

The front plate 720 has a pair of humps 724 and 728. As hump 728 comes in contact with slush container 800, the slush container 800 is lifted by the hump 728. As the front plate 720 continues to rotate, the slush container 800 loses contact with the hump 728 and falls to make contact with a non-hump portion 732. This sudden contact of non-hump portion 732 jars free slush 190 that may have momentarily adhered to the inner walls of the slush container 800. The cycle of lift and drop to jar slush 190 from the inner walls of slush container 800 is repeated as hump 724 eventually rotates to lift the slush container 800.

While the front plate 720 is shown with two humps 724 and 728, the front plate could have a single hump or could have more than two humps. As the slush container 800 needs to fall and contact a non-hump portion 732, the number of humps will be limited. A larger number of humps are possible if the difference between the outer diameter of the slush container 800 and the inner diameter of the front plate 420 is increased.

Note that as the slush container 800 only makes contact with the apex of the hump, the precise shape of the hump is not important as long as the overall width of the hump is not made so wide that the slush container 800 falls to be quickly lifted and dropped.

FIG. 50 is a front perspective view of the carriage assembly 700 without a slush container 800. Spacer tube 742 is aligned with hump 724 on front plate 720. Spacer tube 746 is aligned with hump 764 on distal plate 760. Spacer tube 750 is aligned with hump 728 on front plate 720. Spacer tube 754 is aligned with hump 768 on distal plate 760. Alignment of the spacer tubes with the humps is not required. The number of spacer tubes does not need to correspond to the total number of humps. From FIG. 50, one can discern that the humps 724 and 728 on the front plate 720 are out of phase with the humps 764 and 768 on the distal plate 760. This different in phase allows the air gap 112 within the slush container 800 to move from the bottom end 498 towards the lid end 494 and back as the sequence of humps lift the two ends of the slush container to vary which end of the slush container is the most elevated. To be most effective in moving the air gap 112, the longitudinal centerline 492 of the slush container 800 should be close to horizontal when the slush container 800 is not in contact with any hump.

To bias the slush container 800 against sliding forward relative to the front plate 720, the longitudinal centerline 492 between humps may be biased to provide a slight tendency to move towards the back plate 716. The front humps 724 and 728 will be sufficient to move the air gap towards the lid end 494 if the bias is not overwhelming.

The bias towards the back plate 716 may be achieved by placing the shaft 506 (See FIG. 46) at a slight angle with respect to horizontal. Alternatively, the bias towards the back plate 716 may be achieved by having the inner diameter of the distal plate 760 larger than the inner diameter of the front plate 720 so that the bottom end 498 is biased lower than the lid end 494.

Many Options to Bias Slush Container Position.

A careful observer will notice that in many of the drawings, the inner diameter of the front plate 720 is greater than the inner diameter of the distal plate 760. This is an artifact from an upgrade to legacy equipment that had the shaft at an upward angle. The reversed combination of inner diameters is used to partially offset the legacy upward angle of the carriage assembly. One of skill in the art will understand that the teachings of this disclosure call for having a longitudinal axis of a slush container 800 at close to horizontal so that stimulus applied to the slush container 800 will cause the air gap to move from the bottom end 498 to the lid end 494 and from the lid end 494 to the bottom end 498.

Note that one of skill in the art will recognize that in some instances a retrofit of a legacy machine with a substantial slope of the shaft 606 with respect to horizontal may not be fully offset with the openings in the front plate 720 and distal plate 760. Thus, for some slush making machines, the air gap 112 may not reach the surface at the bottom of the slush container 800. While this situation will lack optimal mixing and may result in some clumping of slush at the bottom end of the slush container 800, the majority of the slush container 800 provides useful slush and thus such a system may be used. This situation highlights the value of having the air gap 112 move from end to end to promote mixing and break up any ice formations but shows that sometimes a suboptimal but viable solution that does not fully implement the teachings of this disclosure may be implemented.

The need for retaining the slush container 800 in the carriage assembly 700 is heighted by the momentum of the sterile saline 108 as the lifting and dropping of the ends (894 and 989) of the slush container 800 causes movement of not just the air gap 112 but the momentum from the movement in the opposite direction of sterile saline 108 which periodically impinges upon the inside of the lid 404. Thus, it may be desirable to bias the carriage assembly 700 so that the slush bottle away from the lifting of humps is tilted about 2 degrees with the bottom end 498 lower than the lid end 494.

Air Gap Movement.

A series of figures (FIG. 51, FIG. 52, FIG. 53, and FIG. 54) each show a side view of a slush container 800 in a carriage assembly 700. To assist with the conveyance of information, spacer tube 746 has been colored sold black. In FIG. 51, spacer tube 746 is at 12 o'clock and the bottom end 498 of the slush container 800 is elevated by hump 768 (See FIG. 50).

In FIG. 52, spacer tube 746 is at 3 o'clock and thus behind the slush container 800. Spacer tube 742 is at 12 o'clock and the lid end 494 of the slush container 800 is elevated by hump 728 (See FIG. 50).

In FIG. 53, spacer tube 746 is at 6 o'clock. Spacer tube 754 is at 12 o'clock and the bottom end 498 of the slush container 800 is elevated by hump 764 (See FIG. 50).

In FIG. 54, spacer tube 746 is at 9 o'clock. Spacer tube 750 is at 12 o'clock and the bottom end 498 of the slush container 800 is elevated by hump 724 (See FIG. 50).

The pattern repeats as the clockwise rotation of the carriage assembly 700 continues.

Migration of Stimulus.

Having the slush container 800 move at a different rate than the carriage assembly 700 helps provide stimulus to different surfaces of the slush container over time. Thus the lift and drop stimulus from the humps and the sloshing of the sterile saline 108 made possible by the air gap 112 impacts different surfaces over time.

A series of figures helps illustrate this concept. See FIG. 55-64. The figure on the left side of each pair of figures shows a cross section of the slush container 800 resting within the distal plate 760. Spacer tube 746 is shown in black. An index mark 790 is added to the figures to show relative movement of the slush container 800 versus the carriage assembly 700. The longitudinal centerline 792 for the slush container 800 is shown in each drawing of the drawing pairs. Construction lines help illustrate the differences in elevation of the longitudinal centerline 792 of the slush container 800 at the distal plate 760 and front plate 720.

To allow a discussion of the concept of staggered application of stimulus and the difference in rotation rate between the slush container 400 and the carriage 700, FIG. 55-64 has been drawn to show the slush container 400 lifted when the hump is at 6 o'clock. As shown in sequence FIG. 47 to FIG. 49, the actual process is apt to have the slush container 400 lifted over the hump when the hump is at 7 o'clock.

FIG. 55 and FIG. 56 illustrate spacer tube 746 at 12 o'clock with index mark 790 at 12 o'clock. Hump 768 elevates the longitudinal centerline 792 of the slush container 800 so that the bottom end 898 is above the lid end 894. (See FIG. 46)

FIG. 57 and FIG. 58 illustrate spacer tube 746 at 3 o'clock with index mark 790 at 3:30 rather than 3 o'clock. Hump 728 elevates the longitudinal centerline 792 of the slush container 800 so that the lid end 894 is above the bottom end 898.

FIG. 59 and FIG. 60 illustrate spacer tube 746 at 6 o'clock with index mark 790 at 7 o'clock. Hump 764 elevates the longitudinal centerline 792 of the slush container 800 so that the bottom end 898 is above the lid end 894.

FIG. 61 and FIG. 62 illustrate spacer tube 746 at 9 o'clock with index mark 790 at close to 10:30. Hump 724 elevates the longitudinal centerline 792 of the slush container 800 so that the lid end 894 is above the bottom end 898.

FIG. 63 and FIG. 64 illustrate spacer tube 746 back at 12 o'clock. Note that the index mark 790 is not back at 12 o'clock. The index mark 790 is at approximately 2 o'clock. As before, hump 768 elevates the longitudinal centerline 792 of the slush container 800 so that the bottom end 898 is above the lid end 894.

The precise amount that the rotation of the slush container 800 exceeds the rotation of the carriage assembly 700 will vary with the relative diameters. However, it is an advantage of the disclosure to have relative movement so that stimulus is not repeatedly applied to only a subset of the inner walls of the slush container 800.

Note that depending on the thickness of the walls of the slush container 800 and the material choice, there may be some localized flexing of the slush container 800 as the humps are lifting the slush container 800 or as the slush container 800 impacts the front plate 720 or distal plate 760 after falling. This additional stimulus is helpful for creating a weak zone in any thin film of ice crystals forming on the interior of the slush container 800. The movement of the rotating slush contained within the sterile saline 108 as the air gap 112 is rotated around the interior of the slush container 800 and moves from end to end of the slush container 800 works to scrub off ice crystals from the interior of the slush container 800.

The repeated lift and drop stimulus applied to each end of the slush container 800 provides additional assistance in getting thin films of ice crystals to drop away from the low friction, hydrophobic surfaces.

Operation Sequence.

A slush freezer may have one or more cooling compartments. If the slush freezer has more than one carriage assembly 700 driven by one motor 504, then the commonly driven slush carriages 700 may be in a common cooling compartment or may be separate compartments provided with the same cooling sequence.

For example, a single motor 504 may drive a drive belt 738 that in turn drives four shaft pulleys 734, and ultimately four carriage assemblies 700. If one motor 504 is driving more than one carriage assembly 700, then the process for producing slush may be modified slightly from the process 1000 set out above.

FIG. 65 provides a high-level overview of a process 3000 to make surgical slush where one motor drives more than one carriage assembly 700.

Step 3004—Provide power to slush freezer. The slush freezer may have one or more cooling compartments. Each cooling compartment may have one or more carriage assembly 700. Each cooling compartment may have one or more access doors.

Step 3008—Optional Step—Set the slush freezer in Standby Mode to cool the cooling compartment to receive the slush containers 800 with pre-chilled saline. While this step is optional, the time required to produce slush is reduced by cooling to slush freezer before the start of slush making.

Step 3012—Place a prescribed volume of surgical saline into an open slush bottle 440. To promote mixing of the slush container contents, the volume of saline placed into the slush bottle 440 will not fill the slush bottle 440. Thus, one liter of chilled surgical saline may be placed in an open surgical slush bottle 440 having an interior volume of 1.3 liters. This will leave the slush bottle 440 with air above the volume of surgical saline as having a quantity of air in the oscillating container helps with the mixing process. Preferably, the surgical saline is pre-chilled before use added to an open slush bottle. Again while pre-chilling the saline is preferred as it allows for more rapid production of slush, the process will work with saline at ambient air temperature.

Step 3016—Put lid 804 on slush bottle 840 to form a sealed slush container 800. The slush bottle 840, lid 804 and the supply of sterile saline start out in the sterile field and all parts are sterile. Once the sterile slush bottle 840 is partially filled and the lid 804 is placed on the slush bottle 840, the sterile slush container 800 is passed out of the sterile field. Now the outside of the slush container 800 is no longer considered sterile and the one or more cooling compartments of the slush freezer are not sterile. However, the interior of the slush container 800 and the saline/slush within remains sterile.

Note—as discussed elsewhere in this disclosure, pre-filled slush containers may be used and thus the process at the surgical center would not include step 3102 and step 3016.

Step 3020—Insert the slush containers 800 with sterile saline into the one or more chilled cooling compartments and close the one or more access doors. The slush container 800 is inserted with the lid 804 closest to the access door and the bottle bottom of the slush bottle 840 placed distal to the access door.

Step 3024—Repeat until desired number of slush containers 800 are loaded with saline and placed in carriage assemblies 700.

Step 3028—Ensure that the one or more access doors are closed.

Step 3032—Place the slush freezer in slush making mode. As the saline is chilled to form slush, the slush containers 800 receive stimulus from the rotating carriage assemblies 700 as described within this disclosure so that slush that forms on any interior surface of the slush container 800 is agitated by the movement of the saline/slush/air contents of the slush container 800 and the slush is removed from the interior surface of the slush container 800.

Having a smooth, hydrophobic material to form the inside wall of the slush container 800 combined with a lack of sharp corners in the inner surface of the slush container 800 helps keep the slush from staying for an extended period on a portion of the inner surface of the slush container 800. In this instance, smooth is lacking in scratches or imperfections, including imperfections from the manufacturing process. Imperfections such as stretch marks from the molding process which are too small to see without assistance could provide a place for ice crystals to cling to the walls and be more difficult to dislodge.

Step 3036—Wait as a slush slurry is formed within each of the inserted closed slush containers 800.

Step 3040—Optional Step—Switch to Maintain Mode. After a specific time period, the slush freezer may automatically switch to maintain mode. Alternatively, the change to maintain mode may be done manually. During the maintain mode, the system temperature within the one or more cooling compartments is regulated to help maintain the quality of slush for an extended period of time. One of skill in the art will recognize the advantages of a maintain mode but will recognize that a slush freezer may be created without a maintain mode if the operators promptly remove the slush containers from the slush freezer after an appropriate time in slush making mode. The operators may also manually adjust the temperature settings for the slush freezer to maintain the slush till needed.

Step 3044—Opening one or more access doors stops the rotation of the carriage assembly. This may be accomplished by a door open sensor that stops the motor 504. Alternatively, one could use the door open sensor to use a clutch to disengage one or more carriage assembly 700 from the rotating belt. The slush freezer may have a switch used by an operator to stop the carriages from rotation and have the door sensor as a back-up to the switch.

Step 3048—Remove a slush container 800 from the slush freezer.

Step 3052—Remove the lid 804 to the slush container 800.

Step 3056—Make slush slurry available for use. The contents of the slush container are sterile and may be passed to a basin or other container in the sterile field using standard hospital procedures. The process 2000 described in FIG. 45 may be used if desired to deliver portions of the slush. Repeat with additional slush containers as needed.

If not all slush containers 800 are immediately used to deliver slush, the slush containers 800 may be left in the slush freezer until needed.

Step 3060—Repeat steps 3044-3056 as additional slush is needed.

Once all the slush containers 800 with slush have been removed, the slush freezer is available to make additional slush. As the one or more cooling compartments are at an appropriate temperature for use in chilling a new batch of saline, a set of new sterile slush containers 800 loaded with pre-chilled saline may be placed in the slush freezer and immediately placed into slush making mode to create another quantity of surgical slush.

Alternatives and Variations.

Alternative Tops for the Slush Container.

While the interaction between lid 404 and slush bottle 440 has been a threaded engagement in the figures discussed in this disclosure, a threaded engagement is not required. Those of skill in the art will recognize that other options exist for sealing the slush container after sterile saline 108 has partially filled a slush bottle. One example is a pop-off cap that has a ring that must be peeled away. The cap is destroyed during this process and a new cap must be used with each use of the slush bottle. Snap off caps as used in certain pill bottles may be used. Caps may be attached to the slush bottle via a bayonet engagement where a gasket holds one or more pins to maintain the engagement. These examples are not intended to be exhaustive, but merely to show that all that is needed is a sealed top that can be readily opened for delivery of the surgical slush.

Other Drivers of Complex Motion.

Those of skill in the art will recognize that complex agitation to the saline/slush/air contents of a slush container can be achieved by different mechanisms than the example set forth above. Complex agitation for purposes of this disclosure is something other than uniform rotation around the longitudinal centerline 492 of the slush container or non-movement of the slush container in a cooling compartment as those treatments will not provide adequate mixing of the saline/slush/air mixture and will lead to the formation of ice structures incompatible with atraumatic surgical slush.

While those making use of the teachings of the present disclosure are apt to place a carriage within a cooling chamber and impart a set of complex motions to the closed slush container with a carriage that moves, one of skill in the art could place the closed slush container within a cooling chamber, perhaps in a manner where the closed slush container could not move relative to the cooling chamber, and then imparting a set of complex motions upon the cooling chamber to provide the agitation to help dislodge any ice formations that form on the interior of the closed slush container. Those of skill in the art will appreciate that the set of complex motions could be a combination of accelerations imparted to the closed slush container through movement of a carriage within the cooling chamber and accelerations imparted to the cooling chamber.

While the discussion above had the closed slush container cradled within the carriage but able to rotate and translate relative to the carriage, this is not an absolute requirement. One of skill in the art could take the teachings of the present disclosure and have a closed slush container firmly connected to a carriage to preclude movement of the closed slush container relative to the carriage and still impart complex movement to the contents of the closed slush container so that the contents of the closed slush container strike portions of the interior walls of the closed slush container to dislodge ice crystals formed on the interior walls of the closed slush container and promote mixing of the slush slurry.

More than Saline.

While the discussion above had a focus on surgical slush made from sterile saline, the teachings of the present disclosure could be applied to creation of surgical slush that is made of a mixture of medical saline or sterile water and clinically appropriate materials. The clinically appropriate materials may include sugars, vitamins, enzymes, or other bioactive agents. The operation of the slush freezer may need to be adopted for a particular use such as altering the temperature settings of the expected amount of time to create the slush, but these adjustments can be made by those of skill in the art. While it is likely that the primary use of the teachings of the present disclosure would be with sterile saline within a slush container and removable lid where at least the surfaces exposed to the interior of the closed slush container would be sterile, the operation of process to create slush does not require sterile conditions.

Lack of Front Plate.

While some of the example discussed above used a front plate 520 to provide a different set of agitation stimulus to the lid end 494 of the slush container 400 than imposed on the bottom end 498 of the slush bottle 440, a viable process could simply extend the short pin 530 and support plate 556 from the back plate 516 of the carriage assembly 500 to support the lid end 494 of the slush bottle 440. An advantage of the inclusion of the front plate 520 is the lifting action of the transition point 522 on the lid end 494 of the slush bottle 440 end to help move the bubble in the slush container 400.

Non-Circular Cross Section.

While the cross section of the slush container 400 and slush container 800 has been shown as a circle, other shapes are possible including an oval or an extremely rounded tri-lobe or square shape. The shape should avoid the use of sharp corners which might retain slush. Use of shapes other than circular may require adjustments to the rate of cooling or the agitation levels in order to compensate for any tendency of slush to form in the highly rounded corners.

Conduction for Cooling.

The disclosure set forth above addresses cooling principally by convection. Those of skill in the art will appreciate that a process for surgical slush could rely on a process of cooling that involved conduction. For example, the carriage assemblies (500 or 700) could be made of metal or another highly conductive material and have more plates or places for contact between the carriage assembly and the slush container (400 or 800). Fins could be added to the conductive carriage assembly to help the carriage assembly dump heat to the cooling chamber. The moving fins on the carriage assembly could be oriented to pass between stationary fins on the evaporator for rapid heat transfer.

As the thermal mass of the carriage assembly becomes more significant, the value of pre-chilling the cooling chamber before slush production becomes more pronounced.

Those of skill in the art will recognize that other methods of heat transfer including those the immerse the slush container in a media other than air are possible but would tend to lead to more costly slush freezers and some additional steps for the staff.

One of skill in the art will appreciate that increases in the rate of heat transfer including localized areas of enhanced heat transfer may require enhanced agitation of the slush and air gap to avoid ice accumulations on the inner surfaces of the slush container.

Single Use Slush Containers.

While the disclosure teaches the use of slush bottles and lids that may undergo sterilization and reuse, the teachings of this disclosure do not require re-use. Single use slush containers may be used.

Pre-Filled Slush Containers.

While the teachings of this disclosure teach a process that includes partially filling a slush bottle with sterile saline and affixing a lid, the process could be used with pre-filled slush containers having sterile saline within and a suitable air gap. Pre-filled containers would tend to be single-use containers.

Keeping Slush Container in Carriage Assembly.

While the discussion above provided a bias to retain the slush container 800 in the carriage assembly 700, the suggestions were not an exhaustive list. Those of skill in the art will be able to think of several ways to help retain the slush container 800 is the carriage assembly 700 including retainers that are either connected to the carriage assembly 700 and rotate with the carriage assembly 700 or retainers that are fixed and do not rotate with the carriage assembly 700. The retainers may be set to allow for a loading/unloading position where the retainer does not impede movement of the slush container 800 relative to the carriage assembly carriage 700 and a retain position where the retainer does impede the movement of the slush container 800 away from the back plate 716.

No Preference for Clockwise Versus Counterclockwise.

The figures and text describing FIG. 46 through FIG. 64 assumed a direction of rotation in order to explain the complex stimulus. The teachings of the present disclosure work whether the carriage assembly as viewed from the end with the lid 404 is clockwise or counterclockwise.

Speed of Rotation.

The speed of rotation that is selected by one using teachings of the present disclosure will be a function of the entire set of design choices including the rate of cooling, slush container geometry and properties, and details of the carriage assembly including the number of humps. Other factors such as desire to minimize noise may come into play.

A rotation rate for the carriage assembly of 28 RPM is believed suitable for at least some applications although it is believed that a broad range of rotational speeds could be used as long as there is the ability of the slush container to fall after being lifted by the humps. The speed of rotation may not be constant as there may be some advantage to changing the lift/drop stimulus by altering the rotation speed of the carriage.

During a maintain mode, the speed of rotation may be set relatively low, perhaps 1 to 2 revolutions per minute to help keep the prepared slush ready for use.

Non-Oscillating but Maybe not Unidirectional.

While the assembly shown in FIG. 46 has a motor 504 that drives the shaft 506 without oscillation back and forth, it is not required that the motor never change direction. One may choose to have the motor periodically stop and reverse direction. This may have some advantage at dislodging ice crystals on the inner surfaces of the slush container 800 that have been resistant to removal from impinging slush resulting from rotation of the carriage assembly 700 in a first rotational direction. By non-oscillating, it is meant that that rotation is provided for at least two full rotations (likely hundreds of rotations) before stopping and reversing direction. In contrast, oscillating rotation does not move a full rotation in either direction.

Other Forms of Lift Stimulus.

While the embodiment described above made use of one or more humps on the front plate 720 and the distal plate 760, other forms of lift stimulus could be used.

The lift stimulus could be a solenoid or other actuated device which lifts a portion of the slush container 800 upward. This lifting action would not need to be linked to the rotational position of the front plate 720 or the distal plate 760. The stimulus could come less frequently than during every revolution of the carriage assembly 700. The stimulus could start after several minutes of rotation of the slush container 800 in the carriage assembly 700 and the frequency of lift stimulus could be increased or otherwise varied during the slush production cycle.

A cam follower or track follower could be attached to the rotating carriage assembly and provide lift stimulus when the follower is urged radially inward when reaching a portion of the rotation of the carriage assembly.

The carriage assembly 700 could be lifted to change the position of the air gap 112 within the slush container 800.

Instead of relatively narrow humps to lift and drop the slush container 800, one could have one or more extended trough where the slush container 800 drops into the trough for the drop stimulus and rises out of the trough for the lift stimulus. A difference between a hump and a trough is that the slush container must be able to fall into a trough sufficiently wide so that both the leading and trailing side of the slush container is down in the trough. Depending on the relative diameter of the slush container relative to the diameter of the plate, there may only be room for one extended trough. If the diameter of the slush container is made small enough relative to the diameter of the plate, then more than one trough can be implemented. One could use a combination of troughs and humps.

Synchronized Lift/Drop Stimulus.

This disclosure teaches the preference for having lift/drop stimulus including stimulus with a drop followed by a lift. The lift/drop stimulus provides two benefits. One benefit is the alternating incentives to move the air gap towards the bottom end of the slush container 800 and towards the lid end of the slush container 800. Another is the physical shock to the slush bottle which aids in loosening films of ice forming on the various interior surfaces of the slush container 800.

For instance, a partial implementation of teachings of this disclosure may align the humps or troughs of the front plate 720 and distal plate 760 so that both ends of the substantially horizontal slush bottle 840 are lifted or dropped at the same time.

Thus the saline and air gap in the slush container 800 move in a complex set of motions from stimulus applied by the front plate and the distal plate to the closed slush container to periodically drop the closed slush container without changing the relative orientation of the lid end of the closed slush container relative to the bottom end of the closed slush container. In order to periodically drop the closed slush container, the closed slush container would need to be lifted by humps or by the ends of troughs.

The rapid accelerations of the slush bottle in the vertical dimension would tend to disperse the air gap which would then reform only to be dispersed again. It is believed that the overall mixing of the saline once there is a substantial fraction that is slush would be less vigorous than a system with marked changes to the orientation of the slush container 800 with respect to horizontal but this alternative is thought to be viable. One of skill in the art may compensate by slowing the cooling process or increasing the ratio of air to saline in order to compensate. Increasing the magnitude of the lift/drop stimulus may also help with promoting mixing.

APPENDIXES

Appendix A is a pre-release draft of C Change Surgical Operator's Manual with Preventative Maintenance for Slush Freezer Unit Model #SFU-1.5.

What is claimed is:

1. A method for making surgical slush; the method comprising:
    obtaining a closed slush container having contents of liquid saline and an air gap;
    the closed slush container having a set of interior walls including a bottom end surface of the closed slush container and a lid end surface of the closed slush container that are smooth and hydrophobic to resist adherence of ice crystals to the set of interior walls;
    inserting the closed slush container into a cooling compartment with ambient air; and
    moving the closed slush container in a sequence of repeated cycles of complex movements rather than constant rotation around a fixed axis of rotation to impart accelerations on the contents of the closed slush container so the contents of the closed slush container move in a complex set of motions rather than constant rotation around the fixed axis of rotation of the slush container as at least a portion an exterior of the closed slush container is exposed to ambient air cooled below a freezing temperature for the liquid saline contained in the closed slush container as the liquid saline is converted into surgical slush with a mixture of liquid saline and ice crystals.

2. The method of claim 1 wherein the step of obtaining a closed slush container with contents of liquid saline and the air gap is achieved by obtaining a sterile slush bottle with an open lid end and a sterile removable lid;
    partially filling the slush bottle with sterile liquid saline and closing the slush bottle by putting the removable lid on the lid end of the slush bottle to form the closed slush container with contents of liquid saline and the air gap; and
    wherein the sterile liquid saline remains sterile after placement into the slush container and converted into surgical slush.

3. The method of claim 1 wherein:
    inserting the closed slush container into the cooling compartment with ambient air includes placing the closed slush container into a carriage within the cooling compartment; and
    moving the closed slush container to impart accelerations on the contents of the closed slush container so the contents move in the complex set of motions is at least partially accomplished by movements of the carriage within the cooling compartment.

4. A method for making surgical slush; the method comprising:
    obtaining a closed slush container having contents of liquid saline and an air gap;
    the closed slush container having a set of interior walls including a bottom end surface of the closed slush container and a lid end surface of the closed slush container that are smooth and hydrophobic to resist adherence of ice crystals to the set of interior walls;
    inserting the closed slush container into a cooling compartment with ambient air;
    moving the closed slush container to impart accelerations on the closed slush container so the contents of the closed slush container move in a complex set of motions rather than constant rotation around a fixed axis of rotation of the slush container as at least a portion of an exterior of the closed slush container is exposed to ambient air cooled below a freezing temperature for the liquid saline contained in the closed slush container as the liquid saline is converted into surgical slush with a mixture of liquid saline and ice crystals; and inserting the closed slush container into the cooling compartment with ambient air includes placing the closed slush container into a carriage within the cooling compartment;

moving the closed slush container to impart accelerations on the contents of the closed slush container so the contents move in the complex set of motions is at least partially accomplished by movements of the carriage within the cooling compartment; and wherein the closed slush container is partially constrained by the carriage but is able to move relative to the carriage while the closed slush container is subject to movements of the carriage within the cooling compartment.

5. A method for making surgical slush; the method comprising:

obtaining a closed slush container having contents of liquid saline and an air gap;

the closed slush container having a set of interior walls including a bottom end surface of the closed slush container and a lid end surface of the closed slush container;

inserting the closed slush container into a cooling compartment with ambient air;

moving the closed slush container to impart accelerations on the contents of the closed slush container so the contents move in a complex set of motions rather than constant rotation around a fixed axis of rotation of the slush container as at least a portion of an exterior of the closed slush container is exposed to ambient air cooled below a freezing temperature for the liquid saline contained in the closed slush container as the liquid saline is converted into surgical slush with a mixture of liquid saline and ice crystals; and wherein the fixed axis of rotation of the closed slush container is moved during the set of complex motions so that a highest end of the closed slush container moves:

from a bottom end of the closed slush container to a lid end of the closed slush container; and from the lid end of the closed slush container to the bottom end of the closed slush container;

such that movement of the contents of the closed slush container removes ice crystals from:

the bottom end surface of the closed slush container; and from the lid end surface of the closed slush container.

6. A method for making surgical slush; the method comprising:

obtaining a closed slush container having contents of liquid saline and an air gap;

the closed slush container having a set of interior walls including a bottom end surface of the closed slush container and a lid end surface of the closed slush container;

inserting the closed slush container into a cooling compartment with ambient air;

moving the closed slush container to impart accelerations on the contents of the closed slush container so the contents move in a complex set of motions rather than constant rotation around a fixed axis of rotation of the slush container as at least a portion of an exterior of the closed slush container is exposed to ambient air cooled below a freezing temperature for the liquid saline contained in the closed slush container as the liquid saline is converted into surgical slush with a mixture of liquid saline and ice crystals; and wherein the closed slush container is subject to:

a series of repeated cycles of complex movements and within a cycle of complex movements, the closed slush container is rotated in a first rotational direction and a second rotational direction; and the cycle of complex movements includes asymmetric rotation reversals to cause a momentum of the contents of the closed slush container to rotate the contents of the closed slush container more in a one rotational direction selected from the first rotational direction and the second rotational direction than in a rotational direction opposite the one rotational direction so that the contents of the closed slush container rotates from a first starting point before one cycle of complex movements to a second starting point before a next cycle of complex movements.

7. The method of claim 1 wherein the closed slush container is subject to:

a series of repeated cycles of complex movements; within a cycle of complex movements, the closed slush container is rotated in a first rotational direction; and the cycle of complex movements includes periodically lifting a portion of the slush container and dropping the portion of the slush container to alternate between moving the air gap within the slush container towards a bottom end and towards a lid end; and the closed slush container rotating over time relative to a carriage assembly so that the closed slush container is at a first starting point before one cycle of complex movements and is moved to a second starting point before a next cycle of complex movements.

8. The method of claim 7 wherein periodically lifting the portion of the slush container and dropping the portion of the slush container includes use of humps on the carriage assembly which rotate with the carriage assembly.

9. The method of claim 7 wherein periodically lifting the portion of the slush container and dropping the portion of the slush container includes having the slush container fall into a trough in the carriage assembly and rise out of the trough as the carriage assembly rotates.

10. The method of claim 7 wherein periodically lifting the portion of the slush container and dropping the portion of the slush container includes use of stimulus that does not rotate with the carriage assembly other than a set of components used to rotate the carriage assembly.

11. The method of claim 1 wherein a temperature range for a temperature of ambient air within the cooling compartment is set for:

a first temperature range to promote rapid creation of surgical slush before switching to a second warmer temperature range for use to maintain surgical slush within the closed slush container.

12. The method of claim 1 wherein a cross section of an interior of the slush container taken perpendicular to a longitudinal centerline of the slush container is a circle.

13. The method of claim 1 wherein a cross section of an interior of the slush container taken perpendicular to a longitudinal centerline of the slush container is not a circle.

14. A method for making surgical slush; the method comprising:

obtaining a closed slush container having contents of liquid saline and an air gap;

the closed slush container having a set of interior walls including a bottom end surface of the closed slush container and a lid end surface of the closed slush container;

inserting the closed slush container into a cooling compartment with ambient air;

moving the closed slush container to impart accelerations on the contents of the closed slush container so the contents move in a complex set of motions rather than constant rotation around a fixed axis of rotation of the slush container as at least a portion of an exterior of the closed slush container is exposed to ambient air cooled below a freezing temperature for the liquid saline contained in the closed slush container as the liquid saline is converted into surgical slush with a mixture of liquid saline and ice crystals; and wherein the slush container is sufficiently translucent so that a position of a clump of surgical slush may be discerned by looking through at least a portion of the slush container.

15. The method of claim 1 wherein the closed slush container has a volume ratio of liquid saline to air gap is in a range of one-to-one to nine-to-one.

16. The method of claim 1 wherein the closed slush container has a volume ratio of liquid saline to air gap is in a nominal range of four-to-one.

17. A method for making surgical slush; the method comprising:

obtaining a closed slush container having contents of liquid saline and an air gap;

the closed slush container having a set of interior walls including a bottom end surface of the closed slush container and a lid end surface of the closed slush container;

inserting the closed slush container into a cooling compartment with ambient air;

moving the closed slush container to impart accelerations on the contents of the closed slush container so the contents move in a complex set of motions rather than constant rotation around a fixed axis of rotation of the slush container as at least a portion of an exterior of the closed slush container is exposed to ambient air cooled below a freezing temperature for the liquid saline contained in the closed slush container as the liquid saline is converted into surgical slush with a mixture of liquid saline and ice crystals; and wherein the moving of the closed slush container to impart accelerations on the contents of the closed slush container so the contents move in the complex set of motions includes use of stimulus applied by a front plate and a distal plate to the closed slush container to periodically drop the closed slush container without using the front plate and distal plate to impose a change in a relative orientation of a lid end of the closed slush container relative to a bottom end of the closed slush container.

18. A method of making surgical slush within a closed slush container as an exterior of the closed slush container is cooled to convert liquid saline to surgical slush comprising a mixture of ice crystals and liquid saline; the method comprising:

obtaining a closed slush container with contents of liquid saline and an air gap; the closed slush container having a set of interior surfaces that are smooth and hydrophobic to resist adherence of ice crystals;

periodically altering an orientation of the closed slush container by lifting a portion of an exterior surface of the closed slush container relative to a centerline of rotation of a rotating carriage that contains the closed slush container causing the air gap to move within the closed slush container to:

change what portion of a bottom end surface of the closed slush container is exposed to the air gap;

change what portion of a lid end surface of the closed slush containers is exposed to the air gap; and change what portion of the closed slush container between the bottom end surface and the lid end surface is exposed to the air gap; and wherein movements of the closed slush container cause portions of the set of interior surfaces to enter the air gap so that ice crystals within the air gap move away from the portions of the set of the interior surfaces.

19. The method of claim 18 wherein a first starting position of the closed slush container at a beginning of a first cycle of movements of the closed slush container is different from a second starting position of the closed slush container at a beginning of a second cycle of movements of the closed slush container so that a first set of portions of the closed slush container spend time in the air gap during the first cycle of movements and a second set of portions of the set of interior surfaces spend time in the air gap during the second cycle of movements wherein the second set of portions is at least partially different from the first set of portions.

20. The method of claim 19 wherein a slope of a longitudinal centerline of the closed slush container changes during the first cycle of movements so that:

a first amount of a bottom surface area of the bottom end surface in the air gap varies during the first cycle of movements; and a second amount of a lid surface area of the lid end surface in the air gap varies during the first cycle of movements.

21. The method of claim 18 wherein the slush container is rotated around a longitudinal axis for more than one full rotation and the step of causing the air gap to move within the closed slush container includes changing an elevation of a lid end of the slush container relative to a bottom end of the slush container by a combination of lifting and dropping portions of the slush container.

22. The method of claim 21 wherein the lifting and dropping is accomplished through use of at least one hump that is part of a rotating slush carriage containing the slush container.

23. A method of making surgical slush within a closed slush container as an exterior of the closed slush container is cooled to convert liquid saline to surgical slush comprising a mixture of ice crystals and liquid saline; the method comprising:

obtaining a closed slush container with contents of liquid saline and an air gap;

causing the air gap to move within the closed slush container to:

change what portion of a bottom end surface of the closed slush container is exposed to the air gap;

change what portion of a lid surface of the closed slush containers is exposed to the air gap; and change what portion of the closed slush container between the bottom end surface and the lid surface is exposed to the air gap;

wherein movements of the closed slush container cause portions of the set of interior surfaces to enter the air gap so that ice crystals within the air gap move away from the portions of the set of the interior surfaces;

wherein the slush container is rotated around a longitudinal axis for more than one full rotation and the step of causing the air gap to move within the closed slush container includes changing an elevation of a lid of the slush container relative to a bottom end of the slush container by a combination of lifting and dropping portions of the slush container; and wherein the lifting and dropping is accomplished through use of at least one trough in a rotating slush carriage containing the slush container so that the slush container falls into the trough and is later lifted out of the trough as the slush container rotates within the rotating slush carriage.

24. A method of removing ice from a set of interior walls within an interior of a closed slush container while chilling contents of the closed slush container to make surgical slush; the method comprising:

obtaining a closed slush container with contents of liquid saline and an air gap;

the closed slush container having the set of interior walls including:

a bottom end surface of the closed slush container;

a lid end surface of the close slush container; and sidewalls between the bottom end surface and the lid end surface of the closed slush container;

the set of interior walls are smooth and hydrophobic to resist adherence of ice crystals to the set of interior walls as cooling is applied to an exterior of the closed slush container;

moving the closed slush container in a sequence of repeated cycles of complex movements; within each cycle of complex movements:

rotating the closed slush container in a first rotational direction around an axis of rotation of the closed slush container for at least one full rotation of the closed slush container;

rapidly altering an angle of a longitudinal axis of the closed slush container with respect to horizontal to move the air gap towards the bottom end of the closed slush container by allowing the container to fall within a carriage; and rapidly altering the angle of the longitudinal axis of the closed slush container with respect to horizontal to move the air gap towards the lid end of the closed slush container; and the method of removing ice causing at least some portions of the sidewalls to periodically enter and leave the air gap to help dislodge ice crystals from the sidewalls.

25. The method of claim 24 where the air gap reaches the bottom end surface of the closed slush container while being out of contact with the lid end surface of the closed slush container; and later the air gap reaches the lid end surface of the closed slush container while being out of contact with the bottom end surface of the closed slush container.

26. The method of claim 24 wherein stimulus is provided for:

rapidly altering an angle of the longitudinal axis with respect to horizontal to move the air gap Towards the bottom end of the closed slush container; and rapidly altering the angle of the longitudinal axis with respect to horizontal to move the air gap towards the lid end of the closed slush container; and the stimulus provided at least in part by having the closed slush container make temporary contact with features in a rotating carriage assembly.

27. A method of removing ice from a set of interior walls within an interior of a closed slush container while chilling contents of the closed slush container to make surgical slush; the method comprising:

obtaining a closed slush container with contents of liquid saline and an air gap;

the closed slush container having the set of interior walls including:

a bottom end surface of the closed slush container;

a lid end surface of the close slush container; and sidewalls between the bottom end surface and the lid end surface of the closed slush container;

moving the closed slush container in a sequence of repeated cycles of complex movements; within each cycle of complex movements:

rotating the closed slush container in a first rotational direction around an axis of rotation of the closed slush container for at least one full rotation of the closed slush container;

rapidly altering an angle of a longitudinal axis of the closed slush container with respect to horizontal to move the air gap towards bottom end of the closed slush container; and rapidly altering the angle of the longitudinal axis of the closed slush container with respect to horizontal to move the air gap towards lid end of the closed slush container;

the method of removing ice causing at least some portions of the sidewalls to periodically enter and leave the air gap to help dislodge ice crystals from the sidewalls; and wherein after rotating the closed slush container in the first rotational direction around the axis of rotation of the closed slush container for at least one full rotation of the closed slush container, the closed slush container is rotated in a second rotational direction, opposite of the first rotational direction around the axis of rotation of the closed slush container for at least one full rotation of the closed slush container.

28. A method of removing ice from a set of interior walls within an interior of a closed slush container while chilling contents of the closed slush container to make surgical slush; the method comprising:

obtaining a closed slush container with contents of liquid saline and an air gap;

the closed slush container having the set of interior walls including a bottom end surface of the closed slush container, and a lid end surface, and sidewalls between the bottom end surface and the lid end surface;

the set of interior walls are smooth and hydrophobic to resist adherence of ice crystals to the set of interior walls as cooling is applied to an exterior of the closed slush container;

moving the closed slush container in a sequence of repeated cycles of complex movements; within each cycle of complex movements:

rotating the closed slush container in a first rotational direction around an axis of rotation of the closed slush container and in a second rotational direction, opposite to the first rotational direction so that asymmetric rotation reversals cause the contents of the closed slush container to move from a first starting point before one cycle of complex movements to a second starting point, different from the first starting point, before a start of a second cycle of complex movements; and a combination of a magnitude of the air gap, orientation of a longitudinal centerline of the closed slush container, and the rotation of the closed slush container causing all portions of the sidewalls to periodically enter and leave the air gap to help dislodge ice crystals from the sidewalls.

29. The method of claim 28 wherein the closed slush container is placed within a carriage within a cooling chamber in a slush freezer and the closed slush container moves relative to the carriage as the carriage moves to impart the cycles of complex movements upon the closed slush container.

30. The method of claim 28 wherein a slope of the longitudinal centerline of the closed slush container changes within each cycle of complex movements so that the air gap moves to alternatively expose more of the bottom end surface of the closed slush container and more of the lid end surface.

31. The method for making surgical slush of claim 1 wherein the liquid saline includes at least one clinically appropriate material selected from the group consisting of sugars, vitamins, enzymes, and bioactive agents.

32. A method of removing ice from a set of interior walls within an interior of a closed slush container while chilling contents of the closed slush container to make surgical slush; the method comprising:

obtaining a closed slush container with contents of liquid saline and an air gap;

the closed slush container having the set of interior walls including:

a bottom end surface of the closed slush container;

a lid end surface of the close slush container; and sidewalls between the bottom end surface and the lid end surface of the closed slush container;

the set of interior walls are smooth and hydrophobic to resist adherence of ice crystals to the set of interior walls as cooling is applied to an exterior of the closed slush container;

moving the closed slush container in a sequence of repeated cycles of complex movements; within each cycle of complex movements:

rotating the closed slush container in a first rotational direction around an axis of rotation of the closed slush container for at least one full rotation of the closed slush container;

rapidly altering an angle of a longitudinal axis of the closed slush container with respect to horizontal to move the air gap towards the bottom end of the closed slush container; and rapidly altering the angle of the longitudinal axis of the closed slush container with respect to horizontal to move the air gap towards the lid end of the closed slush container by allowing the container to fall within a carriage; and the method of removing ice causing at least some portions of the sidewalls to periodically enter and leave the air gap to help dislodge ice crystals from the sidewalls.

* * * * *

UNITED STATES PATENT AND TRADEMARK OFFICE
CERTIFICATE OF CORRECTION

PATENT NO.        : 9,549,843 B2                                      Page 1 of 1
APPLICATION NO.   : 14/875589
DATED             : January 24, 2017
INVENTOR(S)       : Kammer et al.

It is certified that error appears in the above-identified patent and that said Letters Patent is hereby corrected as shown below:

In the Claims

Column 43, Line 23, 'close slush' should read -closed slush-.
Column 43, Line 60, 'Towards' should read -towards-.
Column 44, Line 10, 'close slush' should read -closed slush-.
Column 44, Line 23, 'towards bottom' should read -towards the bottom-.
Column 44, Line 27, 'towards lid' should read -towards the lid-.
Column 46, Line 2, 'close slush' should read -closed slush-.

Signed and Sealed this
Seventh Day of March, 2017

Michelle K. Lee
*Director of the United States Patent and Trademark Office*